(12) United States Patent
Dickson et al.

(10) Patent No.: US 7,355,015 B1
(45) Date of Patent: Apr. 8, 2008

(54) MATRIPTASE, A SERINE PROTEASE AND ITS APPLICATIONS

(75) Inventors: Robert B. Dickson, Silver Spring, MD (US); Chen-Yong Lin, Falls Church, VA (US); Michael Johnson, Rockville, MD (US); Shaomeng Wang, Rockville, MD (US); Istvan Enyedy, Mount Ranier, MD (US)

(73) Assignee: Georgetown University School of Medicine, Washington, DC (US)

( * ) Notice: Subject to any disclaimer, the term of this patent is extended or adjusted under 35 U.S.C. 154(b) by 634 days.

(21) Appl. No.: 09/936,333

(22) PCT Filed: Mar. 10, 2000

(86) PCT No.: PCT/US00/06111

§ 371 (c)(1),
(2), (4) Date: Mar. 5, 2002

(87) PCT Pub. No.: WO00/53232

PCT Pub. Date: Sep. 14, 2000

Related U.S. Application Data

(60) Provisional application No. 60/124,006, filed on Mar. 12, 1999.

(51) Int. Cl.
*C07K 16/00* (2006.01)
*C07K 16/40* (2006.01)
*A61K 38/43* (2006.01)

(52) U.S. Cl. .............................. 530/388.26; 530/387.1; 530/387.9; 530/388.1; 424/94.1

(58) Field of Classification Search ............... 424/94.1, 424/94.64, 94.67, 130.1, 133.1, 135.1, 138.1, 424/139.1, 141.1, 146.1, 155.1, 156.1, 179.1, 424/178.1; 530/300, 350, 361, 387.1, 387.3, 530/387.7, 388.1, 388.16, 388.8, 388.85, 530/389.1, 391.1; 435/4, 7.1, 7.2, 7.23, 23, 435/287.2, 183, 219; 436/64
See application file for complete search history.

(56) References Cited

U.S. PATENT DOCUMENTS

| | | | | |
|---|---|---|---|---|
| 5,084,266 A | * | 1/1992 | McKenzie et al. | 424/1.49 |
| 5,482,848 A | * | 1/1996 | Dickson et al. | 435/219 |
| 5,516,637 A | * | 5/1996 | Huang et al. | 435/6 |
| 5,972,616 A | * | 10/1999 | O'Brien et al. | 435/6 |
| 6,077,938 A | * | 6/2000 | Dickson et al. | 530/388.26 |

OTHER PUBLICATIONS

Sequence Alignment, p. 2, us-09-936-333-27-rai (alignment of SEQ ID No. 27 and SEQ ID No. 2 of U.S. Appl. No. 09/027,337- patent 5,972,616), no date available.*
Lin et al., Journal of Biological Chemistry, vol. 272 No. 14, pp. 9147-9152 (Apr. 1997).*
O'Brien et al,. Tumor Biology, vol. 19 Supp. 2, p. 33 (Aug. 1998).*
Tanimoto et al., Proceedings of the American Association for Cancer Research Annual Meeting (Mar. 1998), Colume 30, p. 648.*

* cited by examiner

*Primary Examiner*—Zachariah Lucas
(74) *Attorney, Agent, or Firm*—Pillsbury Winthrop Shaw Pittman, LLP

(57) ABSTRACT

The invention is directed to a method of detecting a malignancy or a pre-malignant lesion in breast or other tissue, or a pathologic condition, by detecting the presence of single-chain or two-chain forms of matriptase in the tissue. The invention is further directed to a method of treating malignancies, which have the phenotype of matriptase production by administering a tumor formation inhibiting effective amount of concentrate of Bowman-Birk inhibitor (BBIC), or other matriptase inhibitor. The invention also is directed to nucleic acids encoding a matriptase protein or fragments thereof, and their use for structure elucidation and modeling to identify other inhibitors of matriptase, as well as to methods of identifying matriptase modulating agents, including activators and inhibitors.

7 Claims, 12 Drawing Sheets

```
  1 MAPARTMARARLAPAGIPAVALWLLCTLGLQGTQAGPPPA
 41 PPGLPAGADCLNSFTAGVPGFVLDTNASVSNGATFLESPT
 81 VRRGWDCVRACCTTQNCNLALVELQPDRGEDAIAACFLIN
121 CLYEQNFVCKFAPREGFINYLTREVYRSYRQLRTQGFGGS
161 GIPKAWAGIDLKVQPQEPLVLKDVENTDWRLLRGDTDVRV
201 ERKDPNOVELWGLKEGTYLFQLTVTSSDHPEDTANVTVTV
241 LSTKQTEDYCLASNKVGRCRGSFPRWYYDPTEQICKSFVY
281 GGCLGNKNNYLREEECILACRGVQGPSMERRHPVCSGTCQ
321 PTQFRCSNGCCIDSFLECDDTPNCPDASDEAACEKYTSGF
361 DELQRIHFPSDKGHCVDLPDTGLCKESIPRWYYNPFSEHC
401 ARFTYGGCYGNKNNFEEEQQCLESCRGISKKDVFGLRREI
441 PIPSDGSVEMAVAVFLVICIVVVVAILGYCFFKNQRKDFH
481 GHHHHPPPTPASSTVSTTEDTEHLVYNHTTRPL
```

FIG. 5

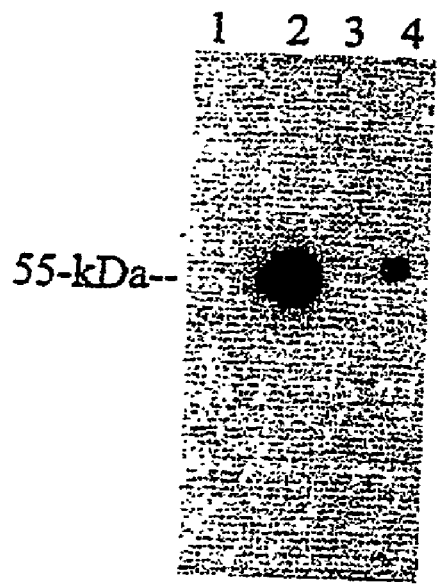

A LDL-receptor type regions

```
Matriptase (280-314)   PCPG--QFTCRTGRCIRKELR-CDGWADCTDHSDELNC
          (315-351)   SCDAGHQFTCKNKFCKPLFWV-CDSVNDCGDNSDEQGC
          (352-387)   SCPA-QTFRCSNGKCLSKSQ-QCNGKDDCGDGSDEASC
          (394-430)   TCTK-HTYRCLNGLCLSKGNPECDGKEDCSDGSDEKDC Consensus sequences
    LDL-receptor      TC····EFC··G·CI···W·-CD···DC·DGSDE··C
           LRP        ·C····FC···RCIP··W·-CDG··DC·D·SDE··C
       Perlecan       PC·P··EFC····C······-CD···DC·D·SDE··C
         GP-330       ·C····FC···C·······-CDG··DC·DGSDE··C
```

B C1r/s type region

```
Mt   (1)  42  CSFGLHARGVELMRFTIRGFPDSPYPAHARCQWALRGDADSVLSLTFRS--FDLASCDERGSDLVT
Mt   (2) 168  CGGRLRKAQ-GT--FMSRYYPG-HYPPNIDCTWNIEVPNNQHVKVRF-KFFYLLEPGVPAGT---C
C1r  (2) 193  CSSELYTEASGY--ISSLEYPR-SYPPDLRCNYSIRVERGLTLHLKFL-EPFDIDD-HQQVH---C
C1s  (2) 175  CSGDVFTALIGE--IASPNYPK-PYPENSRCEYQIRLEKGFQVVVTLRREDFDVEAADSAGN---C
RaRF (2) 185  CSDNLFTORTGV--ITSPDFPN-PYPKSSECLYTIELEEGFHVNLQFE-DIFDIED-HPEVP---C
CSP  (2) 181  CSGDVFTALIGE--IASPNYPK-PYPENSRCEYQIRLEKGFQVVVTLRREDFDVEAADSAGN---C

Mt   (1) 107  VYNTLS-PMEPHALVQLCGTYFPSYNLTFHSSCNVLLITLITNTERRHFGF 155
Mt   (2) 226  PKDYVEINGEK-----YCGER-HS-QFVVTSNSNKITVRFHSDQSYTDTGF 268
C1r  (2) 251  PYDDLQIYANGKNIGEFCGKQRPP-DLD--TSSNAVDLLFFTDESGDSRGW 298
C1s  (2) 235  L-DSLVFVAGDRQFGPYCGHGFPG-PLNIETKSNALDIFQTDLTGQKKGW 283
RaRF (2) 243  PYDYIKIKVGPKVLGPFCQEKAPE-PIS--TQSHSVLIUFHSDNSGENRGW 290
CSP  (2) 241  Q-DSLLFAAKNRQFGPFCGNGFEG-PLTIETHSNTLDIVBQTDLTEQKKGW 289
```

FIG. 11

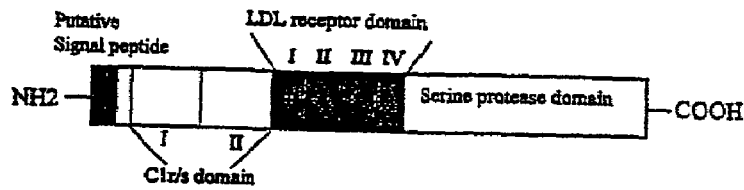

FIG. 12

```
   1 gacgcctgtg agacccgcga gcggcctcgg ggaccatggg gagcgatcgg gcccgcaagg
  61 gcggaggggg cccgaaggac ttcggcgcgg gactcaagta caactcccgg cacgagaaag
 121 tgaatggctt ggaggaaggc gtggagttcc tgccagtcaa caacgtcaag aaggtggaaa
 181 agcatggccc ggggcgctgg gtggtgctgg cagccgtgct gatcggcctc ctcttggtct
 241 tgctggggat cggcttcctg gtgtggcatt tgcagtaccg ggacgtgcgt gtccagaagg
 301 tcttcaatgg ctacatgagg atcacaaatg agaatttgt ggatgcctac gagaactcca
 361 actccactga gtttgtaagc ctggccagca aggtgaagga cgcgctgaag ctgctgtaca
 421 gcggagtccc attcctgggc cctaccaca aggagtcggc tgtgacggcc ttcagcgagg
 481 gcagcgtcat cgcctactac tggtctgagt tcagcatccc gcagcacctg gtggaggagg
 541 ccgagcgcgt catggccgag gagcgcgtag tcatgctgcc cccgcgggcg cgctccctga
 601 agtcctttgt ggtcacctca gtggtggctt ccccacgga ctccaaaaca gtacagagga
 661 cccaggacaa cagctgcagc tttggcctgc acgcccgcg tgtggagctg atgcgcttca
 721 ccacgcccgg cttccctgac agcccctacc ccgctcatgc ccgctgccag tgggccctgc
 781 gggggacgc cgactcagtg ctgagcctca ccttccgcag ctttgacctt gcgtcctgcg
 841 acgagcgcgg cagcgacctg gtgacggtgt acaacaccct gagccccatg gagccccacg
 901 ccctggtgca gttgtgtggc acctaccctc cctcctacaa cctgaccttc cactcctccc
 961 agaacgtcct gctcatcaca ctgataacca acactgagcg gcggcatccc ggctttgagg
1021 ccaccttctt ccagctgcct aggatgagca gctgtggagg ccgcttacgt aaagcccagg
1081 ggacattcaa cagcccctac tacccaggcc actacccacc caacattgac tgcacatgga
1141 acattgaggt gcccaacaac cagcatgtga aggtgcgctt caaattcttc tacctgctgg
1201 agcccggcgt gcctgcgggc acctgcccca aggactacgt ggagatcaat ggggagaaat
1261 actgcggaga gaggtcccag ttcgtcgtca ccagcaacag caacaagatc acagttcgct
1321 tccactcaga tcagtcctac accgacaccg gcttcttagc tgaataccct cctacgact
1381 ccagtgaccc atgccgggg cagttcacgt gccgcacggg gcggtgtatc cggaaggagc
1441 tgcgctgtga tgctgggcc gactgcaccg accacagcga tgagctcaac tgcagttgcg
1501 acgccggcca ccagttcacg tgcaagaaca gttctgcaa gcccctcttc tgggtctgcg
1561 acagtgtgaa cgactgcgga gacaacagcg acgagcaggg gtgcagttgt ccggcccaga
1621 ccttcaggtg ttccaatggg aagtgcctct cgaaaagcca gcagtgcaat gggaaggacg
1681 actgtgggga cgggtccgac gaggcctcct gccccaaggt gaacgtcgtc acttgtacca
1741 aacacaccta ccgctgcctc aatgggctct gcttgagcaa gggcaaccct gagtgtgacg
1801 ggaaggagga ctgtagcgac ggctcagatg agaaggactg cgactgtggg ctgcggtcat
1861 tcacgagaca ggctcgtgtt gttggggca cggatgcgga tgagggcgag tggccctggc
1921 aggtaagcct gcatgctctg ggccagggcc acatctgcgg tgcttccctc atctctccca
1981 actggctggt ctctgccgca cactgctaca tcgatgacag aggattcagg tactcagacc
2041 ccacgcagtg gacggccttc ctgggcttgc acgaccagag ccagcgcagc gccctggggg
2101 tgcaggagcg caggctcaag cgcatcatct cccacccctt cttcaatgac ttcaccttcg
2161 actatgacat cgcgctgctg gagctggaga aaccggcaga gtacagctcc atggtgcggc
2221 ccatctgcct gccggacgcc tccatgtct tcctgccgg caaggccatc tgggtcacgg
2281 gctggggaca cacccagtat ggaggcactg gcgcgctgat cctgcaaaag ggtgagatcc
2341 gcgtcatcaa ccagaccacc tgcgagaacc tcctgccgca gcagatcacg ccgcgcatga
2401 tgtgcgtggg cttcctcagc ggcggcgtgg actcctgcca gggtgattcc gggggacccc
2461 tgtccagcgt ggaggcggat gggcggatct tccaggccgg tgtggtgagc tggggagacg
2521 gctgcgctca gaggaacaag ccaggcgtgt acacaaggct ccctctgttt cgggactgga
2581 tcaaagagaa cactggggta taggggccgg ggccacccaa atgtgtacac ctgcggggcc
2641 acccatcgtc caccccagtg tgcacgcctg caggctggag actggaccgc tgactgcacc
2701 agcgccccca gaacatacac tgtgaactca atctccaggg ctccaaatct gcctagaaaa
2761 cctctcgctt cctcagcctc caaagtggag ctgggaggta gaggggagg acactggtgg
2821 ttctactgac ccaactgggg gcaaaggttt gaagacacag cctcccccgc cagccccaag
2881 ctgggccgag gcgcgtttgt gtatatctgc ctccctgtc tgtaaggagc agcgggaacg
2941 gagcttcgga gcctcctcag tgaaggtggt ggggctgccg gatctgggct gtgggccct
3001 tgggccacgc tcttgaggaa gcccaggctc ggaggaccct ggaaaacaga cgggtctgag
3061 actgaaaatg gtttaccagc tcccaggtga cttcagtgtg tgtattgtgt aaatgagtaa
3121 aacattttat ttcttttaa aaaaaaaa
```

FIG. 15

```
  1 mgsdrarkgg ggpkdfgagl kynsrhekvn gleegveflp vnnvkkvekh gpgrwvvlaa
 61 vliglllvll gigflvwhlq yrdvrvqkvf ngymritnen fvdayensns tefvslaskv
121 kdalkllysg vpflgpyhke savtafsegs viayywsefs ipqhlveeae rvmaeervvm
181 lpprarslks fvvtsvvafp tdsktvqrtq dnscsfglha rgvelmrftt pgfpdspypa
241 harcqwalrg dadsvlsltf rsfdlascde rgsdlvtvyn tlspmephal vqlcgtypps
301 ynltfhssqn vllitlitnt errhpgfeat ffqlprmssc ggrlrkaqgt fnspyypghy
361 ppnidctwni evpnnqhvkv rfkffyllep gvpagtcpkd yveingekyc gersqfvvts
421 nsnkitvrfh sdqsytdtgf laeylsydss dpcpgqftcr tgrcirkelr cdgwadctdh
481 sdelncscda ghqftcknkf ckplfwvcds vndcgdnsde qgcscpaqtf rcsngkclsk
541 sqqcngkddc gdgsdeascp kvnvvtctkh tyrclnglcl skgnpecdgk edcsdgsdek
601 dcdcglrsft rqarvvggtd adegewpwqv slhalgqghi cgaslispnw lvsaahcyid
661 drgfrysdpt qwtaflglhd qsqrsapgvq errlkriish pffndftfdy diallelekp
721 aeyssmvrpi clpdashvfp agkaiwvtgw ghtqyggtga lilqkgeirv inqttcenll
781 pqqitprmmc vgflsggvds cqgdsggpls sveadgrifq agvvswgdgc aqrnkpgvyt
841 rlplfrdwik entgv
```

FIG. 16

SEQUENCE LISTING

<160> NUMBER OF SEQ ID NOS: 39

<210> SEQ ID NO 1
<211> LENGTH: 513
<212> TYPE: PRT
<213> ORGANISM: Homo sapiens

<400> SEQUENCE: 1

```
Met Ala Pro Ala Arg Thr Met Ala Arg Ala Arg Leu Ala Pro Ala Gly
  1               5                  10                  15

Ile Pro Ala Val Ala Leu Trp Leu Leu Cys Thr Leu Gly Leu Gln Gly
                 20                  25                  30

Thr Gln Ala Gly Pro Pro Pro Ala Pro Pro Gly Leu Pro Ala Gly Ala
             35                  40                  45

Asp Cys Leu Asn Ser Phe Thr Ala Gly Val Pro Gly Phe Val Leu Asp
         50                  55                  60

Thr Asn Ala Ser Val Ser Asn Gly Ala Thr Phe Leu Glu Ser Pro Thr
     65                  70                  75                  80

Val Arg Arg Gly Trp Asp Cys Val Arg Ala Cys Cys Thr Thr Gln Asn
                 85                  90                  95

Cys Asn Leu Ala Leu Val Glu Leu Gln Pro Asp Arg Gly Glu Asp Ala
                100                 105                 110

Ile Ala Ala Cys Phe Leu Ile Asn Cys Leu Tyr Glu Gln Asn Phe Val
            115                 120                 125
```

-continued

```
Cys Lys Phe Ala Pro Arg Glu Gly Phe Ile Asn Tyr Leu Thr Arg Glu
    130                 135                 140

Val Tyr Arg Ser Tyr Arg Gln Leu Arg Thr Gln Gly Phe Gly Gly Ser
145                 150                 155                 160

Gly Ile Pro Lys Ala Trp Ala Gly Ile Asp Leu Lys Val Gln Pro Gln
                165                 170                 175

Glu Pro Leu Val Leu Lys Asp Val Glu Asn Thr Asp Trp Arg Leu Leu
            180                 185                 190

Arg Gly Asp Thr Asp Val Arg Val Glu Arg Lys Asp Pro Asn Gln Val
        195                 200                 205

Glu Leu Trp Gly Leu Lys Glu Gly Thr Tyr Leu Phe Gln Leu Thr Val
    210                 215                 220

Thr Ser Ser Asp His Pro Glu Asp Thr Ala Asn Val Thr Val Thr Val
225                 230                 235                 240

Leu Ser Thr Lys Gln Thr Glu Asp Tyr Cys Leu Ala Ser Asn Lys Val
                245                 250                 255

Gly Arg Cys Arg Gly Ser Phe Pro Arg Trp Tyr Tyr Asp Pro Thr Glu
            260                 265                 270

Gln Ile Cys Lys Ser Phe Val Tyr Gly Gly Cys Leu Gly Asn Lys Asn
        275                 280                 285

Asn Tyr Leu Arg Glu Glu Cys Ile Leu Ala Cys Arg Gly Val Gln
    290                 295                 300

Gly Pro Ser Met Glu Arg Arg His Pro Val Cys Ser Gly Thr Cys Gln
305                 310                 315                 320

Pro Thr Gln Phe Arg Cys Ser Asn Gly Cys Cys Ile Asp Ser Phe Leu
                325                 330                 335

Glu Cys Asp Asp Thr Pro Asn Cys Pro Asp Ala Ser Asp Glu Ala Ala
            340                 345                 350

Cys Glu Lys Tyr Thr Ser Gly Phe Asp Glu Leu Gln Arg Ile His Phe
        355                 360                 365

Pro Ser Asp Lys Gly His Cys Val Asp Leu Pro Asp Thr Gly Leu Cys
370                 375                 380

Lys Glu Ser Ile Pro Arg Trp Tyr Tyr Asn Pro Phe Ser Glu His Cys
385                 390                 395                 400

Ala Arg Phe Thr Tyr Gly Gly Cys Tyr Gly Asn Lys Asn Asn Phe Glu
                405                 410                 415

Glu Glu Gln Gln Cys Leu Glu Ser Cys Arg Gly Ile Ser Lys Lys Asp
            420                 425                 430

Val Phe Gly Leu Arg Arg Glu Ile Pro Ile Pro Ser Asp Gly Ser Val
        435                 440                 445

Glu Met Ala Val Ala Val Phe Leu Val Ile Cys Ile Val Val Val Val
    450                 455                 460

Ala Ile Leu Gly Tyr Cys Phe Lys Asn Gln Arg Lys Asp Phe His
465                 470                 475                 480

Gly His His His Pro Pro Thr Pro Ala Ser Ser Thr Val Ser
                485                 490                 495

Thr Thr Glu Asp Thr Glu His Leu Val Tyr Asn His Thr Thr Arg Pro
            500                 505                 510

Leu
```

<210> SEQ ID NO 2
<211> LENGTH: 12
<212> TYPE: PRT

-continued

<213> ORGANISM: Homo sapiens

<400> SEQUENCE: 2

```
Gly Pro Pro Pro Ala Pro Pro Gly Leu Pro Ala Gly
 1               5                  10
```

<210> SEQ ID NO 3
<211> LENGTH: 7
<212> TYPE: PRT
<213> ORGANISM: Homo sapiens

<400> SEQUENCE: 3

```
Thr Gln Gly Phe Gly Gly Ser
 1               5
```

<210> SEQ ID NO 4
<211> LENGTH: 2955
<212> TYPE: DNA
<213> ORGANISM: Homo sapiens
<220> FEATURE:
<221> NAME/KEY: CDS
<222> LOCATION: (358)..(2409)

<400> SEQUENCE: 4

| | |
|---|---|
| cgctgggtgg tgctggcagc cgtgctgatc ggcctcctct tggtcttgct ggggatcggc | 60 |
| ttcctggtgt ggcatttgca gtaccgggac gtgcgtgtcc agaaggtctt caatggctac | 120 |
| atgaggatca caaatgagaa ttttgtggat gcctacgaga actccaactc cactgagttt | 180 |
| gtaagcctgg ccagcaaggt gaaggacgcg ctgaagctgc tgtacagcgg agtcccattc | 240 |
| ctgggcccct accacaagga gtcggctgtg acggccttca gcgagggcag cgtcatcgcc | 300 |
| tactactggt ctgagttcag catcccgcag cacctggtgg aggaggccga gcgcgtc | 357 |

```
atg gcc gag gag cgc gta gtc atg ctg ccc ccg cgg gcg cgc tcc ctg      405
Met Ala Glu Glu Arg Val Val Met Leu Pro Pro Arg Ala Arg Ser Leu
 1               5                  10                  15 aag tcc ttt gtg gtc acc tca gtg gtg gct ttc ccc acg gac tcc aaa      453
Lys Ser Phe Val Val Thr Ser Val Val Ala Phe Pro Thr Asp Ser Lys
             20                  25                  30 aca gta cag agg acc cag gac aac agc tgc agc ttt ggc ctg cac gcc      501
Thr Val Gln Arg Thr Gln Asp Asn Ser Cys Ser Phe Gly Leu His Ala
         35                  40                  45 cgc ggt gtg gag ctg atg cgc ttc acc acg ccc ggc ttc cct gac agc      549
Arg Gly Val Glu Leu Met Arg Phe Thr Thr Pro Gly Phe Pro Asp Ser
     50                  55                  60 ccc tac ccc gct cat gcc cgc tgc cag tgg gcc ctg cgg ggg gac gcc      597
Pro Tyr Pro Ala His Ala Arg Cys Gln Trp Ala Leu Arg Gly Asp Ala
 65                  70                  75                  80 gac tca gtg ctg agc ctc acc ttc cgc agc ttt gac ctt gcg tcc tgc      645
Asp Ser Val Leu Ser Leu Thr Phe Arg Ser Phe Asp Leu Ala Ser Cys
                 85                  90                  95 gac gag cgc ggc agc gac ctg gtg acg gtg tac aac acc ctg agc ccc      693
Asp Glu Arg Gly Ser Asp Leu Val Thr Val Tyr Asn Thr Leu Ser Pro
            100                 105                 110 atg gag ccc cac gcc ctg gtg cag ttg tgt ggc acc tac cct ccc tcc      741
Met Glu Pro His Ala Leu Val Gln Leu Cys Gly Thr Tyr Pro Pro Ser
        115                 120                 125 tac aac ctg acc ttc cac tcc tcc cag aac gtc ctg ctc atc aca ctg      789
Tyr Asn Leu Thr Phe His Ser Ser Gln Asn Val Leu Leu Ile Thr Leu
    130                 135                 140 ata acc aac act gag cgg cgg cat ccc ggc ttt gag gcc acc ttc ttc      837
Ile Thr Asn Thr Glu Arg Arg His Pro Gly Phe Glu Ala Thr Phe Phe
```

-continued

```
              145                 150                 155                 160
cag ctg cct agg atg agc agc tgt gga ggc cgc tta cgt aaa gcc cag              885
Gln Leu Pro Arg Met Ser Ser Cys Gly Gly Arg Leu Arg Lys Ala Gln
                165                 170                 175 ggg aca ttc aac agc ccc tac tac cca ggc cac tac cca ccc aac att              933
Gly Thr Phe Asn Ser Pro Tyr Tyr Pro Gly His Tyr Pro Pro Asn Ile
        180                 185                 190 gac tgc aca tgg aac att gag gtg ccc aac aac cag cat gtg aag gtg              981
Asp Cys Thr Trp Asn Ile Glu Val Pro Asn Asn Gln His Val Lys Val
            195                 200                 205 cgc ttc aaa ttc ttc tac ctg ctg gag ccc cgg cgt gcc tgc ggc acc             1029
Arg Phe Lys Phe Phe Tyr Leu Leu Glu Pro Arg Arg Ala Cys Gly Thr
        210                 215                 220 tgc ccc aag gac tac gtg gag atc aat ggg gag aaa tac tgc gga gag             1077
Cys Pro Lys Asp Tyr Val Glu Ile Asn Gly Glu Lys Tyr Cys Gly Glu
225                 230                 235                 240 agg tcc cag ttc gtc gtc acc agc aac agc aac aag atc aca gtt cgc             1125
Arg Ser Gln Phe Val Val Thr Ser Asn Ser Asn Lys Ile Thr Val Arg
                245                 250                 255 ttc cac tca gat cag tcc tac acc gac acc ggc ttc tta gct gaa tac             1173
Phe His Ser Asp Gln Ser Tyr Thr Asp Thr Gly Phe Leu Ala Glu Tyr
        260                 265                 270 ctc tcc tac gac tcc agt gac cca tgc ccg ggg cag ttc acg tgc cgc             1221
Leu Ser Tyr Asp Ser Ser Asp Pro Cys Pro Gly Gln Phe Thr Cys Arg
            275                 280                 285 acg ggg cgg tgt atc cgg aag gag ctg cgc tgt gat ggc tgg gcc gac             1269
Thr Gly Arg Cys Ile Arg Lys Glu Leu Arg Cys Asp Gly Trp Ala Asp
        290                 295                 300 tgc acc gac cac agc gat gag ctc aac tgc agt tgc gac gcc ggc cac             1317
Cys Thr Asp His Ser Asp Glu Leu Asn Cys Ser Cys Asp Ala Gly His
305                 310                 315                 320 cag ttc acg tgc aag aac aag ttc tgc aag ccc ctc ttc tgg gtc tgc             1365
Gln Phe Thr Cys Lys Asn Lys Phe Cys Lys Pro Leu Phe Trp Val Cys
                325                 330                 335 gac agt gtg aac gac tgc gga gac aac agc gac gag cag ggg tgc agt             1413
Asp Ser Val Asn Asp Cys Gly Asp Asn Ser Asp Glu Gln Gly Cys Ser
        340                 345                 350 tgt ccg gcc cag acc ttc agg tgt tcc aat ggg aag tgc ctc tcg aaa             1461
Cys Pro Ala Gln Thr Phe Arg Cys Ser Asn Gly Lys Cys Leu Ser Lys
            355                 360                 365 agc cag cag tgc aat ggg aag gac gac tgt ggg gac ggg tcc gac gag             1509
Ser Gln Gln Cys Asn Gly Lys Asp Asp Cys Gly Asp Gly Ser Asp Glu
        370                 375                 380 gcc tcc tgc ccc aag gtg aac gtc gtc act tgt acc aaa cac acc tac             1557
Ala Ser Cys Pro Lys Val Asn Val Val Thr Cys Thr Lys His Thr Tyr
385                 390                 395                 400 cgc tgc ctc aat ggg ctc tgc ttg agc aag ggc aac cct gag tgt gac             1605
Arg Cys Leu Asn Gly Leu Cys Leu Ser Lys Gly Asn Pro Glu Cys Asp
                405                 410                 415 ggg aag gag gac tgt agc gac ggc tca gat gag aag gac tgc gac tgt             1653
Gly Lys Glu Asp Cys Ser Asp Gly Ser Asp Glu Lys Asp Cys Asp Cys
        420                 425                 430 ggg ctg cgg tca ttc acg aga cag gct cgt gtt gtt ggg ggc acg gat             1701
Gly Leu Arg Ser Phe Thr Arg Gln Ala Arg Val Val Gly Gly Thr Asp
            435                 440                 445 gcg gat gag ggc gag tgg ccc tgg cag gta agc ctg cat gct ctg ggc             1749
Ala Asp Glu Gly Glu Trp Pro Trp Gln Val Ser Leu His Ala Leu Gly
        450                 455                 460 cag ggc cac atc tgc ggt gct tcc ctc atc tct ccc aac tgg ctg gtc             1797
```

```
Gln Gly His Ile Cys Gly Ala Ser Leu Ile Ser Pro Asn Trp Leu Val
465                 470                 475                 480 tct gcc gca cac tgc tac atc gat gac aga gga ttc agg tac tca gac       1845
Ser Ala Ala His Cys Tyr Ile Asp Asp Arg Gly Phe Arg Tyr Ser Asp
                    485                 490                 495 ccc acg cag tgg acg gcc ttc ctg ggc ttg cac gac cag agc cag cgc       1893
Pro Thr Gln Trp Thr Ala Phe Leu Gly Leu His Asp Gln Ser Gln Arg
                500                 505                 510 agc gcc cct ggg gtg cag gag cgc agg ctc aag cgc atc atc tcc cac       1941
Ser Ala Pro Gly Val Gln Glu Arg Arg Leu Lys Arg Ile Ile Ser His
            515                 520                 525 ccc ttc ttc aat gac ttc acc ttc gac tat gac atc gcg ctg ctg gag       1989
Pro Phe Phe Asn Asp Phe Thr Phe Asp Tyr Asp Ile Ala Leu Leu Glu
        530                 535                 540 ctg gag aaa ccg gca gag tac agc tcc atg gtg cgg ccc atc tgc ctg       2037
Leu Glu Lys Pro Ala Glu Tyr Ser Ser Met Val Arg Pro Ile Cys Leu
545                 550                 555                 560 ccg gac gcc tcc cat gtc ttc cct gcc ggc aag gcc atc tgg gtc acg       2085
Pro Asp Ala Ser His Val Phe Pro Ala Gly Lys Ala Ile Trp Val Thr
                    565                 570                 575 ggc tgg gga cac acc cag tat gga ggc act ggc gcg ctg atc ctg caa       2133
Gly Trp Gly His Thr Gln Tyr Gly Gly Thr Gly Ala Leu Ile Leu Gln
                580                 585                 590 aag ggt gag atc cgc gtc atc aac cag acc acc tgc gag aac ctc ctg       2181
Lys Gly Glu Ile Arg Val Ile Asn Gln Thr Thr Cys Glu Asn Leu Leu
            595                 600                 605 ccg cag cag atc acg ccg cgc atg atg tgc gtg ggc ttc ctc agc ggc       2229
Pro Gln Gln Ile Thr Pro Arg Met Met Cys Val Gly Phe Leu Ser Gly
        610                 615                 620 ggc gtg gac tcc tgc cag ggt gat tcc ggg gga ccc ctg tcc agc gtg       2277
Gly Val Asp Ser Cys Gln Gly Asp Ser Gly Gly Pro Leu Ser Ser Val
625                 630                 635                 640 gag gcg gat ggg cgg atc ttc cag gcc ggt gtg gtg agc tgg gga gac       2325
Glu Ala Asp Gly Arg Ile Phe Gln Ala Gly Val Val Ser Trp Gly Asp
                    645                 650                 655 ggc tgc gct cag agg aac aag cca ggc gtg tac aca agg ctc cct ctg       2373
Gly Cys Ala Gln Arg Asn Lys Pro Gly Val Tyr Thr Arg Leu Pro Leu
                660                 665                 670 ttt cgg gac tgg atc aaa gag aac act ggg gta tag gggccggggc            2419
Phe Arg Asp Trp Ile Lys Glu Asn Thr Gly Val
            675                 680 cacccaaatg tgtacacctg cggggccacc catcgtccac cccagtgtgc acgcctgcag     2479
gctggagact ggaccgctga ctgcaccagc gcccccagaa catacactgt gaactcaatc     2539
tccagggctc caaatctgcc tagaaaacct ctcgcttcct cagcctccaa agtggagctg     2599
ggaggtagaa ggggaggaca ctggtggttc tactgaccca actgggggca aaggtttgaa     2659
gacacagcct cccccgccag ccccaagctg ggccgaggcg cgtttgtgta tatctgcctc     2719
ccctgtctgt aaggagcagc gggaacggag cttcggagcc tcctcagtga aggtggtggg     2779
gctgccggat ctgggctgtg gggcccttgg gccacgctct tgaggaagcc caggctcgga     2839
ggaccctgga aaacagacgg gtctgagact gaaaatggtt taccagctcc caggtgactt     2899
cagtgtgtgt attgtgtaaa tgagtaaaac attttatttc tttttaaaaa aaaaaa        2955

<210> SEQ ID NO 5
<211> LENGTH: 683
<212> TYPE: PRT
<213> ORGANISM: Homo sapiens
```

<400> SEQUENCE: 5

```
Met Ala Glu Glu Arg Val Val Met Leu Pro Pro Arg Ala Arg Ser Leu
 1               5                  10                  15

Lys Ser Phe Val Val Thr Ser Val Val Ala Phe Pro Thr Asp Ser Lys
            20                  25                  30

Thr Val Gln Arg Thr Gln Asp Asn Ser Cys Ser Phe Gly Leu His Ala
        35                  40                  45

Arg Gly Val Glu Leu Met Arg Phe Thr Thr Pro Gly Phe Pro Asp Ser
    50                  55                  60

Pro Tyr Pro Ala His Ala Arg Cys Gln Trp Ala Leu Arg Gly Asp Ala
65                  70                  75                  80

Asp Ser Val Leu Ser Leu Thr Phe Arg Ser Phe Asp Leu Ala Ser Cys
                85                  90                  95

Asp Glu Arg Gly Ser Asp Leu Val Thr Val Tyr Asn Thr Leu Ser Pro
            100                 105                 110

Met Glu Pro His Ala Leu Val Gln Leu Cys Gly Thr Tyr Pro Pro Ser
        115                 120                 125

Tyr Asn Leu Thr Phe His Ser Ser Gln Asn Val Leu Leu Ile Thr Leu
    130                 135                 140

Ile Thr Asn Thr Glu Arg Arg His Pro Gly Phe Glu Ala Thr Phe Phe
145                 150                 155                 160

Gln Leu Pro Arg Met Ser Ser Cys Gly Gly Arg Leu Arg Lys Ala Gln
                165                 170                 175

Gly Thr Phe Asn Ser Pro Tyr Tyr Pro Gly His Tyr Pro Pro Asn Ile
            180                 185                 190

Asp Cys Thr Trp Asn Ile Glu Val Pro Asn Asn Gln His Val Lys Val
        195                 200                 205

Arg Phe Lys Phe Phe Tyr Leu Leu Glu Pro Arg Arg Ala Cys Gly Thr
    210                 215                 220

Cys Pro Lys Asp Tyr Val Glu Ile Asn Gly Glu Lys Tyr Cys Gly Glu
225                 230                 235                 240

Arg Ser Gln Phe Val Val Thr Ser Asn Ser Asn Lys Ile Thr Val Arg
                245                 250                 255

Phe His Ser Asp Gln Ser Tyr Thr Asp Thr Gly Phe Leu Ala Glu Tyr
            260                 265                 270

Leu Ser Tyr Asp Ser Ser Asp Pro Cys Pro Gly Gln Phe Thr Cys Arg
    275                 280                 285

Thr Gly Arg Cys Ile Arg Lys Glu Leu Arg Cys Asp Gly Trp Ala Asp
    290                 295                 300

Cys Thr Asp His Ser Asp Glu Leu Asn Cys Ser Cys Asp Ala Gly His
305                 310                 315                 320

Gln Phe Thr Cys Lys Asn Lys Phe Cys Lys Pro Leu Phe Trp Val Cys
                325                 330                 335

Asp Ser Val Asn Asp Cys Gly Asp Asn Ser Asp Glu Gln Gly Cys Ser
            340                 345                 350

Cys Pro Ala Gln Thr Phe Arg Cys Ser Asn Gly Lys Cys Leu Ser Lys
        355                 360                 365

Ser Gln Gln Cys Asn Gly Lys Asp Asp Cys Gly Asp Gly Ser Asp Glu
    370                 375                 380

Ala Ser Cys Pro Lys Val Asn Val Val Thr Cys Thr Lys His Thr Tyr
385                 390                 395                 400

Arg Cys Leu Asn Gly Leu Cys Leu Ser Lys Gly Asn Pro Glu Cys Asp
                405                 410                 415
```

```
Gly Lys Glu Asp Cys Ser Asp Gly Ser Asp Glu Lys Asp Cys Asp Cys
            420                 425                 430

Gly Leu Arg Ser Phe Thr Arg Gln Ala Arg Val Val Gly Gly Thr Asp
            435                 440                 445

Ala Asp Glu Gly Glu Trp Pro Trp Gln Val Ser Leu His Ala Leu Gly
            450                 455                 460

Gln Gly His Ile Cys Gly Ala Ser Leu Ile Ser Pro Asn Trp Leu Val
465                 470                 475                 480

Ser Ala Ala His Cys Tyr Ile Asp Asp Arg Gly Phe Arg Tyr Ser Asp
            485                 490                 495

Pro Thr Gln Trp Thr Ala Phe Leu Gly Leu His Asp Gln Ser Gln Arg
            500                 505                 510

Ser Ala Pro Gly Val Gln Glu Arg Leu Lys Arg Ile Ile Ser His
            515                 520                 525

Pro Phe Phe Asn Asp Phe Thr Phe Asp Tyr Asp Ile Ala Leu Leu Glu
            530                 535                 540

Leu Glu Lys Pro Ala Glu Tyr Ser Ser Met Val Arg Pro Ile Cys Leu
545                 550                 555                 560

Pro Asp Ala Ser His Val Phe Pro Ala Gly Lys Ala Ile Trp Val Thr
            565                 570                 575

Gly Trp Gly His Thr Gln Tyr Gly Gly Thr Gly Ala Leu Ile Leu Gln
            580                 585                 590

Lys Gly Glu Ile Arg Val Ile Asn Gln Thr Thr Cys Glu Asn Leu Leu
            595                 600                 605

Pro Gln Gln Ile Thr Pro Arg Met Met Cys Val Gly Phe Leu Ser Gly
            610                 615                 620

Gly Val Asp Ser Cys Gln Gly Asp Ser Gly Gly Pro Leu Ser Ser Val
625                 630                 635                 640

Glu Ala Asp Gly Arg Ile Phe Gln Ala Gly Val Val Ser Trp Gly Asp
            645                 650                 655

Gly Cys Ala Gln Arg Asn Lys Pro Gly Val Tyr Thr Arg Leu Pro Leu
            660                 665                 670

Phe Arg Asp Trp Ile Lys Glu Asn Thr Gly Val
            675                 680

<210> SEQ ID NO 6
<211> LENGTH: 253
<212> TYPE: PRT
<213> ORGANISM: Homo sapiens

<400> SEQUENCE: 6

Asp Cys Gly Leu Arg Ser Phe Thr Arg Gln Ala Arg Val Val Gly Gly
1               5                   10                  15

Thr Asp Ala Asp Glu Gly Glu Trp Pro Trp Gln Val Ser Leu His Ala
            20                  25                  30

Leu Gly Gln Gly His Ile Cys Gly Ala Ser Leu Ile Ser Pro Asn Trp
        35                  40                  45

Leu Val Ser Ala Ala His Cys Tyr Ile Asp Asp Arg Gly Phe Arg Tyr
    50                  55                  60

Ser Asp Pro Thr Gln Trp Thr Ala Phe Leu Gly Leu His Asp Gln Ser
65                  70                  75                  80

Gln Arg Ser Ala Pro Gly Val Gln Glu Arg Leu Lys Arg Ile Ile
            85                  90                  95

Ser His Pro Phe Phe Asn Asp Phe Thr Phe Asp Tyr Asp Ile Ala Leu
```

```
            100                 105                 110
Leu Glu Leu Glu Lys Pro Ala Glu Tyr Ser Ser Met Val Arg Pro Ile
        115                 120                 125

Cys Leu Pro Asp Ala Ser His Val Phe Pro Ala Gly Lys Ala Ile Trp
    130                 135                 140

Val Thr Gly Trp Gly His Thr Gln Tyr Gly Gly Thr Gly Ala Leu Ile
145                 150                 155                 160

Leu Gln Lys Gly Glu Ile Arg Val Ile Asn Gln Thr Thr Cys Glu Asn
                165                 170                 175

Leu Leu Pro Gln Gln Ile Thr Pro Arg Met Met Cys Val Gly Phe Leu
            180                 185                 190

Ser Gly Gly Val Asp Ser Cys Gln Gly Asp Ser Gly Gly Pro Leu Ser
        195                 200                 205

Ser Val Glu Ala Asp Gly Arg Ile Phe Gln Ala Gly Val Val Ser Trp
    210                 215                 220

Gly Asp Gly Cys Ala Gln Arg Asn Lys Pro Gly Val Tyr Thr Arg Leu
225                 230                 235                 240

Pro Leu Phe Arg Asp Trp Ile Lys Glu Asn Thr Gly Val
                245                 250

<210> SEQ ID NO 7
<211> LENGTH: 249
<212> TYPE: PRT
<213> ORGANISM: Homo sapiens

<400> SEQUENCE: 7

Ser Cys Gly Lys Lys Leu Ala Ala Gln Asp Ile Thr Pro Lys Ile Val
1               5                   10                  15

Gly Gly Ser Asn Ala Lys Glu Gly Ala Trp Pro Trp Val Val Gly Leu
            20                  25                  30

Tyr Tyr Gly Gly Arg Leu Leu Cys Gly Ala Ser Leu Val Ser Ser Asp
        35                  40                  45

Trp Leu Val Ser Ala Ala His Cys Tyr Tyr Gly Arg Asn Leu Glu Pro
    50                  55                  60

Ser Lys Trp Thr Ala Ile Leu Gly Leu His Met Lys Ser Asn Leu Thr
65                  70                  75                  80

Ser Pro Gln Thr Val Pro Arg Leu Ile Asp Glu Ile Val Ile Asn Pro
                85                  90                  95

His Tyr Asn Arg Arg Arg Lys Asp Asn Asp Ile Ala Met Met His Leu
            100                 105                 110

Glu Phe Lys Val Asn Tyr Thr Asp Tyr Ile Gln Pro Ile Cys Leu Pro
        115                 120                 125

Glu Glu Asn Gln Val Phe Pro Pro Gly Arg Asn Cys Ser Ile Ala Gly
    130                 135                 140

Trp Gly Thr Val Val Tyr Gln Gly Thr Thr Ala Asn Ile Leu Gln Glu
145                 150                 155                 160

Ala Asp Val Pro Leu Leu Ser Asn Glu Arg Cys Gln Gln Gln Met Pro
                165                 170                 175

Glu Tyr Asn Ile Thr Glu Asn Met Ile Cys Ala Gly Tyr Glu Glu Gly
            180                 185                 190

Gly Ile Asp Ser Cys Gln Gly Asp Ser Gly Gly Pro Leu Met Cys Gln
        195                 200                 205

Glu Asn Asn Arg Trp Phe Leu Ala Gly Val Thr Ser Phe Gly Tyr Lys
    210                 215                 220
```

```
Cys Ala Leu Pro Asn Arg Pro Gly Val Tyr Ala Arg Val Ser Arg Phe
225                 230                 235                 240

Thr Glu Trp Ile Gln Ser Phe Leu His
                245

<210> SEQ ID NO 8
<211> LENGTH: 250
<212> TYPE: PRT
<213> ORGANISM: Homo sapiens

<400> SEQUENCE: 8

Ala Cys Gly Val Asn Leu Asn Ser Ser Arg Gln Ser Arg Ile Val Gly
1               5                   10                  15

Gly Glu Ser Ala Leu Pro Gly Ala Trp Pro Trp Gln Val Ser Leu His
            20                  25                  30

Val Gln Asn Val His Val Cys Gly Gly Ser Ile Ile Thr Pro Glu Trp
        35                  40                  45

Ile Val Thr Ala Ala His Cys Val Glu Lys Pro Leu Asn Asn Pro Trp
    50                  55                  60

His Trp Thr Ala Phe Ala Gly Ile Leu Arg Gln Ser Phe Met Phe Tyr
65                  70                  75                  80

Gly Ala Gly Tyr Gln Val Gln Lys Val Ile Ser His Pro Asn Tyr Asp
                85                  90                  95

Ser Lys Thr Lys Asn Asn Asp Ile Ala Leu Met Lys Leu Gln Lys Pro
            100                 105                 110

Leu Thr Phe Asn Asp Leu Val Lys Pro Val Cys Leu Pro Asn Pro Gly
        115                 120                 125

Met Met Leu Gln Pro Glu Gln Leu Cys Trp Ile Ser Gly Trp Gly Ala
    130                 135                 140

Thr Glu Glu Lys Gly Lys Thr Ser Glu Val Leu Asn Ala Ala Lys Val
145                 150                 155                 160

Leu Leu Ile Glu Thr Gln Arg Cys Asn Ser Arg Tyr Val Tyr Asp Asn
                165                 170                 175

Leu Ile Thr Pro Ala Met Ile Cys Ala Gly Phe Leu Gln Gly Asn Val
            180                 185                 190

Asp Ser Cys Gln Gly Asp Ser Gly Gly Pro Leu Val Thr Ser Asn Asn
        195                 200                 205

Asn Ile Trp Trp Leu Ile Gly Asp Thr Ser Trp Gly Ser Gly Cys Ala
    210                 215                 220

Lys Ala Tyr Arg Pro Gly Val Tyr Gly Asn Val Met Val Phe Thr Asp
225                 230                 235                 240

Trp Ile Tyr Arg Gln Met Lys Ala Asn Gly
                245                 250

<210> SEQ ID NO 9
<211> LENGTH: 257
<212> TYPE: PRT
<213> ORGANISM: Homo sapiens

<400> SEQUENCE: 9

Glu Cys Gly Val Pro Thr Leu Ala Arg Pro Glu Thr Arg Ile Val Gly
1               5                   10                  15

Gly Lys Ser Ala Ala Phe Gly Arg Trp Pro Trp Gln Val Ser Val Arg
            20                  25                  30

Arg Thr Ser Phe Phe Gly Phe Ser Ser Thr His Arg Cys Gly Gly Ala
        35                  40                  45
```

-continued

```
Leu Ile Asn Glu Asn Trp Ile Ala Thr Ala Gly His Cys Val Asp Asp
 50                  55                  60

Leu Leu Ile Ser Gln Ile Arg Ile Arg Val Gly Glu Tyr Asp Phe Ser
 65                  70                  75                  80

His Val Gln Glu Gln Leu Pro Tyr Ile Glu Arg Gly Val Ala Lys Lys
                 85                  90                  95

Val Val His Pro Lys Tyr Ser Phe Leu Thr Tyr Glu Tyr Asp Leu Ala
            100                 105                 110

Leu Val Lys Leu Glu Gln Pro Leu Glu Phe Ala Pro His Val Ser Pro
        115                 120                 125

Ile Cys Leu Pro Glu Thr Asp Ser Leu Leu Ile Gly Met Asn Ala Thr
130                 135                 140

Val Thr Gly Trp Gly Arg Leu Ser Glu Gly Gly Thr Leu Pro Ser Val
145                 150                 155                 160

Leu Gln Glu Val Ser Val Pro Ile Val Ser Asn Asp Asn Cys Lys Ser
                165                 170                 175

Met Phe Met Arg Ala Gly Arg Gln Glu Phe Ile Pro Asp Ile Phe Leu
            180                 185                 190

Cys Ala Gly Tyr Glu Thr Gly Gly Gln Asp Ser Cys Gln Gly Asp Ser
        195                 200                 205

Gly Gly Pro Leu Gln Ala Lys Ser Gln Asp Gly Arg Phe Phe Leu Ala
    210                 215                 220

Gly Ile Ile Ser Trp Gly Ile Gly Cys Ala Glu Ala Asn Leu Pro Gly
225                 230                 235                 240

Val Cys Thr Arg Ile Ser Lys Phe Thr Pro Trp Ile Leu Glu His Val
                245                 250                 255

Arg

<210> SEQ ID NO 10
<211> LENGTH: 259
<212> TYPE: PRT
<213> ORGANISM: Homo sapiens

<400> SEQUENCE: 10

Asp Cys Gly Arg Arg Lys Leu Pro Val Asp Arg Ile Val Gly Gly Arg
 1               5                  10                  15

Asp Thr Ser Leu Gly Arg Trp Pro Trp Gln Val Ser Leu Arg Tyr Asp
                 20                  25                  30

Gly Ala His Leu Cys Gly Gly Ser Leu Leu Ser Gly Asp Trp Val Leu
             35                  40                  45

Thr Ala Ala His Cys Phe Pro Glu Arg Asn Arg Val Leu Ser Arg Trp
 50                  55                  60

Arg Val Phe Ala Gly Ala Val Ala Gln Ala Ser Pro His Gly Leu Gln
 65                  70                  75                  80

Leu Gly Val Gln Ala Val Val Tyr His Gly Gly Tyr Leu Pro Phe Arg
                 85                  90                  95

Asp Pro Asn Ser Glu Glu Asn Ser Asn Asp Ile Ala Leu Val His Leu
            100                 105                 110

Ser Ser Pro Leu Pro Leu Thr Glu Tyr Ile Gln Pro Val Cys Leu Pro
        115                 120                 125

Ala Ala Gly Gln Ala Leu Val Asp Gly Lys Ile Cys Thr Val Thr Gly
    130                 135                 140

Trp Gly Asn Thr Gln Tyr Tyr Gly Gln Gln Ala Gly Val Leu Gln Glu
145                 150                 155                 160
```

```
Ala Arg Val Pro Ile Ile Ser Asn Asp Val Cys Asn Gly Ala Asp Phe
            165                 170                 175

Tyr Gly Asn Gln Ile Lys Pro Lys Met Phe Cys Ala Gly Tyr Pro Glu
            180                 185                 190

Gly Gly Ile Asp Ala Cys Gln Gly Asp Ser Gly Gly Pro Phe Val Cys
            195                 200                 205

Glu Asp Ser Ile Ser Arg Thr Pro Arg Trp Arg Leu Cys Gly Ile Val
210                 215                 220

Ser Trp Gly Thr Gly Cys Ala Leu Ala Gln Lys Pro Gly Val Tyr Thr
225                 230                 235                 240

Lys Val Ser Asp Phe Arg Glu Trp Ile Phe Gln Ala Ile Lys Thr His
            245                 250                 255

Ser Glu Ala

<210> SEQ ID NO 11
<211> LENGTH: 247
<212> TYPE: PRT
<213> ORGANISM: Homo sapiens

<400> SEQUENCE: 11

Glu Cys Thr Thr Lys Ile Lys Pro Arg Ile Val Gly Gly Thr Ala Ser
  1               5                  10                  15

Val Arg Gly Glu Trp Pro Trp Gln Val Thr Leu His Thr Thr Ser Pro
             20                  25                  30

Thr Gln Arg His Leu Cys Gly Gly Ser Ile Ile Gly Asn Gln Trp Ile
         35                  40                  45

Leu Thr Ala Ala His Cys Phe Tyr Gly Val Glu Ser Pro Lys Ile Leu
     50                  55                  60

Arg Val Tyr Ser Gly Ile Leu Asn Gln Ser Glu Ile Lys Glu Asp Thr
 65                  70                  75                  80

Ser Phe Phe Gly Val Gln Glu Ile Ile Ile His Asp Gln Tyr Lys Met
                 85                  90                  95

Ala Glu Ser Gly Tyr Asp Ile Ala Leu Leu Lys Leu Glu Thr Thr Val
            100                 105                 110

Asn Tyr Thr Asp Ser Gln Arg Pro Ile Cys Leu Pro Ser Lys Gly Asp
        115                 120                 125

Arg Asn Val Ile Tyr Thr Asp Cys Trp Val Thr Gly Trp Gly Tyr Arg
    130                 135                 140

Lys Leu Arg Asp Lys Ile Gln Asp Thr Leu Gln Lys Ala Lys Ile Pro
145                 150                 155                 160

Leu Val Thr Asn Glu Glu Cys Gln Lys Arg Tyr Arg Gly His Lys Ile
            165                 170                 175

Thr His Lys Met Ile Cys Ala Gly Tyr Arg Glu Gly Gly Lys Asp Ala
        180                 185                 190

Cys Lys Gly Asp Ser Gly Gly Pro Leu Ser Cys Lys His Asn Glu Val
    195                 200                 205

Trp His Leu Val Gly Ile Thr Ser Trp Gly Glu Gly Cys Ala Gln Arg
210                 215                 220

Glu Arg Pro Gly Val Tyr Thr Asn Val Val Glu Tyr Val Asp Trp Ile
225                 230                 235                 240

Leu Glu Lys Thr Gln Ala Val
            245

<210> SEQ ID NO 12
<211> LENGTH: 244
```

```
<212> TYPE: PRT
<213> ORGANISM: Homo sapiens

<400> SEQUENCE: 12

Asp Cys Gly Lys Pro Gln Val Glu Pro Lys Cys Pro Gly Arg Val
1               5                   10                  15

Val Gly Gly Cys Val Ala His Pro His Ser Trp Pro Trp Gln Val Ser
            20                  25                  30

Leu Arg Thr Arg Phe Gly Met His Phe Cys Gly Gly Thr Leu Ile Ser
        35                  40                  45

Pro Glu Trp Val Leu Thr Ala Ala His Cys Leu Glu Lys Ser Pro Arg
50                  55                  60

Pro Ser Ser Tyr Lys Val Ile Leu Gly Ala His Gln Glu Val Asn Leu
65                  70                  75                  80

Glu Pro His Val Gln Glu Ile Glu Val Ser Arg Leu Phe Leu Glu Pro
                85                  90                  95

Thr Arg Lys Asp Ile Ala Leu Leu Lys Leu Ser Ser Pro Ala Val Ile
            100                 105                 110

Thr Asp Lys Val Ile Pro Ala Cys Leu Pro Ser Pro Asn Tyr Val Val
        115                 120                 125

Ala Asp Arg Thr Glu Cys Phe Ile Thr Gly Trp Gly Glu Thr Gln Gly
130                 135                 140

Thr Phe Gly Ala Gly Leu Leu Glu Ala Gln Leu Pro Val Ile Glu Asn
145                 150                 155                 160

Lys Val Cys Asn Arg Tyr Glu Phe Leu Asn Gly Arg Val Gln Ser Thr
                165                 170                 175

Glu Leu Cys Ala Gly His Leu Ala Gly Gly Thr Asp Ser Cys Gln Gly
            180                 185                 190

Asp Ser Gly Gly Pro Leu Val Cys Phe Glu Lys Asp Lys Tyr Ile Leu
        195                 200                 205

Gln Gly Val Thr Ser Trp Gly Leu Gly Cys Ala Arg Pro Asn Lys Pro
210                 215                 220

Gly Val Tyr Val Arg Val Ser Arg Phe Val Thr Trp Ile Glu Gly Val
225                 230                 235                 240

Met Arg Asn Asn

<210> SEQ ID NO 13
<211> LENGTH: 234
<212> TYPE: PRT
<213> ORGANISM: Homo sapiens

<400> SEQUENCE: 13

Val Ala Ala Pro Phe Asp Asp Asp Lys Ile Val Gly Gly Tyr Ile
1               5                   10                  15

Cys Glu Glu Asn Ser Val Pro Tyr Gln Val Ser Leu Asn Ser Gly Tyr
            20                  25                  30

His Phe Cys Gly Gly Ser Leu Ile Ser Glu Gln Trp Val Val Ser Ala
        35                  40                  45

Gly His Cys Tyr Lys Ser Arg Ile Gln Val Arg Leu Gly Glu His Asn
50                  55                  60

Ile Glu Val Leu Glu Gly Asn Glu Gln Phe Ile Asn Ala Ala Lys Ile
65                  70                  75                  80

Ile Arg His Pro Lys Tyr Asn Ser Arg Thr Leu Asp Asn Asp Ile Leu
                85                  90                  95

Leu Ile Lys Leu Ser Ser Pro Ala Val Ile Asn Ser Arg Val Ser Ala
```

```
                100                 105                 110
Ile Ser Leu Pro Thr Ala Pro Ala Ala Gly Thr Glu Ser Leu Ile
            115                 120                 125

Ser Gly Trp Gly Asn Thr Leu Ser Ser Gly Ala Asp Tyr Pro Asp Glu
    130                 135                 140

Leu Gln Cys Leu Asp Ala Pro Val Leu Ser Gln Ala Glu Cys Glu Ala
145                 150                 155                 160

Ser Tyr Pro Gly Lys Ile Thr Asn Asn Met Phe Cys Val Gly Phe Leu
                165                 170                 175

Glu Gly Gly Lys Asp Ser Cys Gln Gly Asp Ser Gly Gly Pro Val Val
            180                 185                 190

Ser Asn Gly Glu Leu Gln Gly Ile Val Ser Trp Gly Tyr Gly Cys Ala
        195                 200                 205

Gln Lys Asn Arg Pro Gly Val Tyr Thr Lys Val Tyr Asn Tyr Val Asp
    210                 215                 220

Trp Ile Lys Asp Thr Ile Ala Ala Asn Ser
225                 230

<210> SEQ ID NO 14
<211> LENGTH: 240
<212> TYPE: PRT
<213> ORGANISM: Homo sapiens

<400> SEQUENCE: 14

Ile His Pro Val Leu Ser Gly Leu Ser Arg Ile Val Asn Gly Glu Asp
 1               5                  10                  15

Ala Val Pro Gly Ser Trp Pro Trp Gln Val Ser Leu Gln Asp Lys Thr
                20                  25                  30

Gly Phe His Phe Cys Gly Gly Ser Leu Ile Ser Glu Asp Trp Val Val
            35                  40                  45

Thr Ala Ala His Cys Gly Val Arg Thr Ser Asp Val Val Val Ala Gly
        50                  55                  60

Glu Phe Asp Gln Gly Ser Asp Glu Glu Asn Ile Gln Val Leu Lys Ile
65                  70                  75                  80

Ala Lys Val Phe Lys Asn Pro Lys Phe Ser Ile Leu Thr Val Asn Asn
                85                  90                  95

Asp Ile Thr Leu Leu Lys Leu Ala Thr Pro Ala Arg Phe Ser Gln Thr
                100                 105                 110

Val Ser Ala Val Cys Leu Pro Ser Ala Asp Asp Phe Pro Ala Gly
            115                 120                 125

Thr Leu Cys Ala Thr Thr Gly Trp Gly Lys Thr Lys Tyr Asn Ala Asn
    130                 135                 140

Lys Thr Pro Asp Lys Leu Gln Gln Ala Ala Leu Pro Leu Leu Ser Asn
145                 150                 155                 160

Ala Glu Cys Lys Lys Ser Trp Gly Arg Arg Ile Thr Asp Val Asn Ile
                165                 170                 175

Cys Ala Gly Ala Ser Gly Val Ser Ser Cys Met Gly Asp Ser Gly Gly
            180                 185                 190

Pro Leu Val Cys Gln Lys Asp Gly Ala Trp Thr Leu Val Gly Ile Val
        195                 200                 205

Ser Trp Gly Ser Asp Thr Cys Ser Thr Ser Pro Gly Val Tyr Ala
    210                 215                 220

Arg Val Thr Lys Leu Ile Pro Trp Val Gln Lys Ile Leu Ala Ala Asn
225                 230                 235                 240
```

```
<210> SEQ ID NO 15
<211> LENGTH: 145
<212> TYPE: PRT
<213> ORGANISM: Homo sapiens

<400> SEQUENCE: 15

Pro Cys Pro Gly Gln Phe Thr Cys Arg Thr Gly Arg Cys Ile Arg Lys
  1               5                  10                  15

Glu Leu Arg Cys Asp Gly Trp Ala Asp Cys Thr Asp His Ser Asp Glu
             20                  25                  30

Leu Asn Cys Ser Cys Asp Ala Gly His Gln Phe Thr Cys Lys Asn Lys
         35                  40                  45

Phe Cys Lys Pro Leu Phe Trp Val Cys Asp Ser Val Asn Asp Cys Gly
     50                  55                  60

Asp Asn Ser Asp Glu Gln Gly Ser Ser Cys Pro Ala Gln Thr Phe Arg
 65                  70                  75                  80

Cys Ser Asn Gly Lys Cys Leu Ser Lys Ser Gln Gln Cys Asn Gly Lys
                 85                  90                  95

Asp Asp Cys Gly Asp Gly Ser Asp Glu Ala Ser Cys Thr Cys Thr Lys
            100                 105                 110

His Thr Tyr Arg Cys Leu Asn Gly Leu Cys Leu Ser Lys Gly Asn Pro
        115                 120                 125

Glu Cys Asp Gly Lys Glu Asp Cys Ser Asp Gly Ser Asp Glu Lys Asp
    130                 135                 140

Cys
145

<210> SEQ ID NO 16
<211> LENGTH: 19
<212> TYPE: PRT
<213> ORGANISM: Homo sapiens

<400> SEQUENCE: 16

Thr Cys Glu Phe Cys Gly Cys Ile Trp Cys Asp Asp Cys Asp Gly Ser
  1               5                  10                  15

Asp Glu Cys

<210> SEQ ID NO 17
<211> LENGTH: 18
<212> TYPE: PRT
<213> ORGANISM: Homo sapiens

<400> SEQUENCE: 17

Cys Phe Cys Arg Cys Ile Pro Trp Cys Asp Gly Asp Cys Asp Ser Asp
  1               5                  10                  15

Glu Cys

<210> SEQ ID NO 18
<211> LENGTH: 16
<212> TYPE: PRT
<213> ORGANISM: Homo sapiens

<400> SEQUENCE: 18

Pro Cys Pro Glu Phe Cys Cys Asp Asp Cys Asp Ser Asp Glu Cys
  1               5                  10                  15

<210> SEQ ID NO 19
<211> LENGTH: 16
<212> TYPE: PRT
```

```
<213> ORGANISM: Homo sapiens

<400> SEQUENCE: 19

Cys Phe Cys Cys Ile Cys Asp Gly Asp Cys Asp Gly Ser Asp Glu Cys
 1               5                  10                  15

<210> SEQ ID NO 20
<211> LENGTH: 114
<212> TYPE: PRT
<213> ORGANISM: Homo sapiens

<400> SEQUENCE: 20

Cys Ser Phe Gly Leu His Ala Arg Gly Val Glu Leu Met Arg Phe Thr
 1               5                  10                  15

Thr Pro Gly Phe Pro Asp Ser Pro Tyr Pro Ala His Ala Arg Cys Gln
             20                  25                  30

Trp Ala Leu Arg Gly Asp Ala Asp Ser Val Leu Ser Leu Thr Phe Arg
         35                  40                  45

Ser Phe Asp Leu Ala Ser Cys Asp Glu Arg Gly Ser Asp Leu Val Thr
     50                  55                  60

Val Tyr Asn Thr Leu Ser Pro Met Glu Pro His Ala Leu Val Gln Leu
 65                  70                  75                  80

Cys Gly Thr Tyr Pro Pro Ser Tyr Asn Leu Thr Phe His Ser Ser Gln
                 85                  90                  95

Asn Val Leu Leu Ile Thr Leu Ile Thr Asn Thr Glu Arg Arg His Pro
            100                 105                 110

Gly Phe

<210> SEQ ID NO 21
<211> LENGTH: 101
<212> TYPE: PRT
<213> ORGANISM: Homo sapiens

<400> SEQUENCE: 21

Cys Gly Gly Arg Leu Arg Lys Ala Gln Gly Thr Phe Asn Ser Pro Tyr
 1               5                  10                  15

Tyr Pro Gly His Tyr Pro Pro Asn Ile Asp Cys Thr Trp Asn Ile Glu
             20                  25                  30

Val Pro Asn Asn Gln His Val Lys Val Arg Phe Lys Phe Phe Tyr Leu
         35                  40                  45

Leu Glu Pro Gly Val Pro Ala Gly Thr Cys Pro Lys Asp Tyr Val Glu
     50                  55                  60

Ile Asn Gly Glu Lys Tyr Cys Gly Glu Arg Ser Gln Phe Val Val Thr
 65                  70                  75                  80

Ser Asn Ser Asn Lys Ile Thr Val Arg Phe His Ser Asp Gln Ser Tyr
                 85                  90                  95

Thr Asp Thr Gly Phe
            100

<210> SEQ ID NO 22
<211> LENGTH: 106
<212> TYPE: PRT
<213> ORGANISM: Homo sapiens

<400> SEQUENCE: 22

Cys Ser Ser Glu Leu Tyr Thr Glu Ala Ser Gly Tyr Ile Ser Ser Leu
 1               5                  10                  15

Glu Tyr Pro Arg Ser Tyr Pro Pro Asp Leu Arg Cys Asn Tyr Ser Ile
```

-continued

```
                20                  25                  30
Arg Val Glu Arg Gly Leu Thr Leu His Leu Lys Phe Leu Glu Pro Phe
         35                  40                  45
Asp Ile Asp Asp His Gln Gln Val His Cys Pro Tyr Asp Gln Leu Gln
     50                  55                  60
Ile Tyr Ala Asn Gly Lys Asn Ile Gly Glu Phe Cys Gly Lys Gln Arg
 65                  70                  75                  80
Pro Pro Asp Leu Asp Thr Ser Ser Asn Ala Val Asp Leu Leu Phe Phe
                 85                  90                  95
Thr Asp Glu Ser Gly Asp Ser Arg Gly Trp
            100                 105
```

<210> SEQ ID NO 23
<211> LENGTH: 109
<212> TYPE: PRT
<213> ORGANISM: Homo sapiens

<400> SEQUENCE: 23

```
Cys Ser Gly Asp Val Phe Thr Ala Leu Ile Gly Glu Ile Ala Ser Pro
  1               5                  10                  15
Asn Tyr Pro Lys Pro Tyr Pro Glu Asn Ser Arg Cys Glu Tyr Gln Ile
             20                  25                  30
Arg Leu Glu Lys Gly Phe Gln Val Val Thr Leu Arg Arg Glu Asp
         35                  40                  45
Phe Asp Val Glu Ala Ala Asp Ser Ala Gly Asn Cys Leu Asp Ser Leu
     50                  55                  60
Val Phe Val Ala Gly Asp Arg Gln Phe Gly Pro Tyr Cys Gly His Gly
 65                  70                  75                  80
Phe Pro Gly Pro Leu Asn Ile Glu Thr Lys Ser Asn Ala Leu Asp Ile
                 85                  90                  95
Ile Phe Gln Thr Asp Leu Thr Gly Gln Lys Lys Gly Trp
            100                 105
```

<210> SEQ ID NO 24
<211> LENGTH: 106
<212> TYPE: PRT
<213> ORGANISM: Homo sapiens

<400> SEQUENCE: 24

```
Cys Ser Asp Asn Leu Phe Thr Gln Arg Thr Gly Val Ile Thr Ser Pro
  1               5                  10                  15
Asp Phe Pro Asn Pro Tyr Pro Lys Ser Ser Glu Cys Leu Tyr Thr Ile
             20                  25                  30
Glu Leu Glu Glu Gly Phe Met Val Asn Leu Gln Phe Glu Asp Ile Phe
         35                  40                  45
Asp Ile Glu Asp His Pro Glu Val Pro Cys Pro Tyr Asp Tyr Ile Lys
     50                  55                  60
Ile Lys Val Gly Pro Lys Val Leu Gly Pro Phe Cys Gly Glu Lys Ala
 65                  70                  75                  80
Pro Glu Pro Ile Ser Thr Gln Ser His Ser Val Leu Ile Leu Phe His
                 85                  90                  95
Ser Asp Asn Ser Gly Glu Asn Arg Gly Trp
            100                 105
```

<210> SEQ ID NO 25
<211> LENGTH: 109
<212> TYPE: PRT

<213> ORGANISM: Homo sapiens

<400> SEQUENCE: 25

```
Cys Ser Gly Asp Val Phe Thr Ala Leu Ile Gly Glu Ile Ala Ser Pro
  1               5                  10                  15

Asn Tyr Pro Lys Pro Tyr Pro Glu Asn Ser Arg Cys Glu Tyr Gln Ile
             20                  25                  30

Arg Leu Glu Lys Gly Phe Gln Val Val Val Thr Leu Arg Arg Glu Asp
         35                  40                  45

Phe Asp Val Glu Ala Ala Asp Ser Ala Gly Asn Cys Gln Asp Ser Leu
     50                  55                  60

Leu Phe Ala Ala Lys Asn Arg Gln Phe Gly Pro Phe Cys Gly Asn Gly
 65                  70                  75                  80

Phe Pro Gly Pro Leu Thr Ile Glu Thr His Ser Asn Thr Leu Asp Ile
                 85                  90                  95

Val Phe Gln Thr Asp Leu Thr Glu Gln Lys Lys Gly Trp
            100                 105
```

<210> SEQ ID NO 26
<211> LENGTH: 3149
<212> TYPE: DNA
<213> ORGANISM: Homo sapiens

<400> SEQUENCE: 26

| | | | | | | |
|---|---|---|---|---|---|---|
| gacgcctgtg | agacccgcga | gcggcctcgg | ggaccatggg | gagcgatcgg | gcccgcaagg | 60 |
| gcggaggggg | cccgaaggac | ttcggcgcgg | gactcaagta | caactcccgg | cacgagaaag | 120 |
| tgaatggctt | ggaggaaggc | gtggagttcc | tgccagtcaa | caacgtcaag | aaggtggaaa | 180 |
| agcatggccc | ggggcgctgg | gtggtgctgg | cagccgtgct | gatcggcctc | ctcttggtct | 240 |
| tgctggggat | cggcttcctg | gtgtggcatt | tgcagtaccg | ggacgtgcgt | gtccagaagg | 300 |
| tcttcaatgg | ctacatgagg | atcacaaatg | agaattttgt | ggatgcctac | gagaactcca | 360 |
| actccactga | gtttgtaagc | ctggccagca | aggtgaagga | cgcgctgaag | ctgctgtaca | 420 |
| gcggagtccc | attcctgggc | cctaccacca | aggagtcggc | tgtgacggcc | ttcagcgagg | 480 |
| gcagcgtcat | cgcctactac | tggtctgagt | tcagcatccc | gcagcacctg | gtggaggagg | 540 |
| ccgagcgcgt | catggccgag | gagcgcgtag | tcatgctgcc | ccgcggggcg | cgctccctga | 600 |
| agtcctttgt | ggtcacctca | gtggtggctt | ccccacggga | ctccaaaaca | gtacagagga | 660 |
| cccaggacaa | cagctgcagc | tttggcctgc | acgcccgcgg | tgtggagctg | atgcgcttca | 720 |
| ccacgcccgg | cttccctgac | agcccctacc | ccgctcatgc | ccgctgccag | tgggccctgc | 780 |
| gggggggacgc | cgactcagtg | ctgagcctca | ccttccgcag | cttttgacctt | gcgtcctgcg | 840 |
| acgagcgcgg | cagcgacctg | gtgacggtgt | acaacacccct | gagccccatg | gagccccacg | 900 |
| ccctggtgca | gttgtgtggc | acctacccctc | cctcctacaa | cctgaccttc | cactcctccc | 960 |
| agaacgtcct | gctcatcaca | ctgataacca | acactgagcg | gcggcatccc | ggctttgagg | 1020 |
| ccaccttctt | ccagctgcct | aggatgagca | gctgtggagg | ccgcttacgt | aaagcccagg | 1080 |
| ggacattcaa | cagcccctac | tacccaggcc | actacccacc | caacattgac | tgcacatgga | 1140 |
| acattgaggt | gccaacaac | cagcatgtga | aggtgcgctt | caattcttc | tacctgctgg | 1200 |
| agcccggcgt | gcctgcgggc | acctgcccca | aggactacgt | ggagatcaat | ggggagaaat | 1260 |
| actgcggaga | gaggtcccag | ttcgtcgtca | ccagcaacag | caacaagatc | acagttcgct | 1320 |
| tccactcaga | tcagtcctac | accgacaccg | gcttcttagc | tgaataccctc | tcctacgact | 1380 |

```
ccagtgaccc atgcccgggg cagttcacgt gccgcacggg gcggtgtatc cggaaggagc   1440
tgcgctgtga tggctgggcc gactgcaccg accacagcga tgagctcaac tgcagttgcg   1500
acgccggcca ccagttcacg tgcaagaaca agttctgcaa gcccctcttc tgggtctgcg   1560
acagtgtgaa cgactgcgga gacaacagcg acgagcaggg gtgcagttgt ccggcccaga   1620
ccttcaggtg ttccaatggg aagtgcctct cgaaaagcca gcagtgcaat gggaaggacg   1680
actgtgggga cgggtccgac gaggcctcct gccccaaggt gaacgtcgtc acttgtacca   1740
aacacaccta ccgctgcctc aatgggctct gcttgagcaa gggcaaccct gagtgtgacg   1800
ggaaggagga ctgtagcgac ggctcagatg agaaggactg cgactgtggg ctgcggtcat   1860
tcacgagaca ggctcgtgtt gttggggca cggatgcgga tgagggcgag tggccctggc   1920
aggtaagcct gcatgctctg gccagggcc acatctgcgg tgcttccctc atctctccca   1980
actggctggt ctctgccgca cactgctaca tcgatgacag aggattcagg tactcagacc   2040
ccacgcagtg gacggccttc ctgggcttgc acgaccagag ccagcgcagc gcccctgggg   2100
tgcaggagcg caggctcaag cgcatcatct cccaccccct tcttcaatgac ttcaccttcg   2160
actatgacat cgcgctgctg gagctggaga accggcaga gtacagctcc atggtgcggc   2220
ccatctgcct gccggacgcc tcccatgtct ccctgccgg caaggccatc tgggtcacgg   2280
gctgggaca cacccagtat ggaggcactg gcgcgctgat cctgcaaaag ggtgagatcc   2340
gcgtcatcaa ccagaccacc tgcgagaacc tcctgccgca gcagatcacg ccgcgcatga   2400
tgtgcgtggg cttcctcagc ggcggcgtgg actcctgcca gggtgattcc ggggggacccc   2460
tgtccagcgt ggaggcggat gggcggatct tccaggccgg tgtggtgagc tggggagacg   2520
gctgcgctca gaggaacaag ccaggcgtgt acacaaggct ccctctgttt cgggactgga   2580
tcaaagagaa cactggggta tagggccgg ggccacccaa atgtgtacac ctgcggggcc   2640
acccatcgtc caccccagtg tgcacgcctg caggctggag actggaccgc tgactgcacc   2700
agcgccccca gaacatacac tgtgaactca atctccaggg ctccaaatct gcctagaaaa   2760
cctctcgctt cctcagcctc caaagtggag ctgggaggta aaggggagg acactggtgg   2820
ttctactgac ccaactgggg gcaaaggttt gaagacacag cctccccgc cagccccaag   2880
ctgggccgag gcgcgtttgt gtatatctgc ctcccctgtc tgtaaggagc agcgggaacg   2940
gagcttcgga gcctcctcag tgaaggtggt ggggctgccg gatctgggct gtggggccct   3000
tgggccacgc tcttgaggaa gcccaggctc ggaggaccct ggaaaacaga cgggtctgag   3060
actgaaaatg gtttaccagc tcccaggtga cttcagtgtg tgtattgtgt aaatgagtaa   3120
aacatttat ttcttttaa aaaaaaaa                                        3149
```

<210> SEQ ID NO 27
<211> LENGTH: 855
<212> TYPE: PRT
<213> ORGANISM: Homo sapiens

<400> SEQUENCE: 27

Met Gly Ser Asp Arg Ala Arg Lys Gly Gly Gly Pro Lys Asp Phe
1               5                   10                  15

Gly Ala Gly Leu Lys Tyr Asn Ser Arg His Glu Lys Val Asn Gly Leu
            20                  25                  30

Glu Glu Gly Val Glu Phe Leu Pro Val Asn Asn Val Lys Lys Val Glu
        35                  40                  45

Lys His Gly Pro Gly Arg Trp Val Val Leu Ala Ala Val Leu Ile Gly
    50                  55                  60

```
Leu Leu Leu Val Leu Leu Gly Ile Gly Phe Leu Val Trp His Leu Gln
 65                  70                  75                  80

Tyr Arg Asp Val Arg Val Gln Lys Val Lys Asn Gly Tyr Met Arg Ile
                 85                  90                  95

Thr Asn Glu Asn Phe Val Asp Ala Tyr Glu Asn Ser Asn Ser Thr Glu
            100                 105                 110

Phe Val Ser Leu Ala Ser Lys Val Lys Asp Ala Leu Lys Leu Leu Tyr
        115                 120                 125

Ser Gly Val Pro Phe Leu Gly Pro Tyr His Lys Glu Ser Ala Val Thr
130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
            180                 185                 190

Val Thr Ser Val Val Ala Phe Pro Thr Asp Ser Lys Thr Val Gln Arg
        195                 200                 205

Thr Gln Asp Asn Ser Cys Ser Phe Gly Leu His Ala Arg Gly Val Glu
210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
            260                 265                 270

Ser Asp Leu Val Thr Val Tyr Asn Thr Leu Ser Pro Met Glu Pro His
        275                 280                 285

Ala Leu Val Gln Leu Cys Gly Thr Tyr Pro Pro Ser Tyr Asn Leu Thr
290                 295                 300

Phe His Ser Ser Gln Asn Val Leu Leu Ile Thr Leu Ile Thr Asn Thr
305                 310                 315                 320

Glu Arg Arg His Pro Gly Phe Glu Ala Thr Phe Phe Gln Leu Pro Arg
                325                 330                 335

Met Ser Ser Cys Gly Gly Arg Leu Arg Lys Ala Gln Gly Thr Phe Asn
            340                 345                 350

Ser Pro Tyr Tyr Pro Gly His Tyr Pro Pro Asn Ile Asp Cys Thr Trp
        355                 360                 365

Asn Ile Glu Val Pro Asn Asn Gln His Val Lys Val Arg Phe Lys Phe
370                 375                 380

Phe Tyr Leu Leu Glu Pro Gly Val Pro Ala Gly Thr Cys Pro Lys Asp
385                 390                 395                 400

Tyr Val Glu Ile Asn Gly Glu Lys Tyr Cys Gly Glu Arg Ser Gln Phe
                405                 410                 415

Val Val Thr Ser Asn Ser Asn Lys Ile Thr Val Arg Phe His Ser Asp
            420                 425                 430

Gln Ser Tyr Thr Asp Thr Gly Phe Leu Ala Glu Tyr Leu Ser Tyr Asp
        435                 440                 445

Ser Ser Asp Pro Cys Pro Gly Gln Phe Thr Cys Arg Thr Gly Arg Cys
450                 455                 460

Ile Arg Lys Glu Leu Arg Cys Asp Gly Trp Ala Asp Cys Thr Asp His
465                 470                 475                 480
```

```
Ser Asp Glu Leu Asn Cys Ser Cys Asp Ala Gly His Gln Phe Thr Cys
            485                 490                 495

Lys Asn Lys Phe Cys Lys Pro Leu Phe Trp Val Cys Asp Ser Val Asn
        500                 505                 510

Asp Cys Gly Asp Asn Ser Asp Glu Gln Gly Cys Ser Cys Pro Ala Gln
            515                 520                 525

Thr Phe Arg Cys Ser Asn Gly Lys Cys Leu Ser Lys Ser Gln Gln Cys
        530                 535                 540

Asn Gly Lys Asp Asp Cys Gly Asp Gly Ser Asp Glu Ala Ser Cys Pro
545                 550                 555                 560

Lys Val Asn Val Val Thr Cys Thr Lys His Thr Tyr Arg Cys Leu Asn
                565                 570                 575

Gly Leu Cys Leu Ser Lys Gly Asn Pro Glu Cys Asp Gly Lys Glu Asp
            580                 585                 590

Cys Ser Asp Gly Ser Asp Glu Lys Asp Cys Asp Cys Gly Leu Arg Ser
            595                 600                 605

Phe Thr Arg Gln Ala Arg Val Val Gly Gly Thr Asp Ala Asp Glu Gly
        610                 615                 620

Glu Trp Pro Trp Gln Val Ser Leu His Ala Leu Gly Gln Gly His Ile
625                 630                 635                 640

Cys Gly Ala Ser Leu Ile Ser Pro Asn Trp Leu Val Ser Ala Ala His
                645                 650                 655

Cys Tyr Ile Asp Asp Arg Gly Phe Arg Tyr Ser Asp Pro Thr Gln Trp
            660                 665                 670

Thr Ala Phe Leu Gly Leu His Asp Gln Ser Gln Arg Ser Ala Pro Gly
        675                 680                 685

Val Gln Glu Arg Arg Leu Lys Arg Ile Ile Ser His Pro Phe Phe Asn
        690                 695                 700

Asp Phe Thr Phe Asp Tyr Asp Ile Ala Leu Leu Glu Leu Glu Lys Pro
705                 710                 715                 720

Ala Glu Tyr Ser Ser Met Val Arg Pro Ile Cys Leu Pro Asp Ala Ser
                725                 730                 735

His Val Phe Pro Ala Gly Lys Ala Ile Trp Val Thr Gly Trp Gly His
            740                 745                 750

Thr Gln Tyr Gly Gly Thr Gly Ala Leu Ile Leu Gln Lys Gly Glu Ile
        755                 760                 765

Arg Val Ile Asn Gln Thr Thr Cys Glu Asn Leu Leu Pro Gln Gln Ile
        770                 775                 780

Thr Pro Arg Met Met Cys Val Gly Phe Leu Ser Gly Gly Val Asp Ser
785                 790                 795                 800

Cys Gln Gly Asp Ser Gly Gly Pro Leu Ser Ser Val Glu Ala Asp Gly
            805                 810                 815

Arg Ile Phe Gly Ala Gly Val Val Ser Trp Gly Asp Gly Cys Ala Gly
            820                 825                 830

Arg Asn Lys Pro Gly Val Tyr Thr Arg Leu Pro Leu Phe Arg Asp Trp
        835                 840                 845

Ile Lys Glu Asn Thr Gly Val
        850                 855

<210> SEQ ID NO 28
<211> LENGTH: 20
<212> TYPE: DNA
<213> ORGANISM: Homo sapiens

<400> SEQUENCE: 28
```

```
ggcccgcgct ctgaaggtga                                              20

<210> SEQ ID NO 29
<211> LENGTH: 20
<212> TYPE: DNA
<213> ORGANISM: Homo sapiens

<400> SEQUENCE: 29
ttggcaagca ggaagcaggg                                              20

<210> SEQ ID NO 30
<211> LENGTH: 22
<212> TYPE: DNA
<213> ORGANISM: Homo sapiens

<400> SEQUENCE: 30
cctcctcttg gtcttgctgg gg                                           22

<210> SEQ ID NO 31
<211> LENGTH: 20
<212> TYPE: DNA
<213> ORGANISM: Homo sapiens

<400> SEQUENCE: 31
agacccgtct gttttccagg                                              20

<210> SEQ ID NO 32
<211> LENGTH: 11
<212> TYPE: PRT
<213> ORGANISM: Homo sapiens

<400> SEQUENCE: 32

Val Val Gly Gly Thr Asp Ala Asp Glu Gly Glu
 1               5                   10

<210> SEQ ID NO 33
<211> LENGTH: 9
<212> TYPE: PRT
<213> ORGANISM: Homo sapiens

<400> SEQUENCE: 33

Asp Tyr Val Glu Ile Asn Gly Glu Lys
 1               5

<210> SEQ ID NO 34
<211> LENGTH: 5
<212> TYPE: PRT
<213> ORGANISM: Homo sapiens
<220> FEATURE:
<221> NAME/KEY: MOD_RES
<222> LOCATION: (1)
<223> OTHER INFORMATION: Arg or Lys

<400> SEQUENCE: 34

Xaa Val Ile Gly Gly
 1               5

<210> SEQ ID NO 35
<211> LENGTH: 5
<212> TYPE: PRT
<213> ORGANISM: Homo sapiens

<400> SEQUENCE: 35

Arg Val Val Gly Gly
```

```
-continued

<210> SEQ ID NO 36
<211> LENGTH: 5
<212> TYPE: PRT
<213> ORGANISM: Homo sapiens

<400> SEQUENCE: 36

Arg Ile Val Gly Gly
 1               5

<210> SEQ ID NO 37
<211> LENGTH: 13
<212> TYPE: PRT
<213> ORGANISM: Homo sapiens

<400> SEQUENCE: 37

Val Val Gly Gly Thr Asp Ala Asp Glu Gly Glu Trp Pro
 1               5                  10

<210> SEQ ID NO 38
<211> LENGTH: 20
<212> TYPE: PRT
<213> ORGANISM: Homo sapiens

<400> SEQUENCE: 38

Ser Phe Val Val Thr Ser Val Val Ala Phe Pro Thr Asp Ser Lys Thr
 1               5                  10                  15

Val Gln Arg Thr
            20

<210> SEQ ID NO 39
<211> LENGTH: 20
<212> TYPE: PRT
<213> ORGANISM: Homo sapiens

<400> SEQUENCE: 39

Thr Val Gln Arg Thr Gln Asp Asn Ser Cys Ser Phe Gly Leu His Ala
 1               5                  10                  15

Arg Gly Val Glu
            20
```

MATRIPTASE, A SERINE PROTEASE AND ITS APPLICATIONS

RELATED APPLICATIONS

Priority is claimed to International Patent Application No. PCT/US00/06111, filed Mar. 10, 2000, which claims priority to U.S. Provisional Patent Application No. 60/124,006, filed Mar. 12, 1999.

GOVERNMENT RIGHTS

This invention was developed under federally sponsored research projects (e.g., NIH grant Nos. 1R21CA80897, 2P50CA58158 and DOD Grant BC980531), therefore the United States Government may have certain rights in the invention.

FIELD OF THE INVENTION

This invention relates to the field of proteases found in human breast milk and other normal tissue, and to the differentiation of complexation patterns between the proteases and their cognate inhibitors found in normal breast milk, in normal tissues, and incancerous and pre-cancerous tissue of the breast, as well as from other body tissues obtained on biopsy, and in other body fluids such as from nipple aspirate.

BACKGROUND OF THE INVENTION

Serine Proteases and Other Cancer Related Proteases

Elevated proteolytic activity has been implicated in neoplastic progression. While the exact role(s) of proteolytic enzymes in the progression of tumor remains unclear, it seems that proteases may be involved in almost every step of the development and spread of cancer. A widely proposed view is that proteases contribute to the degradation of extracellular matrix (ECM) and to tissue remodeling, and are necessary for cancer invasion and metastasis. A wide array of ECM-degrading proteases has been discovered, the expression of some of which correlates with tumor progression. These include matrix metalloproteases (MMPS) family, plasmin/urokinase type plasminogen activator system and lysosomal proteases cathepsins D and B reviewed by Mignatti et al., *Physiol. Rev.* 73: 161-95 (1993). The plasmin/urokinase type plasminogen activator system is composed of plasmin, the major ECM-degrading protease; the plasminogen activator, uPA; the plasmin inhibitor α2-antiplasmin, the plasminogen activator inhibitors PAI-1 and PAI-2; and the cell membrane receptor for uPA (uPAR) (Andreasen et al., *Int. J. Cancer* 72: 1-22 (1997)). The MMPs are a family of zinc-dependent enzymes with characteristic structures and catalytic properties. The plasmin/urokinase type plasminogen activator system and the 72-kDa gelatinase (MMP-2)/membrane-type MMP system have been received the most attention for their potential roles in the process of invasion of breast cancer and other carcinomas. However, both systems appear to require indirect mechanisms to recruit and activate the major ECM-degrading proteases on the surface of cancer cells. For example, uPA is produced in vivo (Nielson et al., *Lab. Invest.* 74: 168-77 (1996); Pyke et al., *Cancer Res.* 53: 1911-15 (1993); Polette et al., *Virchows Arch.* 424: 641-45 (1994); and Okada et al., *Proc. Natl. Acad. Sci. USA* 92: 2730-34 (1995)) in human breast carcinomas by myofibroblasts adjacent to cancer cells and must diffuse to the cancer cells for receptor-mediated activation and presentation on the surfaces of cancer cells. However, the uPA receptor (uPAR) is detected in macrophages that infiltrate tumor foci in ductal breast cancer. Somewhat analogously, the majority of the MMP family members, such as 72-kDa/Gelatinase A (MMP-2) (Lin et al., *J. Biol. Chem.* 272: 9147-52 (1997)), stromelysin-3 (MMP-11) (Matsudaira, *J. Biol. Chem.* 262: 10035-38 (1987)), MTMMP (MMP-14), are expressed by fibroblastic cells of tumor stroma, or surrounding noncancerous tissues, or both. Indirect mechanisms of activation and recruitment of Gelatinase A in the close vicinity of the surfaces of cancer cells have been proposed, such that an unidentified cancer cell-derived membrane receptor(s) of Gelatinase A could serve as membrane anchor for Gelatinase A; cleaved MT-MMP from stroma cells could then diffuse to the surfaces of cancer cells to activate Gelatinase A. Matrilysin (MMP-7; Pump1) appears to be the only MMP which is found predominantly in the epithelial cells.

The strong origins of these well-characterized extracellular matrix-degrading proteases may suggest that cancer invasion is an event which either depends entirely upon stromal-epithelial cooperation or which is controlled by some other unknown epithelial-derived proteases. Search for these epithelial-derived proteolytic systems that may interact with plasmin/urokinase type plasminogen activator system and/or with MMP family could provide a missing link in our understanding of malignant invasion.

Matriptase was initially identified from T-47D human breast cancer cells as a major gelatinase with a migration rate between those of Gelatinase A (72-kDa, MMP-2) and Gelatinase B (92-kDa, MMP-9). It has been proposed to play a role in the metastatic invasiveness of breast cancer. (See U.S. Pat. No. 5,482,848, which is incorporated herein by reference in its entirety.) The primary cleavage specificity of matriptase was identified to be arginine and lysine residues, similar to the majority of serine proteases, including trypsin and plasmin. In addition, matriptase, like trypsin, exhibits broad spectrum cleavage activity, and such activity is likely to contribute to its gelatinolytic activity. The trypsin-like activity of matriptase distinguishes it from Gelatinases A and B, which may cleave gelatin at glycin residues, the most abundant (almost one third) of amino acid residues in gelatin.

Kunitz-Type Serine Protease Inhibitors

Hepatocyte growth factor (HGF) activator inhibitor-1 (HAI-1) is a Kunitz-type serine protease inhibitor which is able to inhibit HGF activator, a blood coagulation factor XII-like serine protease. The mature form of this protease inhibitor has 478 amino acid residues, with a calculated molecular mass of 53,319. A putative transmembrane domain is located at its carboxyl terminus. HAI-1 contains two Kunitz domains (domain I spans residues 246-306; domain II spans residues 371 to 431) separated by a LDL receptor domain (residues 315 to 360). The presumed P1 residue of active-site cleft is likely to be arginine-260 in Kunitz domain I and lysine 385 in domain II by alignment with bovine pancreatic trypsin inhibitor (BPTI, aprotinin) and with other Kunitz-type inhibitors. Thus, HAI-1 has specificity against trypsin-type proteases. Although HGF activator is exclusively expressed by liver cells, HAI-1 was originally purified from the conditioned media of carcinoma cells as a 40-kDa fragment doublet, rather than the proposed, mature, membrane-bound, 53-kDa form (Shimomura et al., *J. Biol. Chem.* 272: 6370-76 (1997)).

The protein inhibitors of serine proteases can be classified into at least 10 families, according to various schemes. Among them, serpins, such as maspin (Sheng et al., *Proc. Natl. Acad. Sci USA* 93: 11669-74 (1996)) and Kunitz-type inhibitors, such as urinary trypsin inhibitor (Kobayashi et al., *Cancer Res.* 54: 844-49 (1994)) have been previously implicated in suppression of cancer invasion. The Kunitz-type inhibitors form very tight, but reversible complexes with their target serine proteases. The reactive sites of these inhibitors are rigid and can simulate optimal protease substrates. The interaction between a serine protease and a Kunitz-type inhibitor depends on complementary, large surface areas of contact between the protease and inhibitor. The inhibitory activity of the recovered Kunitz-type inhibitor from protease complexes can always be reconstituted. The Kunitz-type inhibitors may be cleaved by cognate proteases, but such cleavage is not essential for their inhibitory activity. In contrast, serpin-type inhibitors also form tight, stable complexes with proteases; in most of cases these complexes are even more stable than those containing Kunitz-type inhibitors. Cleavage of serpins by proteases is necessary for their inhibition, and serpins are always recovered in a cleaved, inactive form from protease reactions. Thus, serpins are considered to be suicide substrate inhibitors, and their inhibitory activity will be lost after encounters with proteases. The suicide nature of serpin inhibitors may result in regulation of proteolytic activity in vivo by direct removal of unwanted proteases via other membrane-bound endocytic receptors (in the case of uPA inhibitors). However, the Kunitz type inhibitors may simply compete with physiological substrates (such as ECM components), and in turn, reduce their availability for proteolysis. These differences may result in different mechanisms whereby these proteases perform their roles in ECM-degradation and cancer invasion.

It has previously been disclosed that a soybean-derived compound known as Bowman-Birk inhibitor (BBI, from Sigma) may have anti-cancer activity by preventing tumor initiation and progression in model systems.

Human milk proteins were fractionated into two pools by addition of ammonium sulfate: a 0-40% pool (A) and a 40-60% pool (B). Both fractions were further purified by DEAE chromatography. The DEAE fractions were examined by immunoblot analysis using mAb 21-9, which is directed against cancer cell-derived matriptase. Two bands of 95- and 110-kDa were detected as indicated; uncomplexed matriptase was not detected. In C, both pooled 110-kDa (lanes 1 and 2) and 95-kDa (lanes 3 and 4) fractions were incubated in 1X SDS sample buffer in the absence of reducing agents at room temperature (–boiling) or at 95° C. (+boiling) for 5 min. prior to SDS-PAGE and subjected to Western blotting using mAb 21-9. The 110-kDa protein had a reduced rate of migration after boiling; however, the 95-kDa protein was converted to uncomplexed matriptase after boiling.

Figure 2:
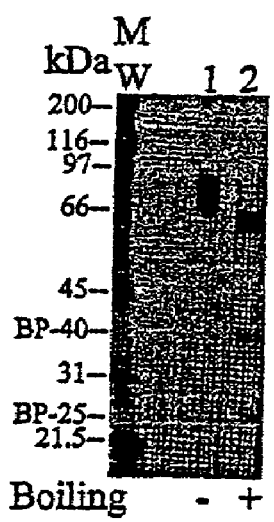

FIG. 2: Immunoaffinity Purification of Matriptase, Complexes

The partially purified matriptase complex from ion-exchange chromatography (see FIG. 1) was loaded onto a mAb 21-9-Sepharose column. The bound proteins were eluted with glycine buffer, pH 2.4, and neutralized by addition of 2 M Trizma. The eluted proteins were incubated in 1×SDS sample buffer in the absence of reducing agents at room temperature (lane 1; –Boiling) or at 95°C. (lane 2; +Boiling) for 5 min. The samples were resolved by SDS-PAGE and stained by colloidal Coomassie. In some batches of purification, as described in the Examples, the 95-kDa matriptase complex was obtained as the major band. This 95-kDa complex was capable of being converted to uncomplexed matriptase and a 40-kDa doublet after boiling. In some other batches, in addition to the 95-kDa complex, a smaller complex with an apparent size of 85-kDa was also obtained (lane 1). This 85-kDa matriptase complex could also be converted to uncompleted matriptase and a 25-kDa band after boiling (lane 2). Molecular mass markers are indicated. BP-40 and BP-25, 40- and 25-kDa binding proteins, respectively.

Figure 3:
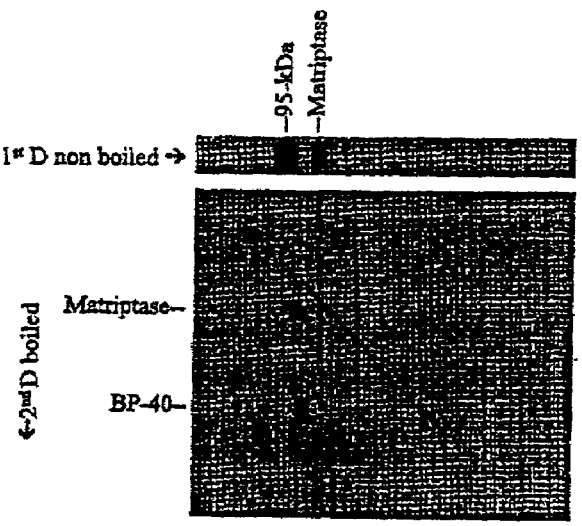

FIG. 3: Diagonal Gel Electrophoresis of the 95-kDa Matriptase Complex Showing Evidence That This Complex Corresponds to the Uncompleted Matriptase in Association With Its 40-kDa Binding Protein Doublet The 95-kDa matriptase complex from human milk was subjected to diagonal gel electrophoresis. In the first dimension (D), the 95-kDa matriptase complex, without boiling treatment, was resolved by SDS-PAGE. Then a gel strip was sliced out, boiled in 1×SDS sample buffer in the absence of reducing agents for 5 min, and electrophoresed on a second SDS-polyacrylamide gel. The proteins were stained by colloidal Coomassie. After this procedure, the 95-kDa matriptase complex disappeared from the diagonal line and was converted to matriptase and a 40-kDa binding protein doublet (BP-40). The uncomplexed matriptase was observed on the diagonal line, as expected, suggesting that is migration rate was not changed by boiling.

Figure 4:
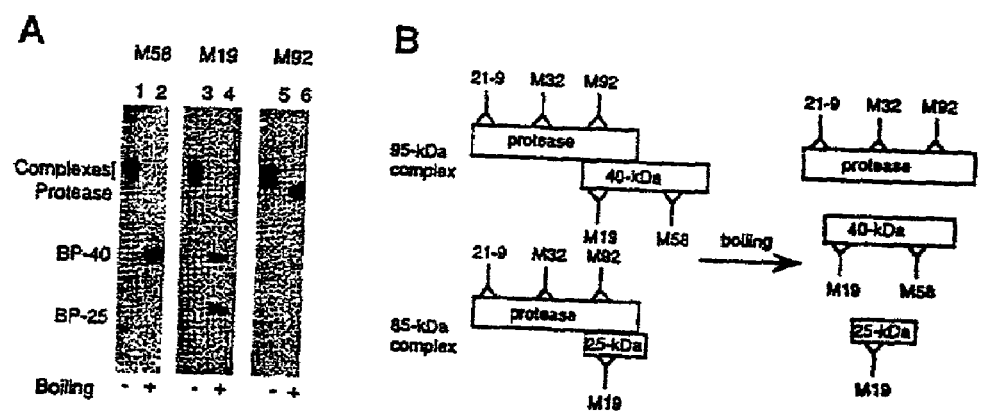

FIG. 4: Structural Characterization of Matriptase Complexes By Monoclonal Antibodies That Are Directed Against The Matriptase and Its Binding Protein A, a pane of mAbs was produced using the milk-derived matriptase complexes as immunogens. These mAbs were characterized by immunoblot analysis using the preparation containing both 95- and 85-kDa matriptase complexes described in the legend to FIG. 2. The matriptase preparation was dissolved in 1×SDS sample buffer in the absence of reducing agents and incubated at room temperature (lanes 1, 3, and 5; –Boiling) or at 95° C. (lanes 2, 4,and 6; +Boiling) for 5 min. Among these mAbs, an anti-matriptase mAb (M92) and two anti-binding protein mAbs (M58 and M19) are presented here. mAb M92 recognized both 95- and 85-kDa matriptase complexes under non-boiling conditions (lane 5 ) and interacted with the dissociated matriptase after boiling (lane 6), but not with the 40-and 25-kDa bands after boiling. Anti-boiling protein mAb M19 recognized both 95- and 85-kDa complexes under non-boiling conditions (lane 3) and both 40- and 25-kDa bands after boiling (lane 4).

Another mAb, M58, recognized only the 95-kDa matriptase complex (not the 85-kDa complex) under non-boiling conditions (lane 1); this mAb also detected the 40-kDa band, but not the 25-kDa band or the dissociated matriptase (lane 2). B, shown is a summary of the structures of matriptase-containing complexes and mAbs that are directed against these complexes and their subunits. BP-40 and BP-25, 40- and 25-kDa binding proteins, respectively.

FIG. 5: Amino Acid Sequence Comparison of the Binding Protein and the Inhibitor of Human Hepatocyte Growth Factor Activator (HAI-1)

Twelve-amino acid (GPPPAPPGLPAG) (SEQ ID NO: 2) and seven-amino acid (TQGFGGS) (SEQ ID NO: 3) sequences of the amino termini obtained from the 40-kDa binding protein doublet and the 25-kDa binding protein, respectively, and were identical to amino acids 36-47 and 154-160 of HAI-1 (SEQ ID NO: 1). In addition, 12 unique peptides from the tryptic digest of the larger band of the 40-kDa binding protein doublet were compared with HAI-1 by MALDI-MS. These peptides covered 87 residues that spanned positions 135-310, or 17% of the entire HAI-1. The two stretches of amino-terminal protein sequences are double-underlined, and those 12 peptides identified by MALDI-MS, including residues 135-143, 154-164, 165-172, 173-182, 173-190, 183-190, 194-199, 203-214, 204-214, 288-301, and 302-310 (SEQ ID NO: 1), are underlined.

FIG. 6: Western Blot Analysis of HAI-1 Protein Expressed In COS-7 Cells Using Anti-Binding Protein mAb M19

The HAI-1 cDNA fragment that was generated by reverse transcriptase-polymerase chain resection and that contains the entire coding region was inserted into the expression vector pcDNA3.1 and transfected into COS-7 cells. Cell lysates from HAI-1-transfected COS-7 cells (lane 2), COS-7 cells (lane 3), and matriptase-transfected COS-7 cells (lane 1), and the 2 M KCl-washed membrane fraction of T-47D human breast cancer cells (lane 4) were subjected to Western blot analysis using anti-binding protein mAb M19.

Figure 7:
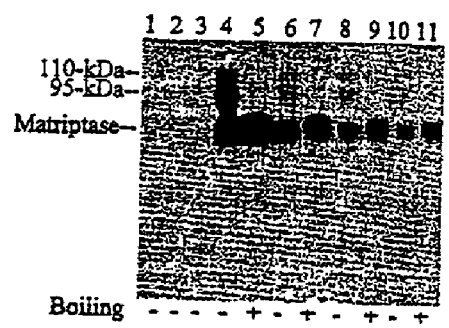

FIG. 7: Expression Analysis of Matriptase And Its Complexes in Human Foreskin Fibroblass, Fibrosarcoma and Immortalized mammary Luminal Epithelial Cells Total released proteins in the serum-free conditioned medium of each cell line were collected and concentrated. Total protein (3 µg of protein/lane was incubated in 1×SDS sample buffer in the absence of reducing agents at room temperature (−Boiling) or at 95° C. (+Boiling), subjected to SDS-PAGE, transferred to polyvinylidene fluoride (PVDF) membrane, and probed by anti-matriptase mAb 21-9. Lanes 1 (HS27) and 2 (HS68) are human foreskin fibroblasts. Lane 3 is HT-1080 fibrosarcoma cells. Lanes 4-11 are four milk-derived, SV40-immortalized luminal epithelial cells: MTSV-1.1B (lanes 4 and 5); MTSV-1.7 (lanes 6 and 7); MRSV-4.1 (lanes 8 and 9); and MRSV-4.2 (lanes 10 and 11). In addition to uncomplexed matriptase, various levels of 95- and 110-kDa complexes were seen in non-boiled samples, but disappeared by boiling treatment, in conjunction with increased matriptase.

Figure 8:
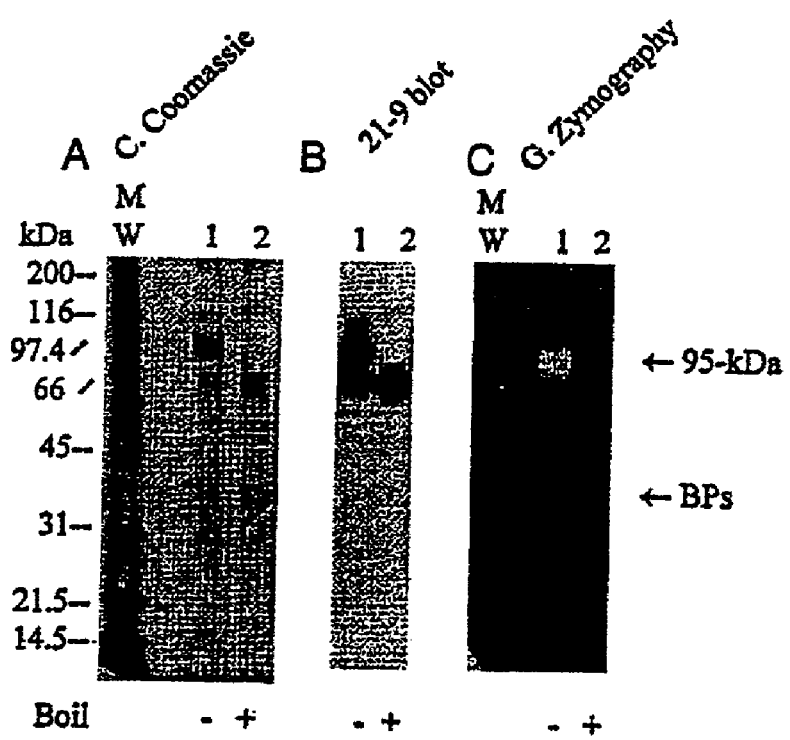

FIG. 8: Purification of Matriptase In Its 95-kDa Complexed Form From Human Milk The partially purified 95-kDa matriptase complex from ion-exchange chromatography was loaded onto a mAb 21-9-Sepharose column. The bound proteins were eluted by glycine buffer, pH 2.4, and neutralized by addition of 2 M Trizma. The eluted proteins were incubated in 1×SDS sample buffer in the absence of reducing agents at room temperature (lanes 1; −Boil) or at 95° C. (lanes 2; +Boil) for 5 min. The samples were resolved by SDS-polyacrylamide gel electrophoresis and either stained by colloidal Coomassie (A) or subjected to immunoblot analysis using mAb 21-9 (B) or gelatin zymography (C). The 95-kDa matriptase complex was eluted from this affinity column as the major protein (A, lane 1); it was recognized by mAb 21-9 (B, lane 1); and it also exhibited gelatinolytic activity (C, lane 1). The 95-kDa matriptase complex was converted to matriptase by boiling (A, lane 2). The gelatinolytic activity of the 95-kDa protease was destroyed by boiling, but a low level of the gelatinolytic activity was survived and converted to matriptase (C, lane 2). A low level of uncomplexed matriptase was co-purified with the 95-kDa matriptase complex by affinity chromatography (A, lane 1); it also exhibited gelatinolytic activity (C, lane 1). Immunoblot analysis enhanced the signal of the uncompleted matriptase and reconfirmed its existence (B, lane 1). Several other polypeptides were also seen (A, lanes 1 and 2). Some of them could be the degraded products of the protease since they were recognized by mAb 21-9 after longer exposure to the x-ray film. A 40-kDa protein doublet was seen in low levels in a non-boiled sample (A, lane 1), but its levels were increased after boiling (A, lane 2). This 40-kDa doublet was not recognized by mAb 21-9 (B). We propose that these two polypeptides could be binding proteins (BPs) of matriptase. The sizes of the molecular mass markers are indicated.

Figure 9:
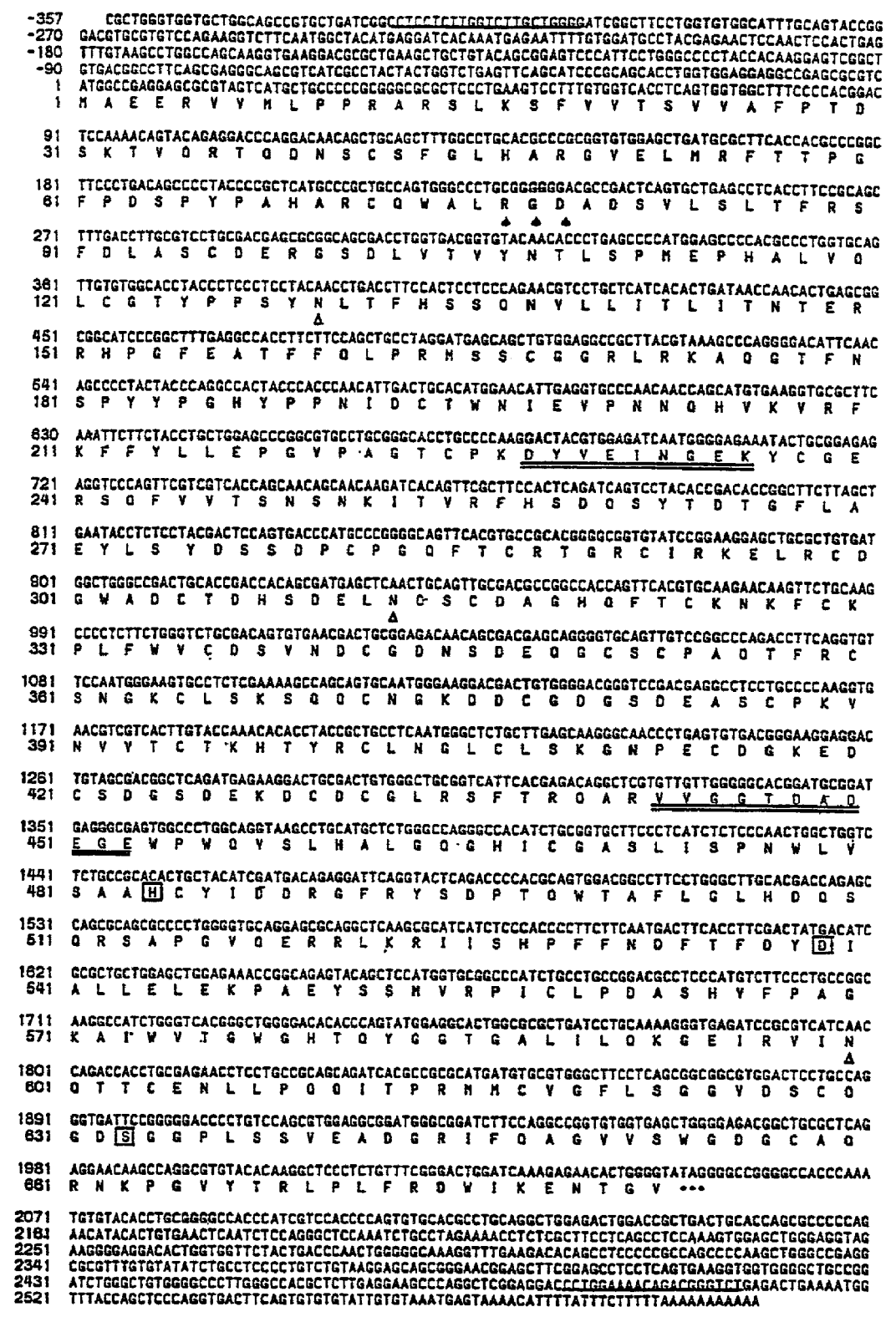

FIG. 9: The Nucleotide and Deduced Amino Acid Sequences (SEQ ID NO: 4 5) Of A Matriptase cDNA Clone The primers (20 bases at the 5'-end and 18 bases at the 3'-end) used for reverse transcriptase-polymerase chain reaction are underlined. Thirty-three bases beyond the 5'-end primer and 92 bases beyond the 3'-end primer were taken from SNC19 cDNA and incorporated. The cDNA sequence (SEQ ID NO: 4) was translated from the fifth ATG codon in the open reading frame. Nucleotide and amino acid numbers are shown on the left. Sequences that agreed with the internal sequences obtained from matriptase are double-underlined. His-484, Asp-539, and Ser-633 are boxed and indicated the putative catalytic triad of matriptase. Potential N-glycosylation sites are indicated (Δ). An RGD sequence is indicated ♠.

Figure 10:
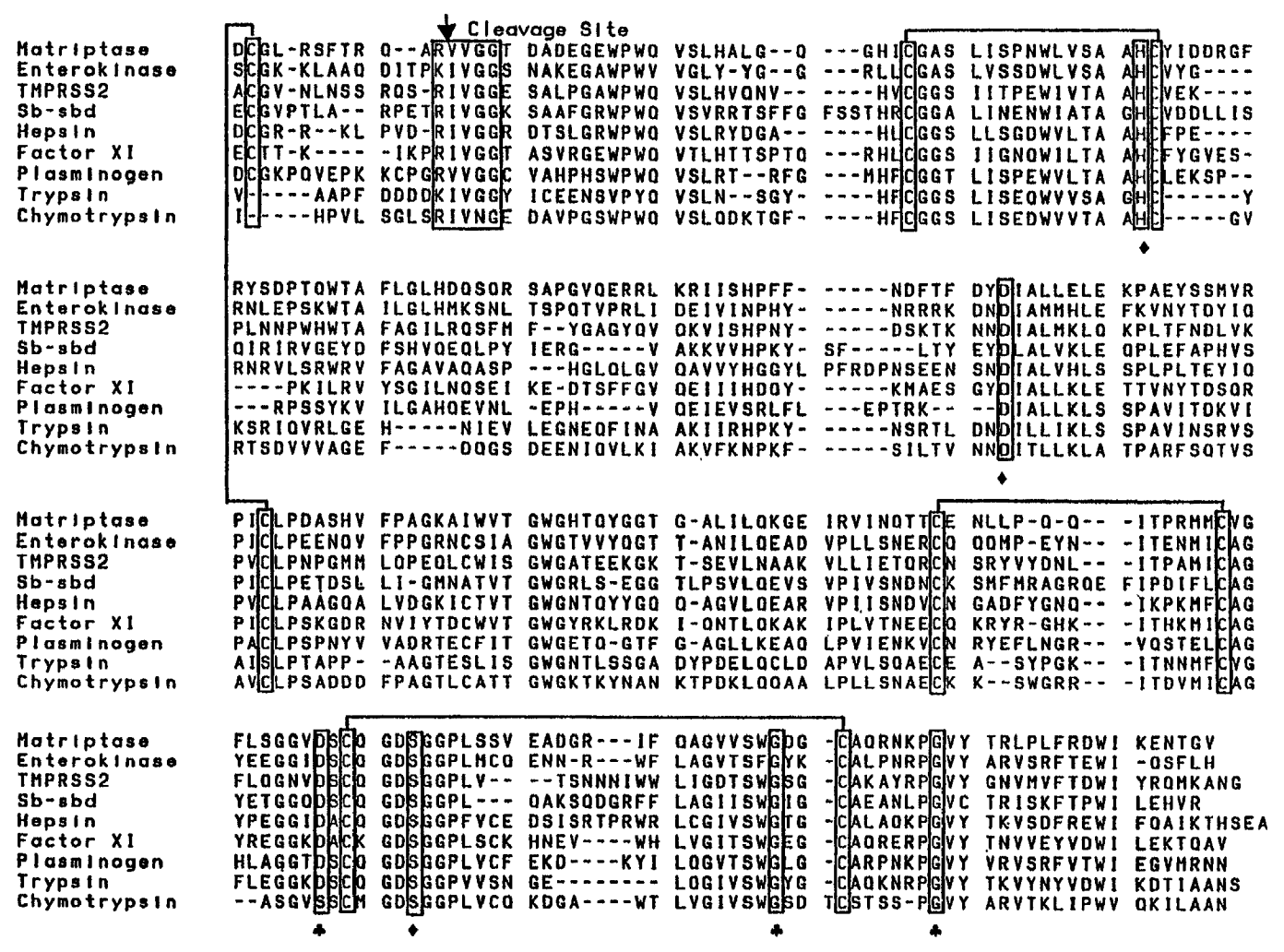

FIG. 10: Comparison of the amino acid sequence of the C-terminal region of matriptase with trypsin, chymotrypsin, and with the catalytic domains of other serine proteases. The C-terminal region (amino acids 431-683) (SEQ ID NO: 6) of matriptase is compared with human trypsin (SEQ ID NO: 13) (Emi et al., *Gene* (*Amst.*) 41: 305-10 (1986)); human chymotrypsin (SEQ ID NO: 14) (Tomita et al., *Biochem, Biophys. Res. Commun.* 158: 569-75 (1989)); the catalytic chains of human enteropeptidase (SEQ ID NO: 2) (Kitamoto et al., *Proc. Natl. Acad. Sci. USA* 91: 7588-92 (1994)); human hepsin (SEQ ID NO: 10) (Leytus et al., *Biochemistry* 27: 1067-74 (1988)), human blood coagulation factor XI (SEQ ID NO: 11) (Fujikawa et al., *Biochemistry* 25: 2417-24

(1986)), and human plasminogen (SEQ ID NO: 12); and the serine protease domains of two transmembrane serine proteases, human TMPRSS2 (SEQ ID NO: 8) (Paoloni-Giacobion et al., *Genomics* 44: 309-20 (1997) and the *Drosophila Stubble-stubbloid* gene (Sb-sbd) (SEQ ID NO: 9) (Appel et al., *Proc. Natl. Acad. Sci. USA* 90: 4937-41 (1993)). Gaps to maximize homologies are indicated by dashes. Residues in the catalytic triads (matriptase His-484., Asp-539, and Ser-633) are boxed and indicated (▲). The conserved activation motif ((R/K)VIGG) (SEQ ID NO: 34) is boxed, and the proteolytic activation site is indicated. Eight conserved cysteines needed to form four intramolecular disulfide bonds are boxed, and the likely pairings are as follows: Cys-469-Cys-485, Cys-604-Cys618, Cys-629-Cys-658,a nd Cys-432-Cys-559. The disulfide bond Cys-432-Cys-559. The disulfide bond Cys-432-Cys-559 is observed in two-chain serine proteases, but not in trypsin and chymotrypsin. Residues in the substrate pocket (Asp-627, Gly-655, and Gly-665) are boxed and indicated ♣. It is evident that the residue positioned at the bottom of the substrate pocket in Asp in trypsin-like proteases, including matriptase, but Ser in chymotrypsin.

FIG. 11: Alignment Of Partial Sequences Of The Noncatalytic Domain With Those Of Homologous Regions In Other Proteins A, the cysteine-rich repeats of matriptase (amino acids 280-314, 315-351, 352-387, and 394-430) (SEQ ID NO: 15) are compared wit the consensus sequences of the human LDL receptor (SEQ ID NO: 16) USUdohof et al. *Science* 228: 815-22 (1985)), LDL receptor-related protein (LRP) (SEQ ID NO: 17) (Herz et al., *EMBO J.* 7: 4119-27 (1988)), human perlecan (SEQ ID NO: 18) (Murdoch et al., *J. Biol. Chem.* 267: 8544-57 (1992)), and rat GP-300 (SEQ ID NO: 19) (Raychowdbury et al., *Science* 244: 1163-65 (1989)). The consensus sequences are boxed. B, C1rs/s-type sequences of matriptase (Mt; amino acids 42-155 and 168-268) (SEQ ID NOS: 20 and 21) are compared with selected domains of human complement subcomponent C1r (amino acids 193-298) (SEQ ID NO: 22) (Leytus et al., *Biochemistry* 25: 4855-63 (1986); Journet, *Biochem. J.* 240: 783-87 (1986)), C1s (amino acids 175-283) (SEQ ID NO: 23) (Mackinnon et al., *Eur. J. Biochem.* 169: 547-53 (1987); and Tosi et al. *Biochemistry* 26: 8516-24 (1987)), Ra-reactive factor (RaRF) (amino acids 185-290) (SEQ ID NO: 24) (Takada et al., *Biochem. Biophys. Res. Commun.* 196: 1003-9 (1993); and Sato et al., *Int. Immunol.* 6: 665-9 (1994)), and a calcium dependent serine protease (CSP) (amino acids 181-289) (SEQ ID NO: 25) (Kinoshita et al., *FEBS Lett.* 250: 411-5 (1989)). The consensus sequences are boxed.

FIG. 12: Shows The Domain Structure of Matriptase

A schematic representation of the structure of matriptase is presented. The protease consists of 683 amino acids, and the protein produce has a calculated mass of 75,626 Da. The protease contains two tandem complement subcomponent C1r and C1s domains and four tandem LDL receptor domains. The serine protease domain is at the carboxyl terminus.

Figure 13:
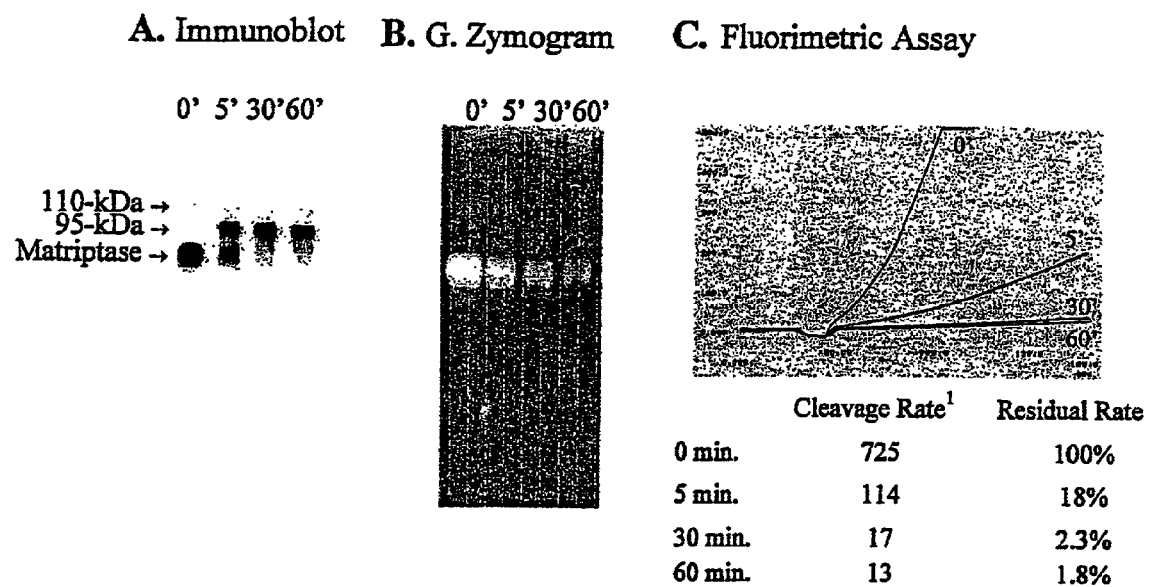

FIG. 13: Inhibition of Matriptase by HAI-1

Matriptase and HAI-1 were isolated from human milk by anti-matriptase mAb 21-9 immunoaffinity chromatography, as described in Example 1, and were maintained in an uncomplexed status in elution buffer, 0.1 M glycine, pH 2.4. This preparation was brought to pH 8.5, incubated at 37° C. for 0, 5, 30 and 60 min., and subjected to immunoblotting using anti-matriptase mAb 21-9 (panel A), gelatin zymography (panel B), and to a cleavage rate assay using the synthetic, fluorescent substrate, BOC—Gin—Ala—Agr-7-amido 4-methylcoumarin (panel C). At 0 min, matriptase was detected in its uncomplexed form (panel A), exhibiting strong gelatinolytic activity (panel B), and cleavage of soluble substrate at rapid rate (panel C). After 5 min incubation at 37° C., matriptase was detected both in an uncomplexed and complexed form (panel A); the uncomplexed matriptase exhibited gelatinolytic activity, while much weaker activity was observed for complexed matriptase (panel B); the cleavage rate for fluorescent substrate was significantly reduced, down to 18% (panel C). After 30 and 60 min. incubations, matriptase was detected mainly in an complexed form (panel A); negligible activity was observed by gelatin zymography (panel B) and by cleavage of fluorescent substrate. A milk-derived, matriptase-related 110-kDa protease (as indicated in panel A), which was not a complex of matriptase and HAI-1, and whose migration on SDS gel was reduced after boiling (see Example 1).

Figure 14:
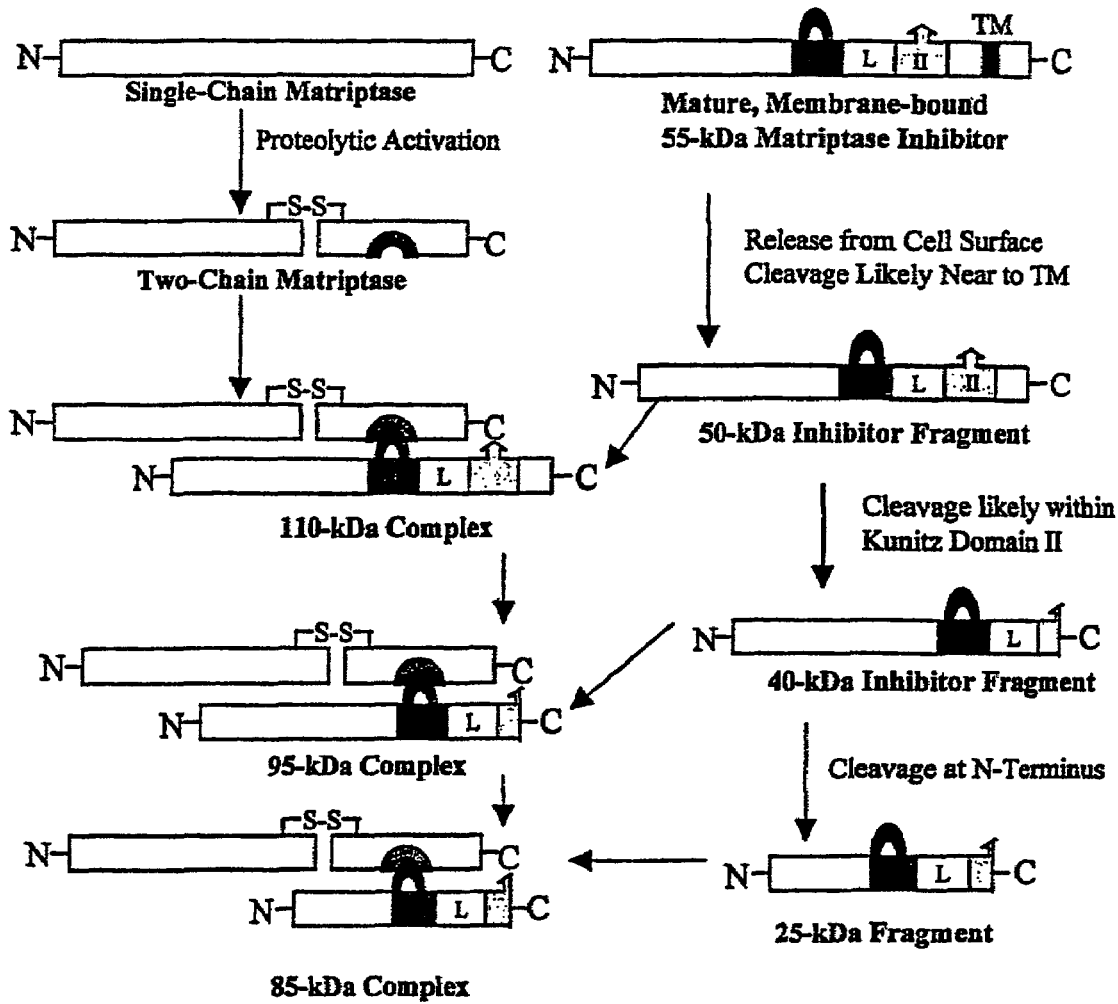

FIG. 14: Schematic Representation Of Processing And Interaction Of Matriptase And Its Cognate Inhibitor Both matriptase and its cognate inhibitor are likely to be biosynthesized as integral membrane proteins. "TM" indicates the location of the transmembrane domain. "I" stands for Kunitz domain 1; "II" for Kunitz domain 2; and "L" stands for LDL receptor domain.

FIG. 15: Nucleic Acid Sequence For Human Matriptase (SEQ ID NO: 26)

SEQ ID NO: 26 contains additional nucleic acid sequence encoding the first 172 amino acids located in the amino-terminus of the encoded protein as compared to SEQ ID NO: 4, which encodes a truncated form of matriptase. SEQ ID NO: 26 represents the full-length form of the nucleic acid encoding matriptase, whereas SEQ ID NO: 4 encodes a truncated form. The sequence can be found at GenBank Accession NO. AF118224.

FIG. 16: Amino Acid Sequence For Human Matriptase (SEQ ID NO: 22)

This sequence contains 855 amino acids, which is larger than the sequence described in Lin et al., *J. Biol. Chem*, 274: 18231-6 (1999) (SEQ ID NO: 5). SEQ ID NO: 27 is the full length form of the matriptase protein, whereas SEQ ID NO: 5 is a truncated matriptase protein lacking 172 amino acids at the amino terminus. The protein sequence can be found at GenBank Accession No. AAD42765.

Figure 17:
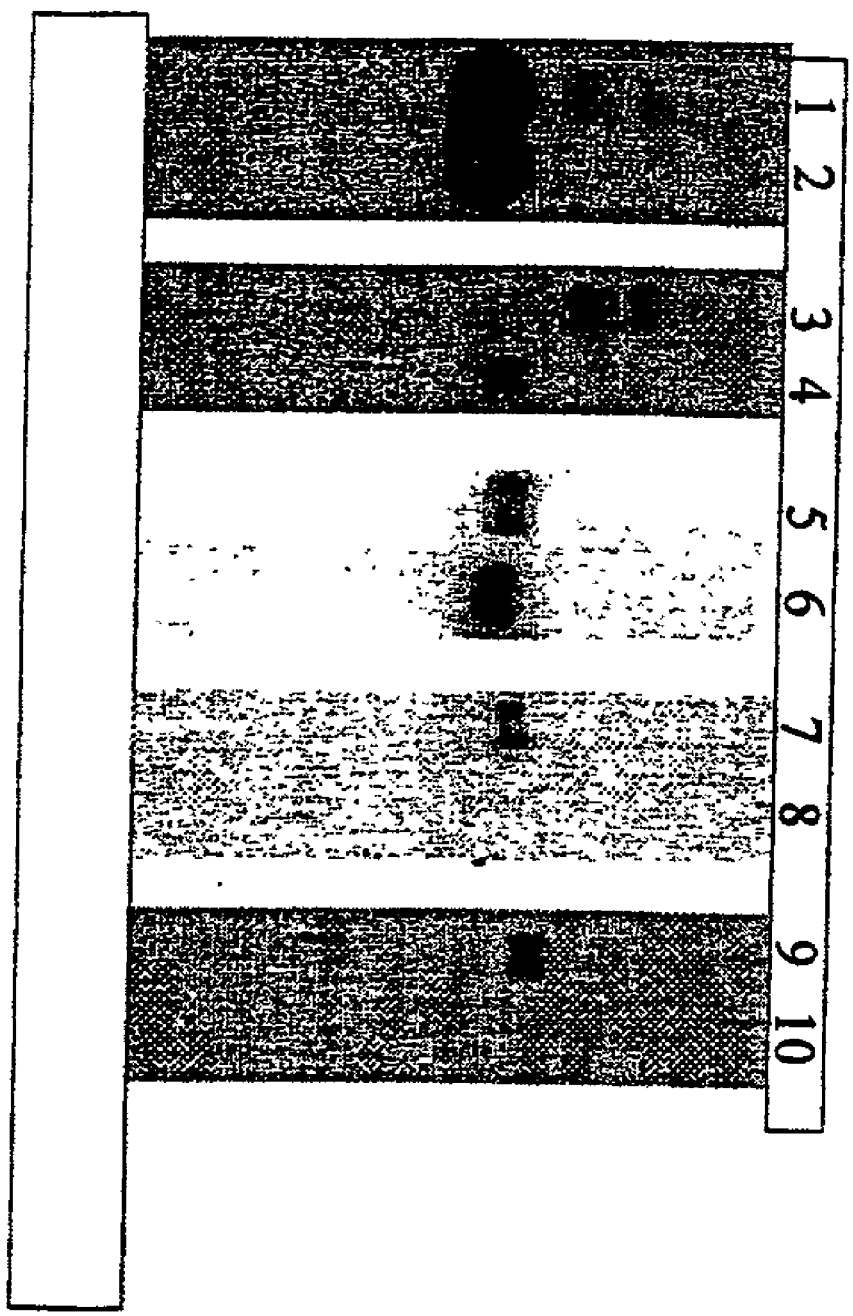

FIG. 17: Production of mAbs Which Are Specifically Directed Against Active, Two-Chain Form of Matriptase This Western blot compares the affinities of monoclonal antibodies M130 (lanes 1 and 2), M123 (lanes 3, 4, 7 and 8), M32 (lanes 5 and 6), and M69 (lanes 9 and 10) to different forms of matriptase.

OBJECTS AND SUMMARY OF THE INVENTION

It is an object of the invention to provide a method of preventing and treating malignancies, pre-malignant conditions, and other conditions in a subject which are characterized by the presence of a single-chain (zymogen) and/or two-chain (activated) form of matriptase in a biological sample comprising the step of administering the amount of a matriptase modulating agent capable of preventing or treating the malignancy, the pre-malignant lesion, or other condition.

It is another object of the invention to provide matriptase inhibitors, such as a Bowman Birk inhibitor (BBI) or structurally related molecules or fragments thereof.

Another object of the invention is to provide nucleic acid molecules (SEQ ID NOS: 4 and 26) encoding matriptase proteins or polypeptide fragments thereof (SEQ ID NOS: 5 and 27).

It is a further object of the invention to provide an antibody or antibodies which recognizes and binds to SEQ ID NO: 5 or a fragment thereof, SEQ ID NO: 27 or a fragment thereof, to a single-chain (zymogen) form or matriptase or to a two-chain (active) form of matriptase. Preferred antibodies are monoclonal antibodies and fragments thereof sa well as chimeric, humanized or human antibodies.

It is also an object of the invention to provide a method of inhibiting tumor onset, tumor growth, and invasion or tumor metastasis, or other pathologic conditions, by administering an agent which inhibits or modulates activation of the zymogen form of matriptase or the activity of the two-chain (active form of matriptase expressed by a tumor cell on a cell of other pathologic conditions. One preferred agent is BBIC, fragments thereof, or structurally related inhibitors (e.g., structurally related serine protease inhibitors).

Another object of the invention is a method of identifying a compounder that specifically binds to a single-chain or a two-chain form of matriptase comprising the steps of: (A) exposing a single-chain or two-chain form of matriptase to a compound; (B) determining whether the single-chain or two-chain form of matriptase specifically binds to the compound; and (C) determining whether the compound that binds to the single-chain form of matriptase inhibits activation to the two-chain form of matriptase, or whether the compound binds to the two-chain form of matriptase and inhibits its catalytic activity.

It is a further object of the invention to disclose a method of diagnosing in vivo the presence of a pre-malignant lesion, a malignancy, or other pathologic condition in a subject comprising the steps of: (A) administering a labeled agent to a subject which recognizes and binds to a single-chain or two-chain form of matriptase; and (B) imaging the subject for the localization of the labeled agent.

It is a further object of the invention to diagnose in vitro the presence of a pre-malignant lesion, a malignancy, or other pathologic conditions in a subject comprising the steps of: (A) obtaining a biological sample from a subject that is to be tested for a pre-malignant lesion, a malignancy, or other pathologic condition; (B) exposing the biological sample to a labeled agent which recognizes and binds to the single-chain form and/or the two-chain form of matriptase; and (C) determining whether said labeled agent bound to the biological sample.

Another object of the invention is to provide a method of identifying a compound that specifically binds to a single-chain or a two-chain form of matriptase comprising the steps of: (A) identifying by molecular modeling whether the compound could bind to the activation site on the single-chain form of matriptase, the catalytic site of the two-chain form of matriptase, the C1r/C1s domain of either form of matriptase, or other regulatory domain of the molecule; (B) exposing a single-chain form or two-chain form of matriptase to the compound; (C) determining whether the compound binds to the single-chain form or the two-chain form of matriptase; and (D) if the compound binds to a form of matriptase, further determining whether the compound inhibits activation of the single-chain form of matriptase to a two-chain form of matriptase, whether the compound binds to the two-chain form of matriptase and inhibits its catalytic activity, whether the compound binds to the C1r/C1s domain, and thereby inhibits dimerization of the protein, or whether the compound binds to another regulatory domain of matriptase thereby modulating activation of matriptase or a matriptase activity.

DETAILED DESCRIPTION OF THE INVENTION

Matriptase is a trypsin-like serine protease with two regulatory modules: two tandem repeats of the complement subcomponent C1r/s domain and four tandem repeats of LDL receptor domain (Lin et al., *J. Biol. Chem.* 274: 18231-6 (1999)). In order to evaluate the role of matriptase in physiological conditions, its expression in human milk was studied. It was found that milk-derived matriptase strongly interacts with fragments of HAI-1 to form SDS-stable complexes.

The mosaic protease is characterized by trypsin-like activity and two regulatory modules (e.g., LDL receptor and complement subcomponent S1r/s domains), was initially purified from T-47D human breast cancer cells.

In breast cancer cells, matriptase was detected mainly as an uncomplexed form; however, low levels of matriptase were detected in SDS-stable, 110-and 95-kDa complexes that could be dissociated by boiling. In striking contrast, only the complexed matriptase was detected in human milk. The complexed matriptase has now been purified by a combination of ionic exchange chromatography and immunoaffinity chromatography. Amino acid sequences obtained from the matriptase-associated proteins reveal that they are fragments of an integral membrane, Kunitz-type serine protease inhibitor that was previously reported to be an inhibitor (termed HAI-1) of hepatocyte growth factor activator. In addition, matriptase and its complexes were also detected in four milk-derived, SV-40 T-antigen-immortalized mammary luminal epithelial cell lines, but not in two human foreskin fibroblasts nor in HT1080 fibrosarcoma cell line. The milk-derived matriptase complexes are likely to be produced by the epithelial components of lactating mammary gland in vivo, and the activity and function of matriptase may be differentially regulated by its cognate inhibitor, comparing breast cancer with the lactating mammary gland.

A. Definitions

By "matriptase" is meant a trypsin-like protein, with a molecular weight of between 72-kDa and 92-kDa and is related to SEQ ID NO: 27 or is a fragment thereof. It can include both single-chain and double-chain forms of the protein. The zymogen form (inactive form) of matriptase is a single-chain protein. The two-chain form of matriptase is the active form of matriptase, which possesses catalytic activity. Both forms of matriptase are found to some extent in milk and cancer cells because extracellular matrix (ECM) remodeling is necessary to both normal and pathologic remodeling processes. FIG. 14 displays all known forms of matriptase. Both cancer cells and milk contain the different forms of matriptase. However, in milk the dominant form is the activated form of matriptase which then binds to HAI-1.

By "matriptase modulating compound" or "matriptase modulating agent" is meant a reagent which regulates, preferably inhibits the activation of matriptase (e.g., cleavage of the matriptase single-chain zymogen to the active two-chain moiety) or the activity of the two-chain form of matriptase. This inhibition can be at the transcriptional, translation, and/or post translational levels. Additionally, modulation of matriptase activity can be via the binding of a compound to the zymogen or activated forms of matriptase.

By "matriptase expressing tissue" is meant any tissue which expresses any form of matriptase, either malignant, pre-malignant, normal tissue, or tissue which is subject to another pathologic condition.

By "BBI" is meant compounds known as Bowman-Birk inhibitors, including those from soybeans as described by Birk, *Int. J. Pept. Protein Res.* 25: 113-21 (1985). BBIs have been isolated from leguminous plants and have a molecular weight of about 8,000 to 20,000 Daltons and include, but are not limited to, for example: BBI inhibitors of *Dolichos bifloros* and *Macrotyloma uniflorum* seeds, BBI inhibitors of *Torresea cearensis* seeds, BBI inhibitors of winder pea seeds, DgTI, and BBI-like inhibitors of sunflower seeds (Prakash et al., *J. Mol. Biol.* 235: 364-6 (1994); Tanaka et al., *Biol. Chem.* 378: 273-81 (1997); Quillien eta l., *J. Protein Chem.* 16: 195-203 (1997); Bueno et al., *Biochem. Biophys. Res. Commun.* 261: 838-43 (1999); and Luckett et al., *J. Mol. Biol.* 290: 525-33 (1999)). BBI-like inhibitors are those with sequence and conformation similarity with the trypsin-reactive loop of the Bowman-Birk family of serine protease inhibitors. BBIs and BBI-like inhibitors can include any isoforms.

By "BBIC" is meant a concentrate of BBI or biologically active fragments thereof that inhibit matriptase activity (e.g., amino acid substituted protease inhibitory loops). The BBIC concentrate will preferably contain an amount of BBI ranging from 0.00001 to at least about 0.1 mg/ml. Preferably the BBIC will be administered in dosage sufficient to obtain a blood level of 0.001 to 1 mM concentration of BBI in the blood as a means of inhibiting tumor initiation in, for example, a subject susceptible to breast cancer as indicated by the presence of matriptase and/or matriptase complexes in nipple aspirate or other biological fluid, or in tissue from biopsy, including tissue from a needle biopsy.

By "malignancy" is meant to refer to a tissue, cell or organ which contains a neoplasm or tumor that is cancerous as opposed to benign. Malignant cells typically involve growth that infiltrates tissue (e.g., metastases). By "benign" is meant an abnormal growth which does not spread by metastasis or infiltration of the tissue. The malignant cell of the instant invention can be of any tissue; preferred tissues are epithelial cells.

By "tumor invasion" or "tumor metastasis" is meant the ability of a tumor to developed secondary tumors at a site remote from the primary tumor. Tumor metastasis typically requires local invasion, passive transport, lodgment and proliferation at a remote site. This process also requires the development of tumor vascularization, a process termed angiogenesis. Therefore, by "tumor invasion" and "metastasis," we also include the process of tumor angiogenesis.

By "pre-malignant conditions" or "pre-malignant lesion" is meant a cell or tissue which has the potential to turn malignant or metastatic, and preferably epithelial cells with said potential. Pre-malignant lesions include, but are not limited to: atypical ductal hyperplasia of the breast, actinic keratosis (AK), leukoplakia, Barrett's epithelium (columnar metaplasia) of the esophagus, ulcerative colitis, adenomatous colorectal polyps, erythroplasia of Queyrat, Bowen's disease, bowenoid papulosis, vulvar intraepithelial neoplasia (VIN), and displastic changes to the cervix.

By "other condition" or "pathologic conditions" is meant any genetic susceptibility or non-cancerous pathologic condition relating to any disease susceptibility or diagnosis.

By "tumor formation-inhibiting effective amount" is meant an amount of a compound, which is characterized as inhibiting activation of matriptase or matriptase activity, and which when administered to a subject, such as a human subject, prevents the formation of a tumor, or causes a preexisting tumor, or pre-malignant condition, to enter remission. This can be assessed by screening a high-risk patient for a prolonged period of time to determine that the cancer does not arise and/or the pre-malignant condition is reversed. This also can be assessed by imaging of the subject with a tumor to determine whether the mass of the tumor is shrinking. A tumor formation-inhibiting effective amount also includes an amounts which provides ameliorative to relief to the subject. The tumor formation-inhibiting effective amount can also be assessed based on its effect on blood circulation of inhibitors, such as BBIC. Preferred tumor formation-inhibiting effective amounts of agents such as BBIC are in the range of 100 µg/kg to 20 mg/kg body weight of the subject. More preferred ranges includes 1 µg/kg to 10 mg/kg body weight of the subject.

By "labeling agent" is meant to include fluorescent labels, enzyme labels, and radioactive labels. By "radiolabel" or "radioactive label" is meant any radioisotope for use in humans for purposes of diagnostic imaging. Preferred radioisotopes for such use include: $^{67}$Cu, $^{67}$Ga, $^{99}$Te, $^{131}$I, $^{123}$I, $^{125}$I, $^{111}$In, $^{188}$Re, $^{186}$Re and $^{90}$Y. By "fluorescent label" is meant any compound used for screening samples (e.g., tissue samples and biopsies) which emits fluorescent energy. Preferred fluorescent labels include fluorescein, rhodamine and phycoerythrin.

By "biological sample" is meant a specimen comprising body fluids, cells or tissue from a subject, preferably a human subject. Preferably the biological sample contains cells, which can be obtained via a biopsy or a nipple aspirate, or are epithelial cells. The sample can also be body fluid that has come into contact, either naturally or by artificial methods (e.g. surgical means), a malignant cell or cells of a pre-malignant lesion.

By "matriptase expressing tissue" is meant any biological sample comprising one or more cells which expresses a form or forms of matriptase.

By "subject" is meant an animal, preferably mammalian, and most preferably human.

As used herein, the term "antibody" is meant to refer to complete, intact antibodies, and Fab fragments and F(ab), fragments thereof. Complete, intact antibodies include monoclonal antibodies such as murine monoclonal antibodies (mAb), chimeric antibodies and humanized antibodies. The production of antibodies and the protein structures of complete, intact antibodies, as well as antibody fragments (e.g., Fab fragments and F(ab)$_2$ fragments ( and the organization of the genetic sequences that encode such molecules are well known and are described, for example, in Harlow, et al., ANTIBODIES: A LABORATORY MANUAL, Cold Spring Harbor Laboratory, Cold Spring Harbor, N.Y. (1988).

By "immunogenic fragment" is meant a portion of a matriptase protein which induces humoral and/or cell-mediated immunity but not immunological tolerance.

By "epitope" is meant a region on an antigen molecule (e.g., matriptase) to which an antibody or an immunologically reactive fragment thereof binds specifically. The epitope can be a three dimensional epitope formed from residues on different regions of a protein antigen molecule, which, in a native state, are closely apposed due to protein folding. "Epitope" as used herein can also mean an epitope created by a peptide or hapten portion of matriptase and not a three dimensional epitope.

B. Nucleic Acid Molecules

The present invention further provide nucleic acid molecules that encode the protein having SEQ ID NO: 5 or SEQ ID NO: 27, or fragments thereof, and related proteins, which are preferably in isolated form. As used herein, "nucleic acid" is defined as RNA or DNA that encodes a peptide as defined above, or is complementary to nucleic acid sequence encoding such peptides, or hybridizes to such nucleic acid and remains stably bound to it under appropriate stringency conditions, or encodes a polypeptide sharing at least 75% sequence identify, preferably at least 80%, and more preferably at least 85%, with the peptide sequences. Specifically contemplated are genomic DNA, cDNA, mRNA and antisense molecules, as well as nucleic acids based on alternative backbone or including alternative bases whether derived from natural sources or synthesized.

"Stringent conditions" are those that (1) employ low ionic strength and high temperature for washing, for example, 0.015 M NaCl, 0.0015 M sodium titrate, 0.1% SDS at 50° C.; or (2) employ during hybridization a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C. Another example is use of 50% formamide, 5X SSC (0.75 M NaCl, 0.075 M sodium citrate), 50 mM sodium phosphate (pH 6.8), 0.1% sodium pyrophosphate, 5X Denhardt's solution, sonicated salmon sperm DNA (50 μg/ml), 0.1% SDS, and 10% dextran sulfate at 42° C., with washes at 42° C. in 0.2X SSC and 0.1% SDS. A skilled artisan can readily determine and vary the stringency conditions appropriately to obtain a clear and detectable hybridization signal.

As used herein, a nucleic acid molecule is said to be "isolated" when the nucleic acid molecule is substantially separated from contaminant nucleic acid encoding other polypeptides from the source of nucleic acid.

The present invention further provides fragments of the BBI nucleic acid coding sequence. As used herein, a fragment of a BBI coding sequence refers to a truncated version of the entire protein encoding sequence. The size of the fragment will be determined by the intended use. For example, if the fragment is chosen so as to encode an active portion of the protein, the fragment will need to be large enough to encode the functional region(s) of the protein. If the fragment is to be used as a nucleic acid problem or PCR primer, then the fragment length is chosen so as to obtain a relatively small number of false positives during probing/priming.

Fragments of the nucleic acid molecules of the present invention (i.e., synthetic oligonucleotides) that are used as probes or specific primers for the polymerase chain reaction (PCR), or to synthesize gene sequences encoding proteins of the invention can easily be synthesized by chemical techniques, for example, the phosphotriester method of Matteucci et al., J. Am. Chem. Soc. 103: 3185-91 (1981) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The BBI nucleic acid molecules of the present invention may further be modified so as to contain a detectable label for diagnostic and probe purposes A variety of such labels are known in the art and can readily be employed with the encoding molecules herein described. Suitable labels include, but are not limited to, biotin, radiolabeled nucleotides and the like. A skilled artisan can employ any of the art known labels to obtain a labeled encoding nucleic acid molecule.

Modifications to the primary structure itself by deletion, addition, or alteration of the amino acids incorporated into the protein sequence during translation can be made without destroying the activity of the protein. Such substitutions or other alterations result in proteins having an amino acid sequence encoded by a nucleic acid falling within the contemplated scope of the present invention.

C. Isolation Of Other Related Nucleic Acid Molecules

As described above, the identification of the human nucleic acid molecule having SEQ ID NO: 4 or SEQ ID NO: 26 allows a skilled artisan to isolate nucleic acid molecules that encode other members of the matriptase family, in addition to the human sequence herein described. Further, the presently disclosed nucleic acid molecules allow a skilled artisan to isolate nucleic acid molecules that encode other members of the matriptase family of proteins in addition to the disclosed protein having SEQ ID NO: 5 and SEQ ID NO: 27.

Essentially, a skilled artisan can readily use the amino acid sequence of NO: 5 or SEQ ID NO: 27 to generate antibody probes to screen expression libraries prepared from appropriate cells. Typically, polyclonal antiserum from mammals, such as rabbits, immunized with the purified protein (as described below) or monoclonal antibodies can be used to probe a mammalian cDNA or genomic expression library, such as λgtll library, to obtain the appropriate coding sequence for other members of the protein family The cloned cDNA sequence can be expressed as a fusion protein, expressed directly using its own control sequences, or expressed by constructions using control sequences appropriate to the particular host used for the expression of the enzyme.

Alternatively, a portion of the coding sequence herein described can be synthesized and used as a probe to retrieve DNA encoding a member of the protein family from any mammalian organism. Oligomers containing approximately preferred 18-20 nucleotides or more (encoding about a 6-7 amino acid stretch) are prepared and used to screen genomic DNA or cDNA libraries to obtain hybridization under stringent conditions or conditions of sufficient stringency to eliminate an undue level of false positives.

Additionally, pairs of oligonucleotide primers can be prepared for use in a polymerase chain reaction (PCR) to selectively clone an encoding nucleic acid molecule. A PCR denature/anneal/extend cycle for using such PCR primers is well known in the art and can readily be adapted for use in isolating other encoding nucleic acid molecules.

D. rDNA Molecules Containing a Nucleic Acid Molecule

The present invention further provides a recombinant DNA molecules (rDNAs) that contain a coding sequence. As used herein, a rDNA molecule is a DNA molecule that has been subjected to molecular manipulating in situ. Methods for generating rDNA molecules are well known in the art, for example, see Sambrook et al., (1989). In the preferred rDNA molecules, a coding DNA sequence is operably linked to expression control sequences and/or vector sequences.

The choice of vector and/or expression control sequences to which a matriptase-encoding sequence of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control elements formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.), and pPL and pKK223 available from Pharmacia, Piscataway, N.J.

Expression vectors compatible with eukaryotic cells, preferably those compatible with vertebrate cells, can also be used to form a rDNA molecules the contains a coding sequence. Eukaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), the vector pCDM8 described herein, and the like eukaryotic expression vectors.

Eukaryotic cell expression vectors used to construct the rDNA molecules of the present invention may further include a selectable marker that is effective in an eukaryotic cell, preferably a drug resistance selection marker. AS preferred drug resistance marker is the gene whose expressing results in neomycin resistance, i.e., the neomycin phosphotransferase (neo) gene (Southern et al., *J. Mol. Anal. Genet.* 1: 327-341 (1982)). Alternatively, the selectable marker can be present on a separate plasmid, and the two vectors are introduced by co-transfection of the host cell, and selected by culturing in the appropriate drug for the selectable marker.

E. Host Cells Containing An Exogenously Supplied Coding Nucleic Acid Molecule The present invention further provides host cells transformed with a nucleic acid molecule that encodes a protein of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey, or human cell line. Preferred eukaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eukaryotic tissue culture cell lines (e.g., not breast cell lines).

Any prokaryotic host can be used to express a rDNA molecule encoding a protein of the invention. The preferred prokaryotic host is *E. coli*.

Transformation of appropriate cell hosts with a rDNA molecule of the present invention is accomplished by well known-methods that typically depend on the type of vector used and host system employed. With regard to transformation of prokaryotic host cells, electroporation and salt treatment methods are typically employed, see, for example, Cohen et al., *Proc. Natl. Acad. Sci. USA* 69: 2110 (1972); and Maniatis et al., MOLECULAR CLONING, A LABORATORY MANUAL, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., *Virol.* 54:536-9 (1973); and Wigler et al., *Proc. Natl. Acad. Sci. USA* 76: 1373-6 (1979).

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, *J. Mol. Biol.* 98: 503-17 (1975) or the proteins produced from the cell assayed via an immunological method.

F. Production of Recombinant Proteins Using A rDNA Molecule

The present invention further provides methods for producing a protein of the invention (e.g., matriptase) using nucleic acid molecules herein described. In general terms, the production of a recombinant form of a matriptase protein typically involves the following steps:

First, a nucleic acid molecule is obtained that encodes a protein of the invention, such as the nucleic acid molecule depicted in SEQ ID NOS: 4 or 26, or particularly for the matriptase nucleotides encoding for example, the serine protease catalytic domain in the carboxy terminus of the matriptase protein or the LDL domain. The coding sequence is directly suitable for expression in any host, as it is not interrupted by introns. The sequence can be transfected into host cells such as eukaryotic cells or prokaryotic cells. Eukaryotic hosts include mammalian cells (e.g., HEK293 cells, CHO cells and PAE-PDGF-R cells), as well as insect cells such as Sf9 cells using recombinant baculovirus. Alternatively fragments encoding only portion of matriptase can be expressed alone or as a fusion protein. For example, the C-terminus of matriptase containing the serine protease domain can be expressed in bacteria as a GST- or His-tag fusion protein. These fusion proteins can the purified and used to generate polyclonal antibodies.

The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

G. Methods to Identify Binding Partners

Another embodiment of the present invention provides methods for use in isolating and identifying binding partners of matriptase proteins. In detail, a protein of the invention is mixed with a potential binding partner or an extract or fraction of a cell under conditions that allow the association of potential binding partners with the protein of the invention. After mixing, peptides, polypeptides, proteins or other molecules that have become associated with a protein of the invention are separated from the mixture. The binding partner that bound to the protein of the invention are separated from the mixture. The binding partner that bound to isolate a binding partner, the entire protein, for instance the entire disclosed protein of SEQ ID NO: 5 or SEQ ID NO: 27 can be used. Alternatively, a fragment of the protein can be used.

As used herein, a cellular extract refers to a preparation or fraction which is made from a lysed or disrupted cell.

A variety of methods can be used to obtain cell extracts. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the protein of the invention under conditions in which association of the protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density/sediment centrifugation can be used.

After removing the non-associated cellular constituents in the extract, the binding partner can be dissociated from the complex using conventional methods. For example, dissociation can be accomplished by altering the salt concentration or pH of the mixture.

To aid in separating associated binding partner pairs from the mixed extract, the protein of the invention can be immobilized on a solid support. For example, the protein can be attached to a nitrocellulose matrix or acrylic beads. Attachment of the protein or a fragment thereof to a solid support aids in separating peptide/binding partner pairs from other constituents found in the extract. The identified binding partners can be either a single protein or a complex made up of two or more proteins.

Alternatively, the nucleic acid molecules of the invention can be used in a yeast two-hybrid system. The yeast two-hybrid system has been used to identify other protein partner pairs and can readily be adapted to employ the nucleic acid molecules herein described.

One preferred in vitro binding assay for matriptase would comprise a mixture of a polypeptide comprising at least the matriptase serine catalytic domain for and one or more candidate binding targets or substrates. After incubating the mixture under appropriate conditions, one would determine whether matriptase or a polypeptide fragment thereof containing the catalytic domain binds with the candidate substrate. For cell-free binding assays, one of the components usually comprises or is coupled to a label. The label may provide for direct detection, such as radioactivity, luminescence, optical or electron density, etc., or indirect detection such as an epitope tag, an enzyme, etc. A variety of methods may be employed to detect the label depending on the nature of the label and other assay components. For example, the label may be detected bound to the solid substrate or a portion of the bound complex containing the label may be separated from the solid substrate, and the label thereafter detected.

H. Methods To Identify Agents That Modulate the Expression a Nucleic Acid Encoding the Matriptase Another embodiment of the present invention provides methods for identifying agents that modulate the expression of a nucleic acid encoding a protein of the invention, such as a protein having the amino acid sequence of SEQ ID NO: 5 or SEQ ID NO: 27. Such assays may utilize any available means of monitoring for changes in the expression level of the nucleic acids of the invention. As used herein, an agent is said to modulate the expression of a nucleic acid of the invention, for instance a nucleic acid encoding the protein having the sequence of SEQ ID NO: 5 or SEQ ID NO: 27, if it is capable of up or down-regulating expression of the nucleic acid in a cell.

In one assay format, cell lines that contain reporter gene fusions between the open reading frame of matriptase or of SEQ ID NOS: 4 or 26 and any assayable fusion partner may be prepared. Numerous assayable fusion partners are known and readily available including the firefly luciferase gene and the gene encoding chloramphenicol acetyltransferase (Alam et al, *Anal. Biochem.* 188: 245-54 (1990)). Cell lines containing the reporter gene fusions are then exposed to the agent to be tested under appropriate conditions and time. Differential expression of the reporter gene between samples exposed to the agent and control samples identifies agents which modulate the expression of a nucleic acid encoding the protein having the sequence of SEQ ID NO: 5 or SEQ ID NO: 27 or related proteins.

Additional assay formats may be used to monitor the ability of the agent to modulate the expression of a nucleic acid encoding a protein of the invention such as the protein having SEQ ID NO: 5 or SEQ ID NO: 27. For instance, mRNA expression may be monitored directly by hybridization to the nucleic acids of the invention. Cell lines are exposed to the agent to be tested under appropriate conditions and time and total RNA or mRNA is isolated by standard procedures such those disclosed in Sambrook et al. (MOLECULAR CLONING: A LABORATORY MANUAL, 2nd Ed. Cold Spring Harbor Laboratory Press, 1989). Probes to detect differences in RNA expression levels between cells exposed to the agent and control cells may be prepared from the nucleic acids of the invention. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe target hybrid and potential probe:non-target hybrids.

Probes may be designed from the nucleic acids of the invention through methods known in the art. For instance, the G+C content of the probe and the probe length can affect probe binding to its target sequence. Methods to optimize probe specificity are commonly available, see, e.g., Sambrook et al. (1989) or Ausubel et al. (CURRENT PROTOCOLS IN MOLECULAR BIOLOGY, Greene Publishing Co., N.Y., 1995).

Hybridization conditions are modified using known methods, such as those described by Sambrook et al. (1989) and Ausubel et al. (1995), as required for each probe. Hybridization of total cellular RNA or RNA enriched for polyA RNA can be accomplished in any available format. For instance, total cellular RNA or RNA enriched for polyA RNA can be affixed to a solid support, and the solid support exposed to at least one probe comprising at least one, or part of one of the sequences of the invention under conditions in which the probe will specifically hybridize. Alternatively, nucleic acid fragments comprising at least one, or part of one of the sequences of the invention can be affixed to a solid support, such as a porous glass wafer. The glass wafer can then be exposed to total cellular RNA or polyA RNA from a sample under conditions in which the affix sequences will specifically hybridize. Such glass wafers and hybridization methods are widely available, for example, those disclosed by Beattie (WO 95/11755). By examining for the ability of a given probe to specifically hybridize to an RNA sample from an untreated cell population and from a cell population exposed to the agent, agents which up or down regulate the expression of a nucleic acid encoding the protein having the sequence of SEQ ID NO: 5 or SEQ ID NO: 27 are identified.

I. Methods to Identify Agents That Modulate at Least One Activity of the Matriptase Another embodiment of the present invention provides methods for identifying agents that modulate at least one activity of a protein of the invention, such as the protein having the amino acid sequence of SEQ ID NO: 5 or SEQ ID NO: 27. Such methods or assays may utilize any means of monitoring or detecting the desired activity, In one format, the relative amounts of a protein of the invention between a cell population that has been exposed to the agent to be tested compared to an un-exposed control cell population may be assayed (e.g., breast cancer cell line ). In the format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe.

For example, N- and C-terminal fragments of matriptase can be expressed in bacteria and used to search for proteins which bind to these fragments. Fusion proteins, such as His-tag or GST fusion to the N- or C-terminal regions of matriptase can be prepared for use as a matriptase fragment substrate. These fusion proteins can be coupled to, for example, Glutathione-Sepharose beads and then probed with cell lysates. Prior to lysis, the cells may be treated with a candidate agent which may modulate matriptase or proteins that interact with domains or matriptase. Lysate proteins binding to the fusion proteins can be resolved by SDS-PAGE, isolated and identified by protein sequencing or mass spectroscopy, as is known in the art.

Antibody probes are prepared by immunizing suitable mammalian hosts in appropriate immunization protocols using the peptides, polypeptides or proteins of the invention if they are of sufficient length (e.g., 4, 5, 6, 7, 8, 9, 10, 11, 12, 13, 14, 15, 20, 25, 30, 35, 40 or more consecutive amino acids of a matriptase protein), or if required to enhance immunogenicity, conjugated to suitable carriers. Methods for preparing immunogenic conjugates with carriers, such as bovine serum albumin (BSA), keyhole limpet hemocyanin (KLH), or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. Hapten peptides can be extended at either the amino or carboxy terminus with a Cys residue or interspersed with cysteine residues, for example, to facilitate linking to a a carrier. Administration of the immunogens is conducted generally by injection over a suitable time period and with use of suitable adjuvants, as is generally understood in the art. During the immunization schedule, titers of antibodies are taken to determine adequacy of antibody formation.

Anti-peptide antibodies can be generated using synthetic peptides corresponding to, for example, the carboxy terminal amino acids of matriptase. Synthetic peptides can be as small as 1-3 amino acids in length, but are preferably at least 4 or more amino acid residues long. The peptides can be coupled to KLH using standard methods and can be immunized into animals, such as rabbits or ungulate. Polyclonal anti-matriptase peptide antibodies can then be purified, for example using Antigen beads containing the covalently bound peptide.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler et al., (*Nature* 256: 495-7 (1975) or modifications which effect immortalization of lymphocytes or spleen cells, as is generally known. The immortalized cell lines secreting the desired antibodies are screened by immunoassay in which the antigen is the peptide hapten, polypeptide or protein. When the appropriate immortalized cell culture secreting the desired antibody is identified, the cells can be cultured either in vitro or by production in vivo via ascities fluid. Of particular interest, are monoclonal antibodies which recognize the catalytic domain of matriptase (e.g., amino acids 432-683 of SEQ ID NO: 5).

Additionally, the zymogen or two-chain forms of matriptase can be utilized to make monoclonal antibodies which recognize conformation epitopes. For peptide-directed monoclonal antibodies, peptides from the C1r/C1s domain can be used to generate anti-C1r/C1s domain monoclonal antibodies which can thereby block activation of the zymogen to the two-chain form of matriptase. This domain can similarly be the substrate for other non-antibody compounds which bind to these preferred domains on either the single-chain or double-chain forms of matriptase and thereby modulate the activity of matriptase or prevent its activation.

The desired monoclonal antibodies are then recovered from the culture supernatant or from the ascities supernatant. Fragments of the monoclonals or the polyclonal antisera which contain the immunologically significant portion can be used as antagonists, as well as the intact antibodies. Use of immunologically reactive fragments, such as the Fab, Fab', or F(ab')$_2$ fragments are often preferable, especially in a therapeutic context, as these fragments are generally less immunogenic than the whole immunoglobulin.

The antibodies or fragments may also be produced, using current technology, by recombinant means. Regions that bind specifically to the desired regions of receptor can also be produced in the context of chimeras with multiple species origina.

Agents that are assayed in the above method can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a non-random basis which takes into account the sequence of the target site and/or its conformation in connection with the magnet's action. As described in the Examples, there are proposed binding sites from serine protease and (catalytic) sites in the protein having SEQ ID NO: 3 or SEQ ID NO: 4. Agents can be rationally selected or rationally designed by utilizing the peptide sequences that make up these sites. For example, a rationally selected peptide agent can be a peptide whose amino acid sequence is identical to the ATP or calmodulin binding sites or domains.

The agents of the present invention can be, as examples, peptides, small molecules, and carbohydrates. A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of proteins of the invention. Antibodies agents are obtained by immunization of suitable mammalian subject with peptides, containing as antigenic regions, those portions of the protein intended to be targeted by the antibodies.

J. Pharmaceutical Compositions

The present invention further includes agents which modulate matriptase activity in a cell formulated into a pharmaceutical composition. The pharmaceutical compositions of the invention include those suitable for oral, rectal, nasal, topical (including buccal and sublingual) or parenteral (including subcutaneous, intramuscular, intravenous and intradermal) administration. The formulations may conveniently be presented in unit dosage form, e.g., tablets and sustained release capsules, and in liposomes, and may be prepared by any methods well know in the art of pharmacy. See, for example, REMINGTON'S PHARMACEUTICAL SCIENCES (18$^{th}$ ed., Mack Publ. Co. 1990).

Such preparative methods include the step of bringing into association with the molecules to be administered ingredients, such as the carrier, which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes, which render the formulation isotonic with the blood of the intended recipient; and aqueous and non-aqueous sterile suspensions, which may include suspending agents and thickening agents. The formulation may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Application of the pharmaceutical composition often will be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

It will be appreciated that actual preferred amounts of a pharmaceutical composition used in a given therapy will vary depending upon the particular form being utilized, the particular compositions formulated, the mode of application the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests.

Antibodies. The antibodies and immunogenic portions thereof of this invention are administered at a concentration that is therapeutically effective to prevent or treat any of the afore-mentioned disease states. To accomplish this goal, the antibodies may be formulated using a variety of acceptable excipients known in the art. Typically, the antibodies are preferably administered by infecting, either intravenously or intraperitoneally. Methods to accomplish this administration are known to those of ordinary skill in the art. It may also be possible to obtain compositions which may be topically or orally administered, or which may be capable of transmission across mucous membranes.

Before administration to patients, formulants may be added to the antibodies. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols, such as mono-, di- or polysaccharides, or water soluble glucans. The saccharides or glucans can include fructose, dextrose, lactose, glucose, mannose, sorbose, xylose, maltose, sucrose, dextran, pullulan, dextrain, alpha- and beta-cyclodextrin, soluble starch, hydroxyethyl starch and carboxymethylcellulose, or mixtures thereof. Sucrose is most preferred. "Sugar alcohol" is defined as a C4 to C8 hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used, as long as the sugar or sugar alcohol is soluble in the aqueous preparation. Preferably, the sugar or sugar alcohol concentration is between 1.0 w/v percent and 7.0 w/v percent, more preferable between 2.0 and 6.0 w/v percent. Preferably amino acids include levoratary (L) forms of carnitine, arginine and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP patent applications No. EP 0 270 799 and EP 0 268 110.

Additionally, antibodies can be chemically modified by covalent conjugation to a polymer to increase their circulating half-life. Preferred polymers, and methods to attach them to peptides, are shown in U.S. Pat. Nos. 4,766,106; 4,179,337; 4,495,285; and 4,609,546. Preferred polymers are polyoxyethylated polyols and polyethylene glycol (PEG). PEG is soluble in water at room temperature and has the general formula: $R(O\text{—}CH_2\text{—}CH_2)_n O\text{—}R$ where R can be hydrogen, or a protective group, such as an alkyl or alkanol group. Preferably, the protective group has between 1 and 8 carbons, more preferably it is methyl. The symbol "n" is a positive integer, preferably between 1 and 1,000, more preferably between 2 and 500. The preferred PEG ranges in molecular weight between 1,000 and 40,000, more preferably between 2,000 and 20,000, most preferably between 3,000 and 12,000. Preferably, PEG has at least one hydroxy group; more preferably it is a terminal hydroxy group. It is this hydroxy group which is preferably activated. However, it will be understood that the type and amount of the reactive groups may be varied to achieve a covalently conjugated PEG/antibody of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a forging agent in the body. The POG has a preferred molecular weight in the same range as PEG.

Another drug delivery system for increasing circulatory half-life is the liposome. Methods of preparing liposome delivery systems are discussed in Gabizon et al., *Cancer Res.* 42: 4734-9 (1982); Szoka et al., *Annu. Rev. Biophys. Bioeng.* 9: 467-508 (1980); Szoka et al., *Meth. Enzymol.* 149: 143-7 (1987); and Langne et al., *Pol. J. Pharmacol.* 51: 211-22 (1999). Other drug delivery systems are known in the art.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (e.g., Ringer's solution, distilled water, or sterile saline) which may include additional ingredients. Upon reconstitution, the composition is preferably administered to subjects using those methods that are known to those skilled in the art.

As stated above, the antibodies and compositions of this invention are used preferably to treat human patients to prevent or treat any of the above-defined disease states. The preferred route of administration is parenterally. In parenteral administration, the compositions of this invention will be formulated in a unit dosage injectable form such as a solution, suspension or emulsion, in association with a pharmaceutically acceptable parenteral vehicle. Such vehicles are inherently nontoxic and non-therapeutic. Examples of such vehicles are saline, Ringer's solution, dextrose solution, and Hanks' solution. Non-aqueous vehicles such as fixed oils and ethyl oleate may also be used. A preferred vehicle is 5% dextrose in saline. The vehicle may contain minor amounts of additives such as substances that enhance isotonicity and chemical stability, including buffers and preservatives.

The dosage and mode of administration will depend on the individual. Generally, the compositions are administered so that antibodies are given at a dose between 1 μg/kg and 20 mg/kg, more preferably between 20 μg/kg and 10 mg/kg, most preferably between 1 and 7 mg/kg. Preferably, it is given as a bolus dose, to increase circulating levels by 10-20 fold and for 4-6 hours after the bolus dose. Continuous infusion may also be used after the bolus dose. If so, the antibodies may be infused at a dose between 5 and 20 μg/minute, more preferably between 7 and 15 μg/kg/minute.

According to an equally preferred embodiment, the present invention relates to the use of a monoclonal antibody or a derivative thereof or a peptide, for the preparation of diagnostic or in vivo imaging means of any of the above-mentioned disease states.

According to a preferred embodiment an anitbody, fragments, analogs, and derivatives thereof are detectably labeled through the use of halogen radioisotopes such as $^{131}$I, $^{125}$I, metallic radionuclides $^{67}$Cu, $^{111}$In, $^{67}$Ga, $^{99}$Tc, $^{131}$I, $^{123}$I, $^{188}$Re, $^{186}$Re and $^{90}$Y etc.; affinity labels (such as biotin, avidin, etc.), fluorescent labels, paramagnetic atoms, etc. and is provided to a patient to localize the site of infection or inflammation. Procedures for accomplishing such labeling are well known to those skilled in the art. Clinical application of antibodies in diagnostic imaging are reviewed by Laurino et al., *Ann. Clin. Lab. Sci.* 29: 158-66 (1999); Unger et al., *Invest. Radiol.* 20: 693-700 (1985), and Khaw et al., *Science* 209: 295-7 (1980).

The detection of foci of such detectably labelled antibodies is indicative of a metastatic disease, tumor development or a pre-malignant lesion with metastatic potential. In one embodiment, this examination for cancer is done by removing samples of tissue (e.g., biopsy), and incubating such samples in the presence of the detectably labeled antibodies. In a preferred embodiment, this technique is done in a non-invasive manner through the use of magnetic resonance imaging (MRI), single photon emission computed tomography (SPECT) or fluorography and extracorporal detecting means, etc. Such a diagnostic test may be employed in monitoring organ transplant recipients for early signal of potential tissue rejection. Such assays may also be conducted in efforts to determine an individual's predilection to rheumatoid arthritis or other chronic inflammatory diseases.

According to another embodiment the present invention relates to the use of a monoclonal antibody or a derivative thereof, as defined above for the preparation of diagnostic and in vivo imaging means of atherosclerosis.

K. Molecular Modeling to Identify Compounds That Bind Matriptase

One method of identifying matriptase modulating compounds, and preferably matriptase inhibitors, is by using molecular modeling. Molecular modeling can be performed using the X-ray crystal structure of either the single-chain or two-chain forms of matriptase, or based on conformation information provided by the protein sequence. Specifically, as matriptase bears sequence homology to other trypsin-like molecules, the crystal structures of the other molecules (specifically trypsin) can be used to model matriptase domains. Specific sites to be targeted by inhibitors can then be studied using molecular modeling programs. Preferred sites include, but are not limited to: (1) the C1r/C1s dimerization domain or matriptase, (2) the activation site on the single-chain form of matriptase which is cleaved to form the two-chain form of matriptase, and (3) the catalytic domain of matriptase.

Molecules can be tested via molecular modeling programs to determine whether the can fit into one of the preferred sites on matriptase. Once molecules are identified which at least according to molecular modeling bind to a preferred domain, the molecules can be conveniently designed de novo by the help of three-dimensional molecular modeling computer software, such as the program called ALCHEMY-III (Tripose Associates Inc.; St. Louis, Mo.). In the case of peptide compounds, it is now possible to determine the influence and relative importance of specific amino acid residues on receptor or antigen binding, using such tools as magnetic resonance spectroscopy and molecular modeling, allowing the specific design and synthesis of peptides which bind a known antigen, antibody or receptor, or which mimic a known binding sequence or ligand.

Biological-Function Domain. The biological-function domain of the constructs is a structural entity within the molecule that binds the biological target and may either inhibition of activation of the single-chain matriptase to the two-chain, active form of matriptase or may inhibit the two-chain, active form of matriptase from binding to its normal substrate(s). For peptides which can form a ligand and receptor pair, in which the receptor is not a biological target, the discussions pertaining to a biological-function domain apply unless expressly limited to biological systems. The biological-function domain of the peptide includes the various amino acid side chains, arranged so that the domain binds stereospecifically to, for example, the activation site of matriptase or the proteolytic active site of matriptase in its active, two-chain form. The biological-function domain may be either be sychnological (with structural elements placed in a continuous sequence) or rhegnylogical (with structural elements placed in a discontinuous sequence), as such concepts are described generally in Schwyzer, *Biopolymers* 31: 875-792 (1991).

After purification, crystallization and isolation, the subject crystals may be analyzed by techniques known in the art. Typical analysis yield structural, physical, and mechanistic information about the peptides. As discussed above, X-ray crystallography provides detailed structural information that may be used in conjunction with widely available molecular modeling programs to arrive at the three-dimensional arrangement of atoms in the peptide.

Peptide modeling can be used to design a variety of agents capable of modifying the activity of the subject peptide. For example, using the three-dimensional structure of the active site, matriptase agonists and antagonists having complementary structures can be designed to block the biological activity of matriptase. Further, matriptase structural information is useful for directing design of proteinaceous or non-proteinaceous matriptase modulating agents, based on knowledge of the contact residues between the matriptase and its substrate.

Computer modeling can also be performed as described in Example 4, or using nuclear magnetic resonance (NMR) or X-ray methods (Fletterick et al., eds., "Computer Graphics and Molecular Modeling," in Current Communications in Molecular Biology (Cold Spring Harbor Laboratory, Cold Spring Harbor, N.Y., 1986). Exemplary modeling programs include "Homology" by Biosym (San Diego, Calif.), "Biograf" by BioDesign, "Nemesis" by Oxford Molecular, "SYBYL™" and "Composer" by Tripos Associates, "CHARM" by Polygen (Waltham, Mass), "AMBER" by University of California, San Francisco, and "MM2" and "MMP2" by Molecular Design, Ltd.

EXAMPLES

Example 1

Purification and Characterization of a Complex Containing Matriptase and a Kunitz-Type Serine Protease Inhibitor These data as described in Lin et al., *J. Biol. Chem.* 274(26): 18237-42 (1999), which investigates the role of matriptase under physiological conditions such as differentiation and lactation.

Cell lines and culture condition: Four milk-derived, immortalized luminal mammary epithelial cell lines (MTSV-1.1B, MTSV-1.7, MRSV-4.1, and MRSV-4.2) were a gift from Dr. J. Taylor-Papadimitriou (ICRF, London) (Bartek et al., *Proc. Natl. Acad. Sci. USA* 88: 3520-24 (1991)), and were maintained in modified Iscove's minimal essential medium (Biofluids, Rockville, Md.) supplemented with 10% fetal calf serum (GIBCO), bovine insulin at 10 μg/ml, hydrocortisone (Sigma) at 5 μg/ml, and antibiotics. Human foreskin fibroblasts and the fibrosarcoma cell line, HT-1080 (from American Type Culture Collection, ATCC) were maintained in modified Iscove's minimal essential medium supplemented with 10% fetal calf serum (GIBCO). To collect cell conditioned medium, monolayers of these cells at confluency were washed twice with phosphate-buffered buffered saline (PBS) and were cultured for two days in the absence of the serum in modified Iscove's minimal essential medium supplemented with insulin/transferrin/selenium (Biofluids).

Identification and partial isolation of matriptase-related proteases from human milk: To isolate matriptase-related proteases, 1.5 liters of frozen human milk from Georgetown University Medical Center Milk Bank was thawed and centrifuged to remove the milk fat and insoluble debris. Ammonium sulfate powder was added to the milk with continuous mixing to 40% saturation, and allowed to precipitate in a cold room for at least 2 hours. Protein precipitates were obtained by centrifugation at 5,000×g for 20 min. The pellets were saved, and the supernatant was further precipitated by addition of ammonium sulfate powder to 60% saturation. The protein pellets were dissolved in water, and then dialyzed against 20 mM Tris-Hcl, pH 8.0 for DEAE chromatography or against 10 mM phosphate buffer, pH 6.0 for CM chromatography. Insoluble debris was cleared by centrifugation, and the supernatant was divided into five batches. Each batch was loaded onto a DEAE Sepharose FF column (2.5×20 cm) (Pharmacia; Piscataway, N.J.), equillibrated with 20 mM Tris-HCl, pH 8.0. The column was washed with 10 column volumes of equilibration buffer. Bound material was eluted with a linear gradient from 0-1 M NaCl in DEAE equilibration buffer with a total volume of 500 ml. Fractions (14 ml) were collected and assessed by immunoblot using mAb 21-9. To perform CM chromatography, the 95-kDa fraction from DEAE chromatography or the precipitate derived directly from ammonium sulfate precipitation was dialyzed against 10 mM phosphate buffer, pH 6.0. Insoluble debris was cleared by centrifugation and the supernatant was loaded onto a CM Sepharose FF column (2.5×20 cm) (Pharmacia; Piscataway, N.J.), equillibrated with 10 mM phosphate buffer, pH 6.0. The column was washed with 10 column volumes of equilibration buffer. Bound material was eluted with a linear gradient from 0-0.5 M NaCl in 10-MM phosphate buffer, pH 6.0 with total volume of 500 ml. 14 Milliliter fractions were assessed by immunoblot using mAb 21-9.

Immunoaffinity chromatography: Preparation of an immunoaffinity column coupling mAb 21-9 to Sepharose 4B (5 mg of IgG/ml of beads) was performed using CNBr-activated Sepharose 4B, as previously described (Lin et al. *J. Biol. Chem.* 272: 9147-52 (1997)). Partially purified 95-kDa matriptase complex from DEAE or CM chromatography was loaded onto a 1-ml column at a flow rate of 7 ml/h. The column was washed with 1% Triton X-100 in PBS. Bound protease was then eluted using 0.1 M glycine-HCl (pH 2.4). Fractions were immediately neutralized using 2 M Trizma base.

Immunization and hybridoma fusion: Two six week old female Balb/c mice were immunized with matriptase complexes (10 μg per dose) at intervals of 2 weeks. Complete Freund's adjuvant was used for the initial immunizations, while incomplete adjuvant was used for boosts. Three days after the second boost, antiserum was collected from the tail vein, and the immunoresponse was determined by immunoblot. The final boost was conducted with the matriptase complex in the absence of adjuvant by tail vein injection. The spleenocytes were collected and fused with mouse myoloma cells (SP2 or NS1) by polyethylene glycol (PEG) methodology, and the successful hybridoma cells were selected by HAT medium (Kilmartin et al., *J. Cell. Biol.* 93: 576-82 (1982)).

Hybridoma screening: The primary screening was carried out by western blot using the targets that contain a mixture of intact 95-kDa matriptase complex, dissociated matriptase, and the binding proteins. More than one hundred positive clones were selected in the primary screening. Three anti-matriptase mAbs (M32, M92, and M84) and two anti-binding protein mAbs (M19 and M58) were selected and characterized in detail.

Monoclonal antibody preparation: To produce mAbs, hybridoma lines were gradually adapted to low serum-supplemented culture medium and then to protein free hybridoma medium (Gibco). Monoclonal antibodies were harvested and precipitated by 50% saturation with ammonium sulfate. Further purification was carried out be DEAE chromatography.

Immunoblotting analysis: Immunoblot was conducted as previously described (Lin et al., (1997)). Proteins were separated by 10% SDS-PAGE, transferred to polyvinylidene fluoride (PVDF), and probed with mAbs as specified. Immunoreactive polypeptides were visualized using peroxidase-labeled secondary antibody and the ECL detection system (Amersham Corp.; Arlington Heights, Ill.).

Diagonal SDS-PAGE: The 95-kDa matriptase complex preparation was resolved by SDS-PAGE under non-boiled conditions; the gel strip was sliced out, boiled in 1X SDS sample buffer, placed on an SDS-acrylamide gel without wells, and electrophoresed under the same conditions as the first dimension gel. Protein bands were stained by Colloidal Coomassie (Neuhoff et al., *Electrophoresis* 9: 255-62 (1988)), due to the negative image observed with silver stain.

Amino Acid Sequence analysis of the 40- and 25-kDa binding proteins: The 40- and 25-kDa binding proteins were purified as described above. The amino-terminal sequence of these proteins were determined (Matsudaira, *J. Biol. Chem.* 262: 10035-8 (1987)). Twelve (from 40-kDa protein) and seven (from 25-kDa protein) amino acid residues obtained were identical to the deduced amino acid sequences of an inhibitor of hepatocyte growth factor activator I (HAI-1) (Shimomura et al., *J. Biol. Chem.* 272: 6370-6 (1997)). To further confirm the identity of the binding protein to be HAI-1, the larger band from the 40-kDa protein doublet was subjected to in gel digestion and then to analysis by the matric assisted laser desorption ionization mass spectrometry (MALDI-MS) at HHMI Biopolymer Laboratory & W. M. Keck Foundation Biotechnology Resource Laboratory at Yale University.

Expression of HAI-1 in COS-7 cell: To verify that HAI-1 encodes the binding protein of matriptase, we isolated an HAI-1 cDNA fragment by reverse transcriptase-polymerase chain reaction (RT-PCR) utilizing mRNA from MTSV 1.1 B immortalized human luminal mammary epithelial cells. Primer sequences for HAI-1 (5'-GGCCCGCGCTCT-GAAGGTGA-3' (SEQ ID NO: 28) and 5'-TTGGCAAG-CAGGAAGCAGGG-3') (SEQ ID NO: 29) were derived from the published sequence. Standard RT-PCR was carried out using the Advantage RT-PCR kit (Clontech; Palo Alto, Calif.), and the product was ligated into pCR2.1 (Invitrogen; Carlsbad, Calif.) by TA cloning. The sequence of the RT-PCR product was obtained by standard methods, and confirmed with the published HAI-1 sequence (Miyazawa et al., *J Biol. Chem.* 268: 10024-8 (1993)). An eukaryotic expression vector was constructed (pcDNA/HAI-1), utilizing the commercially available pcDNA3.1 vector (Invitrogen; San Diego, Calif.), A 1.6 kb EcoRI fragment containing the HAI-1 cDNA was cloned into the EcoRI site of pcDNA 3.1. This construct contains the open reading frame (ORF) of HAI-1 derived by a CMV promoter. Correct insertion of the HAI-1 cDNA was verified by restriction mapping. Transfections were performed using SuperFect transfection reagent (QIAGEN; Valencia, Calif.) as specified in manufacturer's handbook. After 48 hr, the HAI1 -transfected COS-7 cells were extracted with 1% Triton-X100 in 20 mM Tris-HCl pH 7.4.

Figure 1:
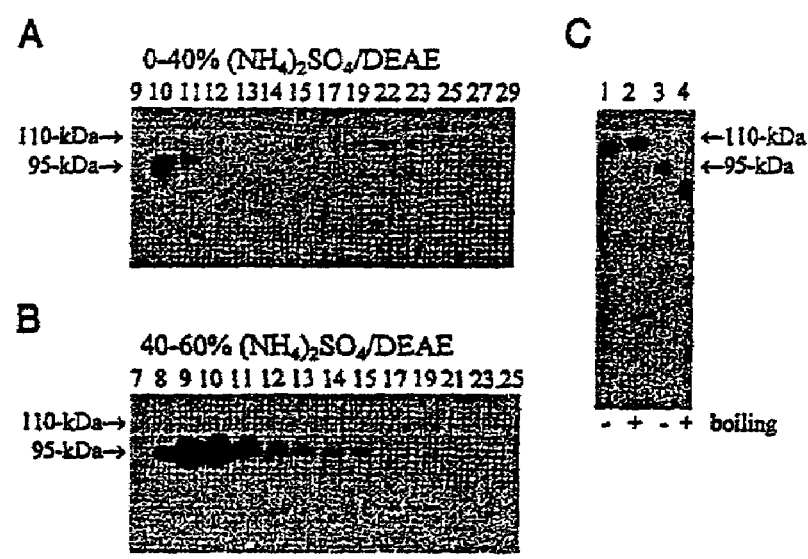
FIG. 1: Identification and Partial Purification From Human Milk of 110-and 95-kDa Proteins Immunoreactive to Anti-Matriptase mAb 21-9

Matriptase-related proteases in human milk: Previously, matriptase was observed to exist either in a major, uncomplexed form or in two minor SDS_stable (Lin et al., (1997)), complexed forms with apparent molecular masses of 110- and 95-kDa. The matriptase binding protein(s) was not identified. To identify those binding protein(s), we have examined the matriptase complexes found in human milk. Our hypothesis has been that the binding protein is a protease inhibitor and that its expression may be associated with a specific physiological status, such as differentiation or lactation. In human milk, two immunoreactive bands of 95- and 110-kDa in size, but no uncomplexed matriptase was detected by anti-matriptase mAb 21-9 under non-boiled and non-reduced conditions (FIG. 1). The 95-kDa band was the predominant species; the relative amount of the minor, 110-kDa band varied between different batches of milk (FIGS. 1A and B). In common with a 95-kDa immunoreactive matriptase complex previously identified in human breast cancer cells (Lin et al., (1997)), the milk-derived 95-kDa immunoreactive species was converted, after boiling in the absence of reducing agents, to a smaller immunoreactive band. This band corresponds in size to the previously described, uncomplexed matriptase from breast cancer (FIG. 1C). Thus, matriptase appeared to be a component of the 95-kDa complex, both in breast cancer cells and in milk. Although most of the matriptase in breast cancer cells is uncomplexed, the opposite is true in milk.

Most of the minor, 110-kDa immunoreactive polypeptide in milk was precipitated by a 40% saturation of ammonium sulfate. This band was then separated from the major 95-kDa matriptase complex by DEAE chromatography (FIG. 1A). In contrast to the 95-kDa matriptase complex, the milk-derived 110-kDa immunoreactive polypeptide had a reduced rate of migration on an SDS-polyacrylamide gel after boiling (FIG. 1, panel C). These results suggest that this milk-derived 110-kDa immunoreactive polypeptide is not likely to be a protease complex. The 110-kDa species from breast cancer cells was converted by boiling into matriptase and another unidentified species (Lin et al., (1997)). This milk-derived 110-kDa species was thus distinct from the 110-kDa matriptase complex previously isolated from breast cancer T-47D cells.

Purification of matriptase complexes from human milk: The milk-derived 95-kDa matriptase complex has been isolated using an anti-matriptase mAb-21-9 immunoaffinity column. This highly purified 95-kDa matriptase complex an be converted to matriptase after boiling in conjunction with appearance of a protein doublet with apparent molecular mass of 40-kDa (Lin et al., *J. Biol. Chem.* 274: 18231-6 (1999)). In some batches of milk, in addition to the 95-kDa complex, another protease complex doublet, with apparent molecular mass of 85-kDa, was also observed (FIG. 2, lane 1). Both 95- and 85-kDa matriptase complexes were converted to matriptase after boiling. In addition to matriptase, a 40-kDa and a 25-kDa protein bands were observed (FIG. 2, lane 2).

Biochemical and immunological approaches have been taken to prove the 40- and 25-kDa bands to be components of matriptase complexes. In our biochemical approach, a 95-kDa matriptase complex preparation, which also contains low levels of uncomplexed matriptase, was subjected to a non-boiling/boiling diagonal gel electrophoresis. In this gel electrophoresis system, proteins whose migration rate on an SDS polyacrylamide gel are not changed by boiling will be seen on the diagonal line. In contrast, heat-sensitive complexes will be dissociated into their constituent subunits and will be seen on the same electrophoretic path below the diagonal line; proteins whose configuration is changed by boiling resulting in a lower migration rate will be seen beyond the diagonal line. The sample was firstly resolved by SDS-PAGE and a strip of gel was sliced off. The sliced gel strip was boiled in 1X SDS sample buffer in the absence of reducing agents, placed on a second SDS polyacrylamide gel, and electrophoresed (FIG. 3). In the case of the 95-kDa matriptase complex, both the 40-kDa protein doublet and matriptase were observed below the diagonal line and on the same electrophoretic path (FIG. 3). This result thus configured that matriptase and the 40-kDa doublet were components of the 95-kDa protease complex. On the other hand, uncomplexed matriptase was seen on the diagonal line (FIG. 3).

In an immunological approach, a panel of mAbs was obtained using matriptase complexes as immunogens (FIG. 4). A new antimatriptase, antibody mAb M92, recognizes both 95- and 85-kDa matriptase complexes under non-boiling conditions (FIG. 4A, lane 5). This mAb recognizes uncomplexed matriptase, but not the 40- and 25-kDa bands after boiling, (FIG. 4A, lane 6). Monoclonal antibody, M19, recognizes both matriptase complexes under non-boiling conditions (FIG. 4A, lane 3), but not the uncomplexed matriptase under boiling conditions (FIG. 4A, lane 4). However, M19 detects both 40- and 25-kDa bands after boiling (FIG. 4A, lane 4).

A third antibody type, mAb M58, was also selected. This mAb selectively recognizes only the 95-kDa matriptase complex but not the 85-kDa complex under non-boiling conditions (FIG. 4A, lane 1); mAb M58 recognizes only the 40-kDa band but not the 25-kDa band after boiling, (FIG. 4A, lane 2). These results, combined with the results in FIG. 2, suggest that the 95-kDa matriptase complex is composed of matriptase and a 40-kDa component. The 85-kDa matriptase complex is composed of matriptase and the 25-kDa component. The 25-kDa component is likely to be a degraded product of the 40-kDa component. The epitope recognized by mAb M19 resides on both 40 and 25-kDa components, but the one recognized by mAb M58 residues only on the 40-kDa component. In FIG. 4 panel B, we summarize the structures of both 95- and 85-kDa matriptase complexes and their interactions with these mAbs.

The binding proteins of the matriptase are fragments of a Kunitz-type serine protease inhibitor: When the amino-terminal sequences of the 40- and 25-kDa binding proteins were determined, the sequences of the 40-kDa binding protein (e.g., GPPPAPPGLPAG) were found to be identical to the amino-terminal sequences of a Kunitz-type serine protease inhibitor (Shimomura et al., *J. Biol. Chem.* 272: 6370-76 (1997)), which was previously identified as an inhibitor of hepatocyte growth factor activator (HAI-1) (Shimomura et al., (1997); the amino acid residues (e.g., TQGFGGS) obtained from the N-terminus of the 25-kDa binding protein are identical to the sequences from residue 154 through residue 160 of HAI-1 (Shimomura et al., (1997)). To further confirm that the binding proteins of matriptase are identifiable as HAI-1, the larger band from the 40-kDa doublet was subjected to in gel trypsin digestion. The tryptic digests were examined by matrix assisted laser desorption ionization mass spectrometry (MALDI-MS). Twelve unique peptides from the tryptic digests were matched to the HAI-1 sequence by searching the observed MALDI-MS masses from the binding protein to the HAI-1 (FIG. 5). These 12 peptides cover 87 residues that span residues 135-310. These results indicate that the binding proteins of matriptase are fragments of HAI-1.

In another study, the immunoreactivity of anti-binding protein mAb with HAI-1 that was expressed by HAI-1 transfected COS-7 cells (FIG. 6). Anti-binding protein mAb M19 detected a band with apparent size of 55-kDa in the cell lysate of HAI-1 transfected COS-7 cells (FIG. 6, lane 2) and in the 2 M KCl-washed membrane fraction of T-47D human breast cancer cells (FIG. 6, lane 4), but not in the COS-7 cells (FIG. 6, lane 3), nor in matriptase-transfected COS-7 cells (FIG. 6, lane 1). The immunoreactivity between anti-binding protein mAb and HAI-1 gene product provides a second line of evidence that the binding protein of matriptase is HAI-1. Because this size of the immunoreactive 55-kDa band is close to the calculated molecular mass (53,319 Da) of mature, membrane-bound HAI-1, and because its associated ion with membrane fraction is sufficiently strong that it resists dissociation by washing with 2 M KCl, this 55-kDa band is considered likely to be the mature, intact HAI-1.

Mammary epithelial production of matriptase and the Kunitz-type protease inhibitor: To investigate the possible cell types which release matriptase and its complexes, we examined their expression in four milk-derived, Simian virus 40 large tumor antigen immortalized luminal epithelial cell lines (milk cells) (Bartek et al., *Proc. Natl. Acad. Sci. USA* 88: 3520-24 (1991)), two cultured human foreskin fibroblasts, and a fibrosarcoma cell line HT-1080 (FIG. 7). Positive results for the mammary luminal epithelial cells (FIG. 7, lanes 4-11) and negative results for the fibroblasts and HT-1080 fibrosarcoma cells (FIG, 7, lanes 1-3) suggest that the protease and its binding protein are produced by the epithelial components of the lactating mammary gland. In contrast to milk, the immortalized, mammary luminal epithelial cells expressed detectable, uncomplexed matriptase and an 100-kDa complex. This 110-kDa complex species was not detected in milk, but was detected in T-47D breast cancer cells (Lin et al., (1997)).

Example 2

Molecular Cloning and Characterization of Matriptase

This example describes the further isolation of matriptase protein and the gene encoding it as described by Lin et al., *J. Biol. Chem.* 274: 18231-6 (1999).

Cell lines and culture conditions: COS-7 cells were maintained in modified Iscove's minimal essential medium (Biofluids, Inc.; Rockville, Md.) supplemented with 5% fetal calf serum (Life Technologies, Inc.).

Purification of Matriptase: To obtain enough matriptase for amino acid sequencing, the enzyme was isolated from human mile (Lin et al., *J. Biol. Chem.* 274: 18237-42 (1999)). Briefly, human milk from the Georgetown University Medical Center Milk Bank was precipitated and collected by addition of ammonium sulfate between 40 and 60% saturation. Matriptase wasp purified by a combination of CM-Sepharose and immunoaffinity chromatography.

Amino Acid Sequence analysis: To obtain internal amino acid sequences, purified matriptase was separated by SDS-PAGE, lightly stained with Coomassie blue, and protein bands were excised. Matriptase was then subjected to in gene digestion and amino acid sequencing at HHMI Biopolymer Laboratory & W. M. Keck Foundation Biotechnology Resource Laboratory at Yale University. The aminoterminal sequences were determined as described previously (Matsudaira et al., *J. Biol. Chem.* 262: 10035-8 (1987)). Briefly, the proteins were resolved by SDS-PAGE, transferred to polyvinylidene, difluoride membrane, and lightly stained with Coomassie blue. The proteins were excised and subjected to amino-terminal sequencing (Chemistry Department, Florida State University, Tallahassee, Fla.). The two short sequences obtained were identical to a deduced amino acid sequence termed SNC19 (GenBank Accession NO. U20428).

Amplification of an SNC19 CDNA from T-47D breast cancer cells: AN SNC19 cDNA clone was generated by reverse transcriptase-polymerase chain reaction (RT-PCR) utilizing mRNA from T-47D human breast cancer cells.

Primer sequences for SNC19 (5'-CCTCCTCTTGGTCT-TGCTGGGG-3' (SEQ ID NO: 30) and 5'-AGACCCGTCT-GTTTTCCAGG-3') (SEQ ID NO: 31) were derived from the published sequence. Standard RT-PCR was conducted using the Advantage RT-PCR kit (Clontech; Palo Alto, Calif.). Products were analyzed on a 0.8% agarose gel and the resultant band of approximately 2.8 kb corresponding to the expected product size was excised from the gel, purified and ligated into pCR2.1 (Invitrogen, Carlsbad, Calif.) by TA cloning (pCR-SNC19).

Sequencing: DNA sequencing was performed on a Perkin Elmer Applied Biosystem automated 377 DNA sequencer (Foster City, Calif.) using standard methods with the assistance of the Lombardi Sequencing and Synthesis Shared Resource. The sequences were assembled and analyzed with Lasergene software for windows (DNA Star Inc.; Madison, Wis.). The predicted protein sequence was compared to sequences in Swiss-Prot© database at the National Center for Biotechnology Information using the BLAST network server.

Expression of SNC19 in COS-7 cell: To verify the SNC19 encodes the matriptase gene, we constructed an eukaryotic expression vector (pcDNA/SNC19) utilizing the commercially available pcDNA 3 vector (Invitrogen; San Diego, Calif.). A 2.83 kb EcoRI fragment containing the SNC 19 cDNA was produced by digestion of pCR-SCN19 and cloned into the EcoRI site of pcDNA 3. This construct contains the open reading frame of SNC 19 drive by a CMV promoter. Correct insertion of the SNC19 cDNA was verified by restriction mapping (data not shown). Transfections were carried out using SuperFect™ transfection reagent (QIAGEN; Valencia, Calif.), as specified in manufacturer's handbook. After 48 hr, the matriptase-transfected COS-7 cells and the control COS-7 cells, which were transfected with LacZ to monitor transfection efficiency, were extracted with 1% Triton-X100 in 20 mM Tris-HCl pH 7.4.

Immunoblotting analysis: Immunoblot was conducted as previously described (Lin et al., *J. Biol. Chem.* 272: 9147-52 (1997)). Proteins were separated by 100% SDS-PAGE, transferred to polyvinylidene fluoride membrane, and subsequently probed with anti-matriptase monoclonal antibody (mAB) M32. Immunoreactive polypeptides were visualized using peroxidase-labeled secondary antiserum and the ECL detection system (Amersham Corp.; Arlington Heights, Ill.).

Gelatin zymography: Gelatin zymography was carried out as previously described with some modifications (Brown et al., *Biochem J.* 101: 214-228 (1966)). Gelatin (1 mg/ml), as a substrate, was copolymerized with regular SDS-polyacrylamide gel. Electrophoresis was performed at a constant current of 15 mA. The gelatin gels were washed 3 times with PBS containing 2% Triton X-100 and incubated in PBS at 37° C. overnight.

Cleavage of Synthetic Substrates: To demonstrate the trypsin-like activity of matriptase, various synthetic fluorescent protease substrates with arginine or lysine as the P1 site were tested with purified matriptase from human mil, Matriptase was assayed in 20 mM tris buffer, pH 8.5, at 25° C. in a volume of 190 μl prior to addition to 10 μl of 2 mM substrate solution (to a final concentration of 0.1 mM). These substrates included t-butyloxycarbonyl (Boc)-Gln—Ala—Arg-7-amino-4-methylcoumarin (AMC), Boc-benzyl-Glu—Gly-Arg—AMC, Boc—Leu—Gly—Arg—AMC, Boc-benzyl—Asp—Pro—Arg—AMC, Boc—phe—Ser—Arg—AMC, Boc—Val—Pro—Arg—AMC, succinyl-Ala—Phe—Lys—AMC, Boc—Leu—Arg—Arg—AMC, Boc—Gly, Lys—Arg—AMC, and Boc—Leu—Ser—Thr—Arg—AMC. These substrates were purchased from Sigma. The rate of cleavage of individual substrates was determined against time with a Hitachi F-4500 fluorescence spectrophotometer.

Results: In further studies, and referring specifically to FIG. 8, the partially purified 95-kDa matriptase complex from ion exchange chromatography was loaded onto a mAb 21-9-Sepharose column. The bound proteins were eluted by glycine buffer, pH 2.4, and neutralized by addition of 2 M Trizma base. The eluted proteins were incubated in 1X SDS sample buffer in the absence of reducing agents at room temperature (lanes 1, each panel, boiling −) or 95° C. (lanes 2, each panel, boiling +) for 5 min. The samples were resolved by SDS-PAGE and either stained by colloidal Coomassie (pane A), subjected to immunoblot analysis using mAb 21-9 (panel B), or subjected to gelatin zymography (panel C). The 95-kDa matriptase complex was eluted from this affinity column as the major protein (panel A, lane 1); it was recognized by mAb 21-9 (panel B, lane 1), and it also exhibited gelatinolytic activity (panel C, lane 1). The 95-kDa matriptase complex was converted to matriptase by boiling (panel A, lane 2). The gelatinolytic activity of the 95-kDa protease was destroyed by boiling, but a low level of the gelatinolytic activity survived and converted to matriptase (panel C, lane 2). A low level of uncomplexed matriptase was co-purified with the 95-kDa matriptase complex by affinity chromatography (panel A, lane 1); it also exhibited gelatinolytic activity (panel C, lane 1). Immunoblot analysis enhanced the signal of the uncomplexed matriptase and reconfirmed its existence (panel B, lane 1). Several other polypeptides were also seen (panel A, lanes 1 and 2). Some of them could be the degraded products of the protease, since they were recognized by mAb 21-9 after longer exposure to the X-ray film. A 40-kDa protein doublet was seen in low levels in a non-boiled sample (panel A, lane 1), but its levels were increased after boiling (panel A, lane 2). This 40-kDa doublet was not recognized by mAb 21-9 (panel B). We propose that these two polypeptides could be binding proteins of matriptase. In the figure, MW stands for the molecular weight markers; their sizes are as indicated.

Although sequence analysis of the 40-kDa binding protein has shown it to be a serine protease inhibitor (see below), some residual gelatinolytic activity was observed for the 95-kDa matriptase/inhibitor complex (FIG. 8C). When matriptase and its binding protein were subjected to N-terminal sequencing, only 11 amino acid residues (VVGGT-DADEGE) (SEQ ID NO: 32) from matriptase were obtained with relatively low recover, and 12 amino acid residues (GPPPAPPGLPAG) (SEQ ID NO: 2) were obtained from the amino-terminus of the 40-kDa binding protein. The 11 amino acid residues from matriptase were identical to a deduced amino acid sequence from a 2.9 kb cDNA called SNC19 (accession number U20428). Numerous stop codons were observed in this deposited SNC19 sequence, resulting in several small, predicted translation products. Thus, a 2,830 bp cDNA fragment was obtained by reverse transcriptase-polymerase chain reaction using two primers based on the sequence of SNC 19. There was extensive discrepancy (132 bases) between our sequence and that of SNC19.

Verification of SNC19 cDNA encoding matriptase: In addition to the sequence identity of matriptase with portion of SNC19, the immunoreactivity of anti-matriptase mAbs to the SNC19 gene product were examined to verify whether SNC19 encodes matriptase. SNC19 cDNA was inserted into the eukaryotic expression vector pcDNA3.1 and transfected into COS-7 monkey kidney fibroblasts, which do not express matriptase. A strong, immunoreactive band with the same size of matriptase from T-47D human breast cancer cells detected by anti-matriptase mAb M32 was observed in SNC-19 transfected COS-7 cells, but not in control COS-7 cells.

Nucleotide and predicted amino acid sequences of an matriptase cDNA clone: A Nucleotide (SEQ ID NO: 4) and an amino acid sequence (SEQ ID NO: 5) of matriptase are shown in FIG. 9. The primers (20 bases at 5' end and 18 bases at 3' end) used for reverse transcriptase-polymerase chain reaction are underlined. Thirty three bases beyond the 51 end primer and 92 bases beyond 31 end primer were taken from SNC 19 cDNA and incorporated. The cDNA sequence was translated from the fifth ATG (Met) codon in the open reading frame. Nucleotide and amino acid numbers are shown on the left. Double-underlines indicate sequences that agreed with the internal sequences obtained from matriptase. His-484, Asp-539 and Ser-633 were boxed and indicated the putative catalytic triad of matriptase. Potential N-glycosylation sites are indicated by Δ. A RGD sequence is indicated by ♠.

Matriptase cDNA is likely to be 2955 base pair long when the 5' end 33 bases and the 3' end 92 bases from SNC 19 were added to the RT-PCR fragment (2,830 base pair long). The translation initiation site was assigned to the fifth methionine codon because the sequence GTCATGG matches a favorable Kozak consensus sequence (Kozak et al., Nucl. Acid. Res. 12: 857-72 (1984)). This methionine is followed by four positively charged amino acids and a 14 amino acid long hydrophobic region (Ser-18-Ser-31), a putative signal peptide. Assuming this methionine codon to be the initiator, the open reading frame was 2,049 base pairs long, and thus the deduced amino acid sequence was composed of 683 residues, with calculated molecular mass of 75,626. The two stretches of amino acid sequences (DYVEINGEK (SEQ ID NO: 33) and VVGGTDADEGE (SEQ ID NO: 32) obtained from matriptase are located in aa 228-236 and aa 443-453; thus the translation frame is likely to be correct. There are three potential N-glycosylation sites with the canonical Asn-X-(Ser/Thr) and an RGD sequence. RGD sequence from proteins of the extracellular matrix has been found to mediate interactions with integrins (Ruosiabti et al., Science 238: 491-7 (1987)).

Structure of the matriptase catalytic domain: A homology search for the deduced amino acid sequence by BLAST in the Swiss-Prot© data base reveals that (1) the carboxyl-terminus at residue positions 432-683 of matriptase (SEQ ID NO: 5) is homologous with other serine proteases; (2) matriptase contains the invariant catalytic triad; (3) matriptase contains a characteristic disulfide bond pattern; and (4) matriptase contains overall sequence similarity. Referring to FIG. 9, the primers (20 bases at 5' end (SEQ ID NO: 30) and 18 bases at 3' end (SEQ ID NO: 31, complement) used for reverse transcriptase-polymerase chain reaction are underlined. Thirty-three bases beyond the 5' end primer and 92 bases beyond 3' end primer were taken from SNC 19 cDNA and incorporated. The cDNA sequence was translated from the fifth ATG codon in the open reading frame. Nucleotide and amino acid numbers are shown on the left. Double-underlines indicate sequences that agreed with the internal sequences obtained from matriptase. His-484, Asp-539, and Ser-633 were boxed and indicated the putative catalytic triad of matriptase. Potential N-glycosylation sites are indicated by Δ. A RGD sequence is indicated by ♠.

Compared with the archetype serine protease, chymotrypsin (Hartley et al., Biochem J. 101: 229-31 (1966); and Brown et al., Biochem J. 101: 214-28 (1966)) and other serine proteases, the three amino acids (His-484, Asp-539, and Ser-633) are likely to correspond to those in chymotrypsinogen (His-57, Asp-102, and Ser-195) and are likely to be essential for catalytic activity (Hartley et al., Nature 207: 1157-9 (1965)). The six most conserved cysteines needed to form three intramolecular disulfide bonds that stabilize the catalytic pocket have been determined in other chymotrypsin-related proteases. The most likely cysteine pairings in matriptase are: Cys-469-Cys-485, Cys-604-Cys-618, and Cys-629-Cys-658. Matriptase also contains two additional cysteines (Cys-432-Cys-559) which correspond to those used in two-chain proteases, such as enteropeptidase (Kitamoto et al., Proc. Natl. Acad. Sci. USA 91: 7588-92 (1994)), hepsin (Leytus et al., Biochemistry 27: 1067-74 (1988)) plasma kallikrein (Chung et al., Biochemistry 25: 2410-17 (1986)), blood coagulation factor XI (Fujikawa et al., Biochemistry 25: 2417-24 (1986)), and plasminogen (Forsgren et al., FEBS Lett. 213: 254-50 (1987)), but not in trypsin (Emi et al., Gene (Amst.) 41: 305-310 (1986)), or chymotrypsin (Tomita et al., Biochem. Biophys. Res. Commun. 158: 569-75 (1989)) (FIG. 10).

Referring more specifically to FIG. 10, the C-terminal region (aa 431-683) of matriptase (SEQ ID NO: 6) is compared with human trypsin (SEQ ID NO: 13), human chymotrypsin (SEQ ID NO: 14), the catalytic chains of human enteropeptidase (SEQ ID NO: 7), human hepsin (SEQ ID NO: 10), human blood coagulation factor XI (SEQ ID NO: 11), and human plasminogen (SEQ ID NO: 12), and the serine protease domains of two transmembrane serine proteases, human TMPRSS2 (SEQ ID NO: 8) and Drosophila Stubble-stubbloid gene (Sb-sbd) (SEQ ID NO: 9). Residues are expressed in one letter code. Gaps to maximize homologies are indicated by residues in the catalytic triads (matriptase His-484, Asp-539, and Ser-633) were boxed and indicated by ♦. The conserved activation motif (R/KVIGG) (SEQ ID NO: 34) was boxed and the proteolytic activation site was indicated. Eight conserved cysteines needed to form four intramolecular disulfide bonds are boxed, and the likely pairings are as follows: Cys-469-Cys-485, Cys-604-Cys-618, Cys-629-Cys-658, and Cys-432-Cys-559. The disulfide bond ((Cys-432-Cys-559) is observed in two-chain serine proteases, but not in trypsin and chymotrypsin. Residues in the substrate pocket (Asp-627, Gly-655, and Gly-665) are boxed and indicated by Φ. It is evident that the residue positioned at the bottom of substrate pocket in Asp in trypsin-like proteases, including matriptase, but is Ser in chymotrypsin.

A putative proteolytic activation site (Arg-442) of matriptase in a motif of Arg—Val-—Var—Gly—Gly (RV-VGG) (SEQ ID NO: 35) is similar to the characteristic RIVGG (SEQ ID NO: 36) motif in other serine proteases. However, the Ile residue is replaced by Val residue. This replacement is uncommon, but is observed in plasminogen. As mentioned above, a conserved intramolecular disulfide bond is found in those serine proteases that are synthesized as one-chain zymogens and are proteolytically activated to become active two chain forms. This disulfide bond is proposed to hold together the active catalytic fragment with their non-catalytic N-terminal fragments, thus serving as protein-protein interaction domain. This conserved intramolecular disulfide bond has been also observed in matriptase (Cys-432-Cys-559). These sequence analyses suggest that matriptase may be synthesized as a single chain zymogen and may become proteolytically activated to a two-chain form. If this is a case, the majority of matriptase in the conditioned medium of T-47D breast cancer cells is likely to be the zymogen; the active two-chain matriptase only represents a minor proportion, constituent with the purified matriptase from T-47D human breast cancer cells exhibiting an apparent size of 80-kDa under reduced conditions. This conclusion is also supported by the observation that the proposed N-terminal sequences for the catalytic chain of matriptase are identical to the stretch of amino acid sequences (VVGGTDADEGE) (SEQ ID NO: 37), which were obtained with very low recovery when matriptase was subjected to N-terminal sequencing.

The substrate specificity ($S_1$) pocket of matriptase is likely to be composed of Asp-627 positioned at its bottom, with Gly-655 and Gly-665 at its neck, indicating that matriptase is a typical trypsin-like serine protease. Predicated preferential cleavage at amino acid residues with positively charged side chains was configured with various synthetic substrates with Arg and Lys residues as PI sites. Specifically, matriptase was able to cleave the following synthetic substrates, presented as follows, from the most rapid to the slowest: Boc—Gin—AlaArg—AMC. Boc-benzy-Glu—Gly—Arg—AMC, Boc—Leu—Gly—Arg—AMC, Bocbenzyl-Asp—Pro—Arg—AMC, Boc—Phe—Ser—Arg—AMC, Boc—Leu—Arg—Arg—AMC, Boc—Gly—Lys—Arg—AMC, and Boc—Leu—Ser—Thr—Arg—AMC. [Boc=r-butyloxycarbonyl; AMC=7-amino-4-methylcoumarin; LDL=low density lipoprotein]. This supports the view that matriptase prefers substrates with amino acid residues containing small side chains, such as Ala and gly as P2 sites. These results suggest that matriptase, in analogy with trypsin, exhibits broad spectrum cleavage specificity. This broad spectrum cleavage activity is likely to be the explanation of its gelatinolytic activity. Its trypsin-like activity appears to be distinct from Gelatinases A and B, which may cleave gelatin at glycine residues, the most abundant (almost up to one third of) amino acid residues in gelatin.

Structure motifs of the noncatalytic region of matriptase: The non-catalytic region of matriptase contains two sets of repeating sequences, which may serve as a regulatory and/or binding domain for interaction with other proteins. Four tandem repeats of about 35 amino acids including 6 conserved cysteine residues (FIG. 10A were found at the amino terminal region (aa 280-430) of its serine protease domain. They are homologous with the cysteine-containing repeat of the LDL receptor (Sudof et al., Science 228: 815-22 (1985)) and related proteins (Herz et al., EMBO J. 7: 4119-27 (1988)). All of these cysteine residues are likely to be involved in disulfide bonds. In LDL receptor, the homologous, seven repeating sequences serve as the ligand binding domain. By analogy, the four tandem cysteine-containing repeats may also be the sizes of interaction with other macromolecules. In addition, the cysteine-containing LDL receptor domain was found in other proteases, such as enteropeptidase (Matsushima et al., J. Biol. Chem. 269: 19976-82 (1994); and Kitamoto eta al., Proc. Nad. Acad. Sci. USA 91: 7588-92 (1994)).

Referring to FIG. 11A, the cysteine-rich repeats of matriptase (aa 280-314, aa 315-351, aa 352-387, and aa 394-430) (SEQ ID NO: 15) are compared with the consensus sequences of the human LDL receptor (SEQ ID NO: 16); LDL receptor-related protein (LRP) (SEQ ID NO: 17); human perlecan (SEQ ID NO: 18); and rat GP-300 (SEQ ID NO: 19). The consensus sequences are boxed. In FIG. 11B, C1r/s type sequences of matriptase (aa 42-155 and aa 168-268) (SEQ ID NOS: 20 and 21) are compared with selected domains of human complement subcomponent C1r aa 193-298) (SEQ ID NO: 22), C1s (aa 175-283) (SEQ ID NO: 23), Ra-reactive factor (RaRF) (aa 185-290) (SEQ ID NO: 24), and a calcium dependent serine protease (CSP) (aa 181-289) (SEQ ID NO: 25). The most consensus sequences are boxed.

The amino-terminal region of matriptase (aa 42-268) (SEQ ID NOS: 20 and 21) contains another two tandem segments with internal homology. These segments resemble partial sequences, originally identified in complement subcomponent C1r (Leytus et al., *Biochemistry* 25: 4855-63 (1986); and Journet et al., *Biochem. J.* 240-783-7 (1986)) and C1s (Mackinnon et al., *Eur. J. Biochem.* 169: 547-53 (1987); and Tosi et al., *Biochemistry* 26: 8516-24 (1987)). This C1r/s domain was also found in other serine proteases, including Ra-reactive factor, a C4/C2-activating component, enteropeptidase, an activator of trypsinogen (Matsushima et al., (1994)), and a calcium-dependent serine protease that is able to degrade extracellular matrix. These C1r/s-containing serine proteases appear to be involved either in a protease activation cascade or in extracellular matrix degradation. IN addition, there are at least six members of the asracin subfamily of zinc metalloprotease which were found to contain this C1r/s domain. These include bone morphogenetic protein-1 (Wozney et al., *Science* 242: 1528-34 (1988)), and *Drosophila tolloid* gene, a dorsal-ventral patterning protein (Shimell et al., Cell 67: 469-81 (1991)), quail 1, 25-dihydroxyvitamin D3-induced astacin like metallopeptidase that may play a role in the degradation of eggshell matrix, sea urchin blastula protease-10 (that could be involved in the differentiation of ectodermal lineages and subsequent patterning of the embryo), Xenopus embryonic protein UVS.2, a marker for developmental stage, and sea urchin VEB gene that is expressed in a spatially restricted pattern during the very early blastula stage of development. The majority of these C1r/s-containing, asracin metalloproteases appear to play a role in protein-protein interactions and embryonic development. The C1r/s domain has been also found in nonprotease proteins. These include neuropilin (A5 protein), a calcium-independent cell adhesion molecule that is developmentally-expressed in the nervous system and tumor necrosis factor-inducible protein TSG-6, a hyaluronate-binding protein that may be involved in cell-cell and cell-matrix interaction during inflammation and tumorigenesis.

FIG. 12 provides a schematic representation of the structures of matriptase. The protease consists of 683 amino acids, and the protein product has a calculated mass of 75,626. The protease contains two tandem complement subcomponent 1r and 1s (C1r/s) and four tandem LDL receptor domains. The serine protease domain is at the carboxyl terminus.

An amino acid hydrophobic region was identified at the amino-terminus. This region is likely to serve as a signal peptide.

Example 3

Method of Using Matriptase as a Diagnostic Indicator

As indicated above, nipple aspirate, tissue biopsy, archival tissue, fluid from needle biopsy, or any biological sample containing cells or biological fluid can also be used as means of identifying the presence of matriptase in cells. The presence of matriptase can also be detected in tissue (e.g., epithelial cells) other than in the lactating breast. Given the plasma membrane localization, ECM-degrading activity and expression in breast cells of matriptase, forms of the protein and matriptase-protein complexes may be involved in cancer onset and progression, including cancer invasion and metasis. Accordingly, agents which modulate matriptase activity or expression may be used to inhibit cancer onset and progression, or the onset and progression of other pathologic conditions.

One such compound is the soybean-derived, Bowman-Birk inhibitor (BBI) (Birk, *Methods Enzymol.* 45: 700-7 (1976). BBI is an inhibitor of serine proteases and has previously been described to possess anti-cancer activity by preventing tumor initiation and progression in model systems (see, e.g., Kennedy et al., *Cancer Res.* 56: 679-82 (1996)). The finding that the matriptase in the tissue has different significance than the finding of matriptase in the completed form as found in human milk makes it possible to identify persons who would benefit from such inhibitors. For example, a method of treating malignancies and pre-malignant conditions of the breast comprises (1) identifying the presence of matriptase in breast tissue or fluid from the breast and, if such matriptase if found, administration of a tumor formation-inhibiting effective amount of BBI. A concentrate of BBI, BBIC, can be administered in dosage sufficient to obtain a blood level of 0.001 to 1 mM concentration of BBI in the blood as a means of inhibiting tumor initiation in a susceptible to breast cancer. As indicated by presence of matriptase in nipple aspirate or in tissue from biopsy, including tissue from needle biopsy. BBI can decrease matriptase activity in a dose-dependent manner, as indicate by fluorescent substrate assay and zymography in tumor initiation and progression model systems. BBI interacts directly with the serine protease active site on matriptase.

Example 4

Molecular Modeling of Forms of Matriptase

In this example, we set forth a method of identifying molecules (e.g., peptides and small compounds) that can interact with the complexed and uncomplexed forms of matriptase. By using molecular modeling, with the programs described herein or using other available programs, compounds can be identified that bind to the active site of matriptase or to other relevant sites on matriptase, such as C1s/C1s.

to understand molecular basis for the differential expression of a major uncomplexed matriptase in T-47D cells, we compared to a major complexed form in the lactating mammary gland. The interaction between matriptase and HAI-1 was investigated by comparing the structural differences between complexed and uncomplexed matriptase and by three-dimensional modeling of the interaction of the serine protease domain of matriptase with both Kunitz domains of HAI-1. These results revealed that complexed matriptase is in its activated, two-chain form, and that the Kunitz domain I of HAI-1 is likely to be the inhibitory domain for the enzymes.

Materials and Methods. Source of mAbs: Rat-derived, anti-matriptase mAb 21-9 was produced using matriptase isolated from T-47D breast cancer cells as immunogen, as described previously (see Lin et al., 1997 and related U.S. patent application 08/957,816 to Dickson et al. filed on Oct. 27, 1997). Mouse-derived anti-matriptase mAb M32 and anti-HAI-1 mAbs M58 and M19 were produces using 95-kDa matriptase/HAI-1 complex as immunogen, as described in Example 1.

Purification of matriptase from human milk, T-47D breast cancer cells, and MTSV 1.1 B milk-derived mammary epithelial cells—Matriptase is expressed by the lactating mammary gland, by SV40T antigen-immortalized mammary luminal epithelial cells, and by human breast cancer cells. While the enzyme was detected in a complexed form in milk, it was a mixture of complexed and uncomplexed forms in MTSV 1.1 B cells, and it was primarily in an uncompleted form in T-47D cells. To purify the complexed matriptase, human milk was fractionated by Cm-Sepharose chromatography, and the 95-kDa matriptase complex fractions were then loaded onto an anti-matriptase mAb 21-9-Sepharose immunoaffinity column, as described above in Example 1. Bound proteins were eluted by 0.1 M glycine buffer, pH 2.4, and stored in this low pH conditions. To purify uncomplexed matriptase, the complexed matriptase and HAI-1 were first depleted by passing serum-free T-47 D cell-conditioned medium through an anti-HAI-1 mAb M58-Sepharose column. The unbound fraction (flow-through) was further loaded onto a 21-9-Sepharose column, and bound proteins were eluted by 0.1 M glycine buffer pH 2.4, as described previously (Lin et al., 1997). The eluted proteins were stored in low pH to prevent their degradation. A mixture of uncomplexed and complexed matriptase was purified from MTSV 1.1 B cell-conditioned medium by anti-matriptase 21-9-Sepharose immunoaffinity chromatography.

Diagonal gel electrophoresis: Two different types of diagonal gel electrophoresis were carried out, non-boiled/boiled and non-reduced/reduced. The non-boiled/boiled diagonal gel electrophoresis was used to examine the constituent components of matriptase/HAI-1 complexes and the non-covalent interaction between matriptase and HAI-1, as described in Example 1. Briefly, in the first dimension, the matriptase complexes were resolved in the absence of reducing agents by SDS polyacrylamide gel electrophoresis under non-boiled conditions. A gel strip was sliced out, boiled in SDS sample buffer in the absence of reducing agents, and electrophoreses on a second SDS polyacrylamide gel. TO examine constituent components and their covalent interactions, matriptase samples from different sources were subjected to non-reduced/reduced diagonal gel electrophoresis. In the first dimension, matriptase was boiled in SDS sample buffer in the absence of reducing agents,; in the second dimension, the gel strip was boiled in the presence of reducing agents.

Amino acid sequence analysis of the 45- and 25-kDa fragments of matriptase: Mile-derived 95-kDa matriptase complexes were purified using a combination of CM-Sepharose chromatography and anti-matriptase mAb 21-9-Sepharose immunoaffinity chromatography, as described above. Both 45- and 25-kDa fragments of matriptase were resolved by non-reduced/reduced diagonal gel electrophoresis, as described above, and then transferred to polyvinylidene fluoride (PVDF) membranes. The amino-terminal sequences of these two fragments were determined as described previously (Matsudaira, *J. Biol. Chem.* 262: 10035-38) (1987) in the Howard Hughes Medical Institute Biopolymer Laboratory & W. M. Keck Foundation Biotechnology Resource Laboratory at Yale University.

Proteolytic activity of matriptase determined by cleavage of trypsin substrate, BOC—Gln—Ala—Arg—AMC: A variety of synthetic, fluorescent protease substrates with arginine or lysine as P1 sites can be cleaved by matriptase, as described in Example 2. Among these substrates, t-butyloxycarbonyl (BOC)—Gln—Ala—Arg-7-amino-4-methyl-coumarin (Sigma; St. Louis, Mo.) is likely to be the best one. Using this substrate, matriptase was assayed in 20 mM Tris buffer pH 8.5 at 25° C. in a total volume of 200 μl. The final substrate concentration was 0.1 mM. The rate of cleavage was determined with a fluorescence spectrophotometer (Hitachi, F-4500).

Immunoblotting: Protein samples were resolved by 10% SDS-PAGE, transferred overnight to PVDF, and subsequently probed with mAbs, as indicated. Immunoreactive polypeptides were visualized using HRP-labeled secondary antibodies and the ECL detection system (Pierce, Rockford, Ill.; NEN, Boston Mass.).

Preparation of M58-Sepharose column and immunoaffinity chromatography: An immunoaffinity matrix was prepared by coupling 5 mg of mAb M58/ml of CNBR-activated Sepharose 4B, as specified in the manufacturer's instructions (Pharmacia; Piscataway, N.J.). The immunoaffinity column was equilibrated with PBS, and the concentrated medium from T-47D human breast cancer cells was loaded onto a 1-ml column at a flow rate of 7 ml/h. The column was washed with 10 ml of 1% Triton X-100 in PBS and then 10 ml of PBS. Bound proteins were then eluted by 0.1 M glycine-HCl (pH 2.4), and fractions were immediately neutralized with 2 M Trizma base.

Northern analysis of HAI-2: Total RNA (10 μg) from T-47D cells was denatured and electrophoresed, and transferred to a nylon membrane. The membrane were hybridized with $^{32}$P-labeled HAI-2 fragment, as described (Kawaguchi et al., *J. Biol. Chem.* 272: 27558-64 (1997).

Modeling: Homology modeling, as implemented in MODELLER (Sali et al., *PROTEINS: Structure Function & Genetics* 23: 318-26 (1995)) was chosen to build the three-dimensional structure of the serine protease domain (B chain) of matriptase and of the two Kunitz domains of HAI-1. The program BLAST (Altschul et al., *Nucleic Acids Res.* 25: 3389-3402 (1997)) was used to search the Protein Databank (PDB) (Bernstein et al., *J. Mol. Biol. Chem.* 112: 535-42 (1977)) for template proteins with known structures that have similar amino acid sequence to matriptase and to HAI-1. BLAST was also used to align all structures with the target sequence. Thrombin, entry 1hxe from PDB, with 234% identifies, 53% positives and 6% gaps was found to be a good template for matriptase. The protease inhibitor domain of Alzheimer β-amyloid protein precursor, entry 1app from PDB, with 45% identities and 56% positives was found to be a good template for the Kunitz domain of HAI-1. The same template, 1aap, with 45% identities and 62% positives, was used to build the structure of the Kunitz domain 2 of HAI-1. Hydrogens were assigned using HBUILD (Brunger et al., *PROTEINS: Structure, Function & Genetics* 4: 148-56 (1988) option within th eCHARMM program. All structures were then refined using the program CHARMM (Brooks et al., *J. Comput. Chem.* 4: 187-217 (1983)) with the all atom parameter set CHARMM22 (MacKerell, Jr. et al., *J. Phys. Chem.* 102: 3586-16 (1997). All structures were first minimized with 50 steepest descent steps and 500 adopted-basis Newton Raphson steps. Molecular dynamics, MD, simulations were used to further refine every structure. In MD simulations 1fs time step and a temperature of 300 K were used. The Hoenig solvation model (Sharp et al., *Biochem.* 30: 9686-97 (1991), as implemented in CHARMM, was used to represent the solvation effect. The protease-inhibitor complexes were built by orienting the inhibitor with the P1 residues, Arg-260 in Kunitz domain 1 and Lys-385 in Kunitz domain 2, in the direction of the S1 site of matriptase. The initial distance between the P1 residue and Asp-185, using B chain numbering, from the S1 site, was between 17-19 Å. Self-guided molecular dynamics simulation (SGMD) (Wu et al., *J. Chem. Phys.* 110: 9401-10 (1999)), which was shown to have a much better conformational search efficiently than the conventional MD method, was used to obtain the equilibrated structure of the complex between the serine protease domain of matriptase and the Kunitz domains of HAI-1. A restraining potential was applied to gradually decrease the distance between the guanidino or amino group of the P1 residue from HAI-1 and the carboxyl group of Asp-185 from matriptase. The final distance between the two residues was set to be between 2.2 and 6.0 Å, as observed in the X-ray structure of the trypsin complex with the soybean trypsin inhibitor, entry 1avw in PDB (Bernstein et al., 1977). Matriptase was fixed for the first 100 to 280 ps to save computer time. This was followed by 100 ps SGMD, without constraining matriptase.

Results. Complexed matriptase is an activated two chain form, but the majority of the uncomplexed enzyme is in a single chain, zymogen form: In Examples 1 and 2, matriptase was detected in T-47D cells mainly as an uncomplexed form, compared to a 95-kDa complex with a 40-kDa fragment of HAI-1 in human milk. The strong interaction between matriptase and HAI-1 could be dissociated after boiling in the absence of reducing agents. Because HAI-1 was also detected mainly in its uncomplexed form in T-47D cells, the interaction between matriptase and HAI-1 appeared not to occur. Some serine protease inhibitors, such as bovine pancreatic trypsin inhibitor (Ruhlmann et al., *J. Mol. Biol.* 77: 417-36 (1973)) and squash seed protease inhibitor (Zbyryt et al., *Biol. Chem. Hoppe Seyler* 372: 255-62 (1991)), are able to bind to the latent form of serine proteases, such as trypsinogen. However, for most of the serine proteases, cleavage of the enzyme at a canonical activation motif, resulting in proper formation of a substrate binding pocket, is required for their binding to serine protease inhibitors. Therefore, lack of interaction between T-47D cell-derived matriptase and HAI-1 could result from fact that the majority of matriptase produced by T47D cells is in the single chain, zymogen form. In contrast, complexed matriptase, isolated from human milk, is likely to be in its activated, two-chain form. In addition, matriptase was detected in a mixture of complexed and uncomplexed forms in MTSV 1.1 B, milk-derived, SV-40 immortalized mammary epithelial cells (see Example 1). This could result from a mixture of latent and activated matriptase produced by these cells. To further test this hypothesis, we have isolated matriptase from three sources, and these three matriptase preparations were subjected to non-reduced/reduced diagonal gel electrophoresis. In this electrophoresis assay, proteins that contain multiple disulfide-bonded components are dissociated into the constituent components, that appear on the same electrophoretic path. In contrast, single-chain proteins are not dissociated. The complex-derived matriptase (from milk) was converted to two groups of polypeptides with apparent sizes of 45-kDa (A chain) and 25-kDa (B chain). In contrast, the uncomplexed matriptase (from T-47D cells) was observed as a single chain, with apparent size of 70-kDa in this diagonal gel electrophoresis system. Consistently, a mixture of single-chain matriptase and two-chain matriptase was observed for preparations isolated from MTSV 1.1 B cells. These results suggest that complexed matriptase is a two-chain protease, whereas uncomplexed matriptase is a single-chain protein.

To determine the position of the cleavage site for the generation of the two-chain form of matriptase, the 45- and 25-kDa components were each subjected to N-terminal amino acid sequence analyses. The amino acid residues obtained from the 25-kDa B chain were VVGGTDADE- GEWP (SEQ ID NO: 37). This sequence begins with the likely cleavage site within the activation motif in matriptase. When the 45-kDa A chain (including two major plus one minor spots) was sequenced, two overlapping sequences (SFVVTSVVAFpTDSKTVQRT (SEQ ID NO: 38): TVQRTQDNSCSFGLHARGVE (SEQ ID NO: 39) were obtained, and both matched sequences close to the amino terminis of matriptase. These two different amino-terminal sequences may be derived from the two major spots of matriptase A chain and suggest that the different migration rates of the two components result from their different amino termini.

Inhibition of matriptase activity by the interaction with HAI-1: HAI-1, a protein containing contains two protease inhibitory domains (Kunitz domains), was initially identified as a binding protein of matriptase. However, gelatinolytic activity was observed for the 95-kDa matriptase/HAI-1 complex, as described in Example 2. Because Kunitz inhibitors are known to bind and inhibit serine proteases in a reversible and competitive mode, the gelatinolytic activity of the 95-kDa matriptase/HAI-1 complex could result from the excessive levels of substrate (1 mg/ml of gelatin) under the conditions of zymography. Therefor, to demonstrate that HAI-1 is an inhibitor of matriptase activity, we took advantage of the fact that the interactions between serine proteases and Kunitz-type inhibitors are acid sensitive and reversible. Both matriptase and HAI-1 were co-purified from human milk by immunoaffinity chromatography and maintained in their uncomplexed status in glycine buffer pH 2.4. When this matriptase/HAI-1 preparation was brought to pH 8.0 and incubated at 37° C., the interaction between matriptase and HAI-1 (in the 95-kDa complex) was observed to occur after incubation time as short as 5 min. The uncomplexed matriptase became undetectable by immunoblot after 30 and 60 min. of incubation (FIG. 13A). Strong gelatinolytic activity was observed for the uncomplexed matriptase in a gelatin zymogram (FIG. 13B), in contrast to the trace amounts of gelatinolytic activity that were observed for the 95-kDa complex. In addition, the rate of cleavage of a synthetic, fluorescent substrate by matriptase was decreased following complex formation (FIG. 13C). These results provide directed evidence that HAI-1 is an inhibitor of matriptase and that the interaction of these two molecules results in catalytic inhibition that is acid sensitive and reversible.

Different matriptase/HAI-1 complexes result from the binding of matriptase with different fragments of HAI-1: In Example 1, two matriptase/HAI-1 complexes were purified from human milk: (1) a 95-kDa complex containing matriptase and a 40-kDa fragment of HAI-1 and a 85-kDa complex containing matriptase and (2) a 25-kDa fragment of HAI-1. In contrast, in T-47D breast cancer cells, two matriptase complexes with apparent sizes of 95- and 110-kDa were detected by anti-matriptase mAb (Lin et al., 1997). These two complexes were also recognized by anti-HAI-1 mAbs, suggesting that the T-47D cell-derived 110- and 95-kDa matriptase complexes contain HAI-1. The 95-kDa complex could contain matriptase and the 40-kDa HAI-1 fragment, as does the milk-derived 95-kDa complex. However, the components of the 110-kDa complex are not clear. Thus, to investigate the components of these two complexes, a combination of immunoaffinity purification using anti-HAI-1 mAb M58-Sepharose and non-boiled/boiled diagonal gel electrophoresis was performed. As expected, both 110- and 95-kDa complexes were purified by anti-HAI-1 mAb M58-Sepharose. In addition to these complexes, two major HAI-1 fragments, with apparent sizes of 50-kDa and 40-kDa, as well as minor ones between them, were purified by immunoaffinity chromatography and verified by immunoblot. Both purified 110- and 95-kDa complexes were capable of dissociation by boiling in the absence of reducing agents, and matriptase was likely to be released from these two complexes.

To further investigate whether the 50- and 40-kDa HAI-1 fragments are the constituent subunit(s) of the 110- and 95-kDa complexes, respectively, both complexes were subjected to non-boiled/boiled diagonal gel electrophoresis (FIG. 4). The 95-kDa complex was converted, by boiling, to matriptase and to a 40-kDa protein that exhibited the same migration rate as the 40-kDa fragment of HAI-1. The 110-kDa complex was converted, by boiling, to matriptase and to a 50-kDa protein, whose migration rate is the same as that of the 50-kDa fragment of HAI-1. Because both 110- and 95-kDa complexes were captured by immobilized anti-HAI-1 mAb M58 (immunoaffinity chromatography) and detected by immunoblot analysis using another anti-HAI-1 mAn M19, these 50- and 40-kDa proteins are likely to be HAI-1 fragments that interact with the anti-HAI-1 mAbs. This observation suggests that the cancer cell-derived 95-kDa matriptase complex resembles the one previously isolated from milk as described in Example 1,a nd contains matriptase bound to the 40-kDa fragment of HAI-1. The 110-kDa complex contains the 50-kDa fragment of HAI-1.

Three-dimensional structure of B-chain of matriptase and HAI-1 as deduced by molecular modeling: To gain a better understanding of the interaction between matriptase and the two Kunitze domains of HAI-1, we utilized homology modeling to depict the three-dimensional structures of the serine protease domain of matriptase (B-chain) and of both Kunitz domains of HAI-1. Human thrombin was used as a template protein for matriptase. Since the sequence identity and similarity between matriptase and human thrombin are 34% and 53%, respectively, the 3D structure of matriptase can be accurately modeled. The protease inhibitor domain of Alzheimer's amyloid β-protein was used as template protein for Kunitz domains 1 and 2 of HAI-1, respectively. The sequence identities of Kunitz domains 1 and 2 with the protease inhibitor domain of Alzheimer's amyloid β-protein are 45% and the modeled structures are expected to have a main-chain RMS error as low as 1 Å for 90% of the residues (Sali, *Curr. Opin. Biotech.* 6: 437-51 (1995)).

Based on the high sequence identity between matriptase and trypsin, thrombin, and factor Xa, we propose that conserved Cys residues should form conserved disulfide bonds. Thus, the serine protease domain (B-chain) of matriptase is likely to have three disulfide bonds: Cys-27 and Cys-43, Cys-162 and Cys-166, Cys-187, and Cys-216 (the numbers of residues were designated based on the B-chain itself). Residues Ser-191, His-42, and Asp-97 form the catalytic triad center and are positioned on the surface of the enzyme. The disulfide bond between Cys-27 and Cys-43 stabilizes the position of His-42, as in trypsin. A negatively charged residue, Asp-185, is located at the bottom of the S1 binding site, which is consistent with the experimental data showing the preference of matriptase for substrates with positively charged residues, Arg/Lys at the P1 position (Example 2). The disulfide bond between Cys-216 and Cys-187 and the hydrogen bond between Asn-220 and Ser-188 stabilize the position of Asp-185, as in trypsin. Gly-215, Cys-216, Ala-217 and Gln-218 are at the entrance of the S1 binding pocket. The S1' pocket is proposed to be marked by Leu-18, Ala-20, Leu-21, Ile-26 and Trp-58, which form a hydrophobic binding site. The disulfide bond between Cys-27 and Cys-43 stabilizes the position of Ile-26.This may be important for the geometry of the binding site. In addition to these features, it is proposed that matriptase has a negatively-charged binding site, formed by Asp-46, Asp-47 and Asp-91.

Using the same approach as for matriptase, the position of disulfide bonds in the Kunitz domains 1 and 3 of HAI-1 were assigned. The three disulfide bonds in Kunitz domain 1 are between Cys-275 and Cys-296, Cys-250 and Cys-300, Cys-283 and Cys-259. The disulfide bond between Cys-250 and Cys-300 bridges the terminal sections of this domain, and the disulfide bond between Cys-2598 and Cys-283 stabilizes the position of Arg-260 (P1 residue), Arg-258 and Leu-284 (P1' residue).

The structure of the Kunitz domain 2 of HAI-1 also has three disulfide bonds, Cys375-Cys425, Cys384-Cys408, Cys400-Cys421. The disulfide bond between Cys-375 and Cys-425 bridges the terminal sections of Kunitz domain 2. The disulfide bond between Cys-384 and Cys-408 stabilizes the position of Lys-385 (P1 residue) and Leu-383 (putative P1' residue). It should be noted that the position of Leu-383 corresponds to that of Arg-258 from Kunitz domain 1. The residue corresponding to Leu-284 from Kunitz domain 1 is Tyr-409. These two structural alterations may influence the binding of the Kunitz domain 2 to matriptase.

Interactions between matriptase and both Kunitz domains of HAI-1 as determined by molecular modeling: The equilibrated structure of the complex between the Kunitz domain 1 and matriptase reveals that salt bridges are the major binding forces between the two proteins. It is important to note that Arg-258 and Arg-260 bind to Asp residues that are about 20 Å apart. Arg-260 of HAI-1 binds to the S1 site of matriptase, while Arg-258 of HAI-1 binds to the negatively charged binding site of matriptase. A similar binding mode was previously observed in the X-ray structure of trypsin complexed with soybean trypsin inhibitor (Bernstein et al., 1977). In both cases, the two Arg residues, separated by Ile in soybean trypsin inhibitor and by Cys in HAI-1, bind to Asp residues that are distant in the protease. In addition to salt bridges, a hydrophobic interaction was observed between Leu-284 of HAI-1 and the hydrophobic pocket, formed by Ala-20, Ile-26 and Trp-58 in matriptase. This suggests that matriptase may prefer substrates with a hydrophobic P1' residue and that the size of that residue is determined by the size of the S1' site.

In the complex between matriptase and the Kunitz domain 2 of HAI-1, the P1 residue, Lys-385, binds more weakly to the S1 site than does Arg-260 from Kunitz domain 1, because bidentate interactions between oppositely charged groups are known to be more stable than monodentate interactions. This was previously observed for a series of thrombin inhibitors. For example, DuP714, with Arg as P1 residue, has a Ki value that is 6 times lower than the analog with Lys as P1 residue (Weber et al., *Biochem.* 34: 3750-7 (1995). In addition to weaker interaction between the P1 site (Lys-3 85) of the Kunitz domain 2 and the S1 site (Asp-185) of matriptase B-chain, the negatively charged residue (Glu-386) next to the P1 residue in Kunitz domain 2 may also decrease the binding of Lys-385 to the S1 site. In contrast, the corresponding residue in Kunitz domain 1 is Gly-261, which is non-charged and the smallest residue. Another possible important residue is Leu-383; this residue binds weakly to the putative S1' site, suggesting the importance of this site for substrate recognition (in addition to the S1 site). This residue corresponds to Arg-258 from the Kunitz domain 1 of HAI-1, suggesting that the Kunitz domain 2 of HAI-1 binds in a distorted orientation to matriptase; this may further decrease its affinity for matriptase, when compared to Kunitz domain 1. Tyr-409 binds to the top of the putative S1' binding site. Tyr-409 is connected to Leu-383 through the Cys-384-Cys-408 disulfide bond, thus not allowing Leu-383 to interact properly with the putative S1' site, since the positions of the two residues are interconnected. In summary, our results showed that HAI-1 Kunitz domain 1 has a much better interaction with matriptase than HAI-1 Kunitz domain 2.

In Example 2, matriptase was observed to exhibit trypsin-like activity, both in terms of its primary cleavage at arginine residues and in its rather loose selectivity for substrate P2 sites. The gelatinolytic activity of matriptase is likely to be attributed to this broad spectrum cleavage activity. Thus, it appears likely that precise mechanisms, whereby the potent proteolytic activity of matriptase can be regulated, would be required in order to prevent unwanted proteolysis. Matriptase, like most of other serine proteases, may be synthesized as a single-chain zymogen, lacking binding affinity to its cognate inhibitor, HAI-1. A likely mechanism for activation of matriptase is the conversion of single-chain matriptase into a two-chain form, by cleavage at the activation motif. Thus, proteolytic activation of matriptase is likely to be an irreversible process; interaction of the enzyme with its Kunitz-type inhibitor could provide an important inhibitory control to prevent unwanted proteolysis. In support of this hypothesis is the fact that the majority of matriptase was detected either in an uncomplexed single-chain form or in a two-chain form that was observed to be tightly bound with its inhibitor.

During lactation, remodeling of mammary basement membrane is enhanced (Beck et al., *Biochem. Biophys. Res. Commun.* 190: 616-23 (1993)), and proteases have been implicated in this process (Talhouk et al., *Development* 112: 439-49 (1991)). Identification of matriptase in human milk suggests that this enzyme could play a role in tissue remodeling and in other aspects of lactation. This hypothesis has been further confirmed by the fact that matriptase was identified specifically as an activated, tow-chain form in human milk, and suggests that activation of the protease is enhanced during lactation. While matriptase is activated, in the lactating mammary gland, it is inhibited by binding to HAI-1. These results further suggest that matriptase is likely to be synthesized as a zymogen, activated only at the proper time and in the proper place, then inhibited by HAI-1 in order to prevent unwanted proteolysis, and finally released as a matriptase/HAI-1 complex in milk.

In T-47D breast cancer cells, single-chain matriptase is the major form of the protease, and its complexes (110- and 95-kDa) can also be easily detected by immunoblot. Nevertheless, matriptase was initially identified in this cell type as the major gelatinolytic activity, as assessed by gelatin zymography (Shi et al., *Canc. Res.* 53: 1409-15 (1993)). These results suggest that the single-chain matriptase may be enzymatically active or that there is a trace amount of two-chain, active matriptase with a similar size to single-chain matriptase expressed by T-47D cells. The former possibility may be unlikely, because high levels of single-chain matriptase and HAI-1 coexist in their uncomplexed forms, where the active site triad and substrate binding pocket of single-chain matriptase may not be well-formed. The existence of a low level of two-chain matriptase, which contributes to the gelatinolytic activity found in T-47D cells, may be more likely. It is necessary to have single-chain matriptase without contamination of two-chain matriptase in order to carry out experiments to fully prove single-chain matriptase to be latent. Expression of matriptase with a point mutation at the activation site could be the most convincing way to obtain single-chain matriptase without contamination of two-chain matriptase.

HAI-1 is likely to be synthesized as a 55-kDa, integral membrane protein, based on a putative transmembrane domain at its C-terminus (Shimomura et al., *J. Biol. Chem.* 272: 6370-6 (1997). This is supported by the observations that the apparent size of the membrane-bound inhibitor is 55-kDa and that the association of the inhibitor with the membrane fraction resists a wash of 2 M KCl; these are characteristics of an integral membrane protein. The 50-kDa fragment of HAI-1 is likely to be a cleaved form of HAI. The cleavage site is likely to be near to the transmembrane domain, since the 50-kDa fragment was detected as a major form of the inhibitor in conditioned media of T-47D cells. The 50-kDa HAI-1 is likely to have both Kunitz domains and the LDL receptor domain, and to be able to interact with matriptase to form the 110-kDa complex.

Further degradation of the 50-kDa HAI-1 fragment also could occur at the C-terminus, probably with the Kunitz domain 2, to generate the 40-kDa fragment. Since the amino-terminal sequence of the 40-kDa fragment was identified to be GPPPAPPGLPAG (Example 2; and Shimomura et al., (1997)), this fragment is not big enough to cover the entire Kunitz domain 2 (Shimomura et al., (1997)). Thus, the 40-kDa HAI-1 fragment is likely to contain only one intact Kunitz domain (domain 1) and the LDL receptor domain. This 40-kDa HAI-1 fragment is also able to complex with matriptase to form the 95-kDa species. The 25-kDa fragment, which still exhibits binding affinity to matriptase discussed in Example 1, is likely to be generated by cleavage of the 40-kDa inhibitor fragment at the Arg-153 of HAI-1, because the first seven amino-terminal residues were identifies to be a sequence spanning residues 154 through 160 of the inhibitor. In common with the 40-kDa inhibitor fragment, the 25-kDa fragment contains only the Kunitz domain 1 and an LDL receptor domain; it is able to interact with matriptase to form an 85-kDa complex. These observations suggest that the Kunitz domain 1, but not domain 2 is likely to be the inhibitory domain for the matriptase. The proposed processing of matriptase and its inhibitor, and their interactions, are summarized in FIG. 14.

The hypothesis that the Kunitz domain 1 of HAI-1 is the one which may be responsible for inhibition of matriptase is further supported by observations from computer modeling. Since both the Kunitz domains 1 and 2 contain positively charged P1 residues (Arg-260 domain 1 and Lys-385 in domain 2), they each have the potential to inhibit trypsin-like serine proteases, such as matriptase, by using these residues to engage the substrate-binding pocket. In the Kunitz domain 1, the second alt bridge not only stabilizes the complex but also orients the inhibitor, so that it blocks access of substrates to the active site. This interaction is missing in the complex with Kunitz domain 2. Therefore, Kunitz domain 1 appears to be the one that is responsible for the formation of a stable complex with matriptase. This suggestion is consistent with the observation that the 40- and 25-kDa fragments of the inhibitor were able to form stable complexes with matriptase.

The second salt bridge was identified to be Arg258 of the inhibitor, binding to the anionic site of matriptase. A search for proteins which contain potential anti-trypsin-like serine protease Kunitz domains (Arg or Lys at P1 site) was carried out in GenBank. We identified a second Kunitz-type inhibitor containing an Arg residue in the corresponding position of Arg-258 of HAI-1 in *Homo sapiens*. This protein, identified by different groups, has three accession numbers (ABOO6534; U78095; and AF027205) in GenBank, and was named placental bikunin (Marlor et al., *J. Biol. Chem.* 272: 12202-8 (1997)) or HGF activator inhibitor 2 (EAI-2) (Kawaguchi et al., *J. Biol. Chem.* 272: 27556-64 (1997)). HAI-2, like HAI-1 was identified from MKN 45 human stomach carcinoma cells and shown to be an inhibitor of HGF activator (Kawaguchi et al., (1997). HAI-2 resembles HAI-1 in terms of its transmembrane domain and its two Kunitz domains. HAI-2 was also isolated from human placenta. Because it contained two Kunitz domains, it was also named placenta bikunin (two Kunitz domains). In addition to its blockage of HGF activator, placenta bikunin exhibits strong inhibition of human plasmin, human tissue kallikrein, human plasma kallikrein, and human factor XIa (Delaria et al., *J. Biol. Chem.* 272: 12209-14 (1997)).

The third important binding force identified between matriptase and the Kunitz domain 1 is a hydrophobic interaction between Leu-284 of the inhibitor and a hydrophobic pocket in matriptase, delimited by Leu-18, Ala-20, Ile-26 and Trp-58. The corresponding residue for this Leu-284 in the Kunitz domain 1 of placental bikunin/HAI-2 is Asp-72, a negatively charged residue, suggesting that this hydrophobic interaction may not occur when matriptase encounters placental bikunin/HAI-2. Thus, matriptase may have a weaker interaction with placenta bikunin/HAI-2 compared to its cognate inhibitor (HAI-1). This notion is supported by the observation that, although both matriptase inhibitor (HAI-1) and placenta bikunin/HAI-2 were expressed by T-47D cells and by MTSV 1.1 B cells, as determined by Northern analysis. Only HAI-1 has been identified to be in complexes with matriptase.

Although the stoichiometries of the components of the 110- and 95-kDa matriptase/HAI-1 complexes have not been directly determined, matriptase (70-kDa apparent size) and HAI-1 (40- and 50-kDa fragments) are likely to bind to each other in a 1:1 ratio, based on their sizes and the size of resultant complexes. We note that only a small amount of the 40-kDa HAI-1 fragment, relative to matriptase, was dissociated from the 95-kDa matriptase complex by boiling. This appearance of a relatively small amount of 40-kDa protein could result form its small size and its likely weaker affinity to Coomassie Blue. The binding between matriptase and HAI-1 appears to cause a more compacted configuration of these two proteins, and thus on gel electrophoresis the apparent sizes of the matriptase/HAI-1 complexes are smaller than those of the sum of their components.

Both matriptase and its cognate inhibitor are likely to be biosynthesized as integral membrane proteins. The "TM" indicates the location of the transmembrane domain. "I" stands for Kunitz domain 1; "II" for Kunitz domain 2; and "L" for LDL receptor domain. The proposed processing steps for both proteins are described in Example 4.

Example 5

Production of mAbs Which are Specifically Directed Against Active, Two-Chain Matriptase In order to investigate activation of matriptase, we obtained two anti-matriptase mAbs which specifically recognize the two-chain matriptase, but not the single-chain form (FIG. 17). Activation of matriptase, like other serine proteases may require cleavage of a single specific peptide bond in the canonical activation motif. This cleavage not only transforms catalytically inactive serine proteases into active forms but also triggers discrete, highly localized conformation changes. Thus, mAbs directed against these activation-associated conformational changes are theoretically able to distinguish the active matriptase from its latent form. In our previous studies, more than 80 hybridoma clones were generated using 95-kDa matriptase/KSPI complex as immunogens. Hybridomas were selected for the mAbs capable of recognizing the 95-kDa matriptase/KSPI complex under non-boiled conditions and uncomplexed matriptase after boiling. These anti-matriptase mAbs were further tested using the conditioned medium of T-47D breast cancer cells to selected mAbs which are able to distinguish complexed matriptase (e.g., a two-chain form) from uncomplexed matriptase (e.g., a single-chain form). In the cell-conditioned medium of T-47D cells, matriptase was expressed predominantly in uncomplexed, single-chain form and in two minor matriptase/KSPI complexes with apparent sizes of 110- and 95-kDa. Uncomplexed, active matriptase is also likely to exist and was detected as a major gelatinolytic activity by gelatin zymography. For most of these anti-matriptase mAbs as represented here by mAb M130 (FIG. 17, lane 1), matriptase was detected mainly in an uncomplexed form and two complexed forms (1100 and 95-kDa), which can be dissociated after boiling (FIG. 17, lane 2). In contrast, although mAb M123 (IgG$_1$) recognized the 95- and the 110-kDa matriptase complexes (FIG. 17, lane 3) as well as mAb M130, mAb M123 recognized the uncomplexed matriptase more weakly than mAb M130 as demonstrated by the weaker band (FIG. 17, lane 3). The immunoreactive signals of 1000 and 95kDa matriptase complexes were converted to matriptase after boiling (FIG. 17, lane 4). To further characterize mAbs M123 and M69 (IgG$_1$), another mAb was selected (M32), which is specifically directed against two-chain matriptase. We compared the immunoreactivity of the antibodies using purified, two-chain matriptase from human milk and single-chain matriptase, purified from T-47D cells. Both milk-derived and T-47D-derived matriptase were recognized by anti-matriptase mAb M32 (FIG. 17, lanes 5 and 6, respectively); however, mAbs M123 (FIG. 17, lanes 7 and 8, respectively) and mAb M69 (FIG. 17, lanes 9 and 10) only recognized the two-chained form of matriptase. Moreover, the two-chain form of matriptase appears to have a slower migration rate than that of the single-chain form of matriptase (FIG. 17, compared lane 5 with lane 6).

Although the present invention has been described in detail with reference to examples above, it is understood that various modifications can be made without departing from the spirit of the invention. All cited patents and publications referred to in this application are herein incorporated by reference in their entirety. Also incorporated herein by reference in their entirety are the following related U.S. Applications and patent. U.S. Ser. No. 60/124,006 filed Mar. 12, 1999; U.S. Pat. No. 5,482,848 to Dickson et al. which issued on Jan. 9, 1996; and U.S. Ser. No. 08/957,816 to Dickson et al. filed on Oct. 27, 1997.

DEPOSIT INFORMATION

Hybridoma M69 and hybridoma M123, which produce antibodies M69 and M123, respectively, were deposited on Sep. 28, 2005, with the American Type Culture Collection (ATCC), currently located at 10801 University Boulevard, Manassas, Va. 20110-2209, under the provisions of the Budapest Treaty for the International Recognition of the Deposit of Microorganisms for the Purpose of Patent Procedure ("Budapest Treaty"). The ATCC has assigned hybridoma M69 the ATCC Patent Deposit Designation No. PTA-7120, and has assigned hybridoma M123 the ATCC Patent Deposit Designation No. PTA-7121.

What is claimed is:

1. A murine monoclonal antibody or immunologically reactive fragment thereof which recognizes and binds to a protein complex comprising a two-chain form of matriptase, wherein said antibody is selected from the group consisting of M69 and M123.

2. The antibody or immunologically reactive fragment thereof of claim 1, wherein the immunologically reactive fragment is selected from the group consisting of scFv, Fab, Fab', and F(ab')₂.

3. An isolated antibody or immunologically reactive fragment thereof which selectively binds with greater affinity to a two-chain (active) form of matriptase of a human than to a single-chain (zymogen) form of matriptase of said human.

4. The antibody or immunologically reactive fragment thereof of claim 3, wherein the antibody is a monoclonal antibody.

5. The antibody or immunologically reactive fragment thereof of claim 3, wherein the immunologically reactive fragment is selected from the group consisting of scFv, Fab, Fab', and F(ab')₂.

6. The antibody or immunologically reactive fragment thereof of claim 3, wherein said single-chain form of matriptase comprises a polypeptide encoded by the nucleotide sequence of SEQ ID NO: 4, and the two-chain form of matriptase is produced by cleavage of said single-chain form of matriptase.

7. The antibody or immunologically reactive fragment thereof of claim 3, which binds to the two-chain (active) form of a matriptase protein that is present in a complex comprising Hepatocyte growth factor activator inhibitor-1 (HAI-1) or a fragment thereof.

* * * * *